(12) United States Patent
Sharifi-Mehr et al.

(10) Patent No.: US 12,226,321 B2
(45) Date of Patent: Feb. 18, 2025

(54) INSTRUMENTS FOR EXPANDABLE INTERBODY IMPLANTS

(71) Applicant: Howmedica Osteonics Corp., Mahwah, NJ (US)

(72) Inventors: Amir Ali Sharifi-Mehr, Bloomingdale, NJ (US); Oliver Buchert, Franklin Lakes, NJ (US); M. Todd Miller, Franklin Lakes, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 18/499,174

(22) Filed: Oct. 31, 2023

(65) Prior Publication Data

US 2024/0058140 A1 Feb. 22, 2024

Related U.S. Application Data

(63) Continuation of application No. 17/373,117, filed on Jul. 12, 2021, now Pat. No. 11,833,062, which is a
(Continued)

(51) Int. Cl.
| | |
|---|---|
| *A61F 2/46* | (2006.01) |
| *A61F 2/44* | (2006.01) |
| *A61F 2/30* | (2006.01) |

(52) U.S. Cl.
CPC .......... *A61F 2/4601* (2013.01); *A61F 2/4455* (2013.01); *A61F 2/4611* (2013.01);
(Continued)

(58) Field of Classification Search
CPC ............. A61B 17/8833; A61B 17/8841; A61F 2/4425; A61F 2/4455; A61F 2/447;
(Continued)

(56) References Cited

U.S. PATENT DOCUMENTS

| | | |
|---|---|---|
| 3,581,033 A | 5/1971 | Plumb |
| 4,743,230 A | 5/1988 | Nordquest |
| (Continued) | | |

FOREIGN PATENT DOCUMENTS

| | | |
|---|---|---|
| WO | 9531948 A1 | 11/1995 |
| WO | 2002017823 A1 | 3/2002 |
| (Continued) | | |

OTHER PUBLICATIONS

European Search Report for EP Application No. 18194369.7, mailed Feb. 11, 2019, 2 pages.
(Continued)

*Primary Examiner* — Larry E Waggle, Jr.
(74) *Attorney, Agent, or Firm* — Duane Morris LLP

(57) ABSTRACT

A system for implanting an expandable interbody implant into an intervertebral space includes an elongated tool, the distal end of which is removably securable to the implant. The proximal end of the tool has an attachment interface for detachable securement to a plurality of different modules, each of which is adapted to effectuate a different function of the delivery system. The different functions include: grasping the implant delivery tool, providing an impaction surface for driving the advancement of the implant, supplying a graft material into the implant, and actuating the expansion of the implant. One of the modules may include a fluid delivery system for supplying hydraulic fluid to expand the implant. A fluid reservoir of the fluid delivery system may be oriented transverse to the cannula that delivers the fluid to the implant. A grafting block can be used to help pre-pack the implant with graft material.

17 Claims, 49 Drawing Sheets

Related U.S. Application Data continuation of application No. 16/131,726, filed on Sep. 14, 2018, now Pat. No. 11,083,597.

(60) Provisional application No. 62/559,037, filed on Sep. 15, 2017.

(52) U.S. Cl.
CPC ..... *A61F 2002/30556* (2013.01); *A61F 2/447* (2013.01); *A61F 2002/4625* (2013.01); *A61F 2002/4631* (2013.01)

(58) Field of Classification Search
CPC ........ A61F 2/46; A61F 2/4601; A61F 2/4603; A61F 2/4611; A61F 2002/4615; A61F 2002/4625; A61F 2002/4631; A61F 2002/4681
See application file for complete search history.

(56) References Cited

U.S. PATENT DOCUMENTS

| | | |
|---|---|---|
| 5,702,455 A | 12/1997 | Saggar |
| 5,800,549 A | 9/1998 | Bao et al. |
| 5,993,416 A | 11/1999 | Choh et al. |
| 6,004,326 A | 12/1999 | Castro et al. |
| 6,167,787 B1 | 1/2001 | Jarvis |
| 6,264,659 B1 | 7/2001 | Ross et al. |
| 6,332,894 B1 | 12/2001 | Stalcup et al. |
| 6,395,007 B1 | 5/2002 | Bhatnagar et al. |
| 6,706,069 B2 | 3/2004 | Berger |
| 6,764,491 B2 | 7/2004 | Frey et al. |
| 6,796,959 B2 | 9/2004 | Davis et al. |
| 6,830,570 B1 | 12/2004 | Frey et al. |
| 6,830,574 B2 | 12/2004 | Heckele et al. |
| 7,060,073 B2 | 6/2006 | Frey et al. |
| 7,118,579 B2 | 10/2006 | Michelson |
| 7,235,082 B2 | 6/2007 | Bartish et al. |
| 7,481,812 B2 | 1/2009 | Frey et al. |
| 7,500,991 B2 | 3/2009 | Bartish, Jr. et al. |
| 7,530,970 B2 | 5/2009 | McArthur et al. |
| 7,575,580 B2 | 8/2009 | Lim et al. |
| 7,708,779 B2 | 5/2010 | Edie et al. |
| 7,799,033 B2 | 9/2010 | Assell et al. |
| 7,811,292 B2 | 10/2010 | Lo et al. |
| 7,892,239 B2 | 2/2011 | Warnick et al. |
| 7,958,804 B2 | 6/2011 | Badiali |
| 7,976,549 B2 | 7/2011 | Dye et al. |
| 7,985,256 B2 | 7/2011 | Grotz et al. |
| 7,988,695 B2 | 8/2011 | Dye |
| 8,043,293 B2 | 10/2011 | Warnick |
| 8,142,435 B2 | 3/2012 | Refai et al. |
| 8,147,554 B2 | 4/2012 | Hansell et al. |
| 8,157,845 B2 | 4/2012 | Warnick et al. |
| 8,216,317 B2 | 7/2012 | Thibodeau |
| 8,241,294 B2 | 8/2012 | Sommerich et al. |
| 8,241,364 B2 | 8/2012 | Hansell et al. |
| 8,252,060 B2 | 8/2012 | Hansell et al. |
| 8,343,224 B2 | 1/2013 | Lynn et al. |
| 8,414,590 B2 | 4/2013 | Oh et al. |
| 8,419,795 B2 | 4/2013 | Sweeney |
| 8,506,636 B2 | 8/2013 | Dye |
| 8,551,172 B2 * | 10/2013 | Park .................. A61F 2/441 623/17.12 |
| 8,568,420 B2 | 10/2013 | O'Halloran et al. |
| 8,663,332 B1 | 3/2014 | To et al. |
| 8,690,761 B2 | 4/2014 | Begemann et al. |
| 8,753,377 B2 | 6/2014 | McCormack et al. |
| 8,992,620 B2 | 3/2015 | Ashley et al. |
| 8,998,924 B2 | 4/2015 | Simpson et al. |
| 9,060,876 B1 | 6/2015 | To et al. |
| 9,271,844 B2 | 3/2016 | Prevost et al. |
| 9,668,876 B2 | 6/2017 | Blain et al. |
| 9,681,961 B2 | 6/2017 | Prevost et al. |
| 9,808,354 B2 | 11/2017 | Willis et al. |
| 9,808,355 B2 | 11/2017 | Sweeney |
| 9,814,602 B2 | 11/2017 | Faulhaber et al. |
| 9,855,080 B2 | 1/2018 | Rabiner et al. |
| 9,987,149 B2 | 6/2018 | Simpson et al. |
| 2001/0021853 A1 | 9/2001 | Heckele et al. |
| 2002/0049449 A1 | 4/2002 | Bhatnagar et al. |
| 2002/0147497 A1 | 10/2002 | Belef et al. |
| 2003/0018292 A1 | 1/2003 | Kuslich et al. |
| 2004/0083002 A1 | 4/2004 | Belef et al. |
| 2004/0143283 A1 | 7/2004 | McGill et al. |
| 2004/0186576 A1 | 9/2004 | Biscup et al. |
| 2005/0113842 A1 | 5/2005 | Bertagnoli et al. |
| 2005/0131419 A1 | 6/2005 | McCord et al. |
| 2005/0209698 A1 | 9/2005 | Gordon et al. |
| 2005/0222681 A1 | 10/2005 | Richley et al. |
| 2005/0245938 A1 | 11/2005 | Kochan |
| 2006/0004326 A1 | 1/2006 | Collins et al. |
| 2006/0079898 A1 | 4/2006 | Ainsworth et al. |
| 2006/0085075 A1 | 4/2006 | McLeer |
| 2006/0155297 A1 | 7/2006 | Ainsworth et al. |
| 2006/0206209 A1 | 9/2006 | Cragg et al. |
| 2006/0235426 A1 | 10/2006 | Lim et al. |
| 2007/0093897 A1 | 4/2007 | Gerbec et al. |
| 2007/0112299 A1 | 5/2007 | Smit et al. |
| 2007/0135921 A1 | 6/2007 | Park |
| 2007/0142843 A1 | 6/2007 | Dye |
| 2007/0161962 A1 | 7/2007 | Edie et al. |
| 2007/0179614 A1 | 8/2007 | Heinz et al. |
| 2007/0191860 A1 | 8/2007 | Heinz et al. |
| 2007/0225726 A1 | 9/2007 | Dye et al. |
| 2007/0225809 A1 | 9/2007 | Ray |
| 2007/0233260 A1 | 10/2007 | Cragg |
| 2008/0021563 A1 | 1/2008 | Chudzik |
| 2008/0065082 A1 | 3/2008 | Chang et al. |
| 2008/0077150 A1 | 3/2008 | Nguyen |
| 2008/0091211 A1 | 4/2008 | Gately |
| 2008/0161933 A1 | 7/2008 | Grotz et al. |
| 2008/0172060 A1 | 7/2008 | Collins et al. |
| 2008/0172127 A1 | 7/2008 | Perez-Cruet et al. |
| 2008/0221694 A1 | 9/2008 | Warnick et al. |
| 2008/0262502 A1 | 10/2008 | Ainsworth et al. |
| 2008/0306557 A1 | 12/2008 | Altarac et al. |
| 2009/0043312 A1 | 2/2009 | Koulisis et al. |
| 2009/0177236 A1 | 7/2009 | Saab et al. |
| 2009/0240341 A1 | 9/2009 | Diwan et al. |
| 2009/0248163 A1 | 10/2009 | King et al. |
| 2010/0070035 A1 | 3/2010 | Mayer |
| 2010/0116360 A1 | 5/2010 | Kanner et al. |
| 2010/0262188 A1 | 10/2010 | Rabiner et al. |
| 2010/0262245 A1 | 10/2010 | Alfaro et al. |
| 2010/0305703 A1 | 12/2010 | Lin |
| 2011/0009968 A1 | 1/2011 | McCormack |
| 2011/0125158 A1 | 5/2011 | Diwan et al. |
| 2011/0130835 A1 | 6/2011 | Ashley et al. |
| 2011/0137418 A1 | 6/2011 | O'Neil et al. |
| 2011/0230970 A1 | 9/2011 | Lynn et al. |
| 2011/0257688 A1 | 10/2011 | Miller et al. |
| 2011/0257745 A1 | 10/2011 | Miller et al. |
| 2011/0276142 A1 | 11/2011 | Niemiec et al. |
| 2011/0295370 A1 | 12/2011 | Suh et al. |
| 2012/0041557 A1 | 2/2012 | Frigg |
| 2012/0065613 A1 | 3/2012 | Pepper et al. |
| 2012/0067204 A1 | 3/2012 | Kanner et al. |
| 2012/0101576 A1 | 4/2012 | Dewey et al. |
| 2012/0101577 A1 | 4/2012 | Lee |
| 2012/0130387 A1 | 5/2012 | Simpson et al. |
| 2012/0136315 A1 | 5/2012 | Wieselblad et al. |
| 2012/0150241 A1 | 6/2012 | Ragab et al. |
| 2012/0265304 A1 | 10/2012 | Mayer |
| 2013/0006365 A1 | 1/2013 | Pepper et al. |
| 2013/0190875 A1 | 7/2013 | Shulock et al. |
| 2014/0005630 A1 | 1/2014 | Bagaoisan et al. |
| 2014/0107789 A1 | 4/2014 | Schaller et al. |
| 2014/0180415 A1 | 6/2014 | Koss |
| 2014/0303730 A1 | 10/2014 | McGuire et al. |
| 2015/0112437 A1 | 4/2015 | Davis et al. |
| 2015/0190242 A1 | 7/2015 | Blain et al. |
| 2015/0351925 A1 | 12/2015 | Emerick et al. |
| 2016/0030195 A1 | 2/2016 | Prevost et al. |

(56) References Cited

U.S. PATENT DOCUMENTS

| | | |
|---|---|---|
| 2016/0058575 A1 | 3/2016 | Sutterlin et al. |
| 2016/0113776 A1 | 4/2016 | Capote |
| 2016/0120653 A1 | 5/2016 | Hibri et al. |
| 2016/0242823 A1 | 8/2016 | Perez-Cruet et al. |
| 2016/0278822 A1 | 9/2016 | Davis et al. |
| 2016/0296344 A1 | 10/2016 | Greenhalgh et al. |
| 2016/0317324 A1 | 11/2016 | Cho et al. |
| 2016/0331542 A1 | 11/2016 | Faulhaber et al. |
| 2017/0056195 A1 | 3/2017 | Lutz et al. |
| 2017/0071753 A1 | 3/2017 | Josse et al. |
| 2017/0196702 A1 | 7/2017 | Agarwal et al. |
| 2017/0216044 A1 | 8/2017 | McCormack |
| 2017/0224484 A1 | 8/2017 | Pintor et al. |
| 2017/0258605 A1 | 9/2017 | Blain et al. |
| 2017/0290671 A1 | 10/2017 | Milz et al. |
| 2017/0290680 A1 | 10/2017 | Pinal et al. |
| 2017/0319352 A1 | 11/2017 | Dewey et al. |
| 2017/0333199 A1 | 11/2017 | Sharifi-Mehr et al. |
| 2017/0340358 A1 | 11/2017 | Bullard |
| 2017/0348115 A1 | 12/2017 | Greenhalgh et al. |
| 2018/0014944 A1 | 1/2018 | Davis et al. |
| 2018/0021148 A1 | 1/2018 | Baynham |

FOREIGN PATENT DOCUMENTS

| | | |
|---|---|---|
| WO | 2008041972 A2 | 4/2008 |
| WO | 2008131498 A1 | 11/2008 |

OTHER PUBLICATIONS

Extended European Search Report for Application No. 15189369.0 dated May 4, 2016.

Extended European Search Report for Application No. 17165366.0 dated Aug. 29, 2017.

International Search Report and Written Opinion dated Nov. 11, 2010 in relation International Application No. PCT/US2010/031247.

Stryker, AccuLIF, Expandable TLIF and PLIF Technology, Surgical Technique Guide, Copyright 2015, pp. 1-48.

Supplementary European Search Report, issued Aug. 27, 2013, in connection with related EU10765185.3.

* cited by examiner

INSTRUMENTS FOR EXPANDABLE INTERBODY IMPLANTS

CROSS-REFERENCE TO RELATED APPLICATIONS

This application is a continuation of U.S. patent application Ser. No. 17/373,117 filed Jul. 12, 2021, which is a continuation of U.S. patent application Ser. No. 16/131,726 filed Sep. 14, 2018, now U.S. Pat. No. 11,083,597, which claims the benefit of the filing date of U.S. Provisional Patent Application No. 62/559,037 filed Sep. 15, 2017, the disclosures of which are hereby incorporated herein by reference.

BACKGROUND OF THE INVENTION

Intervertebral implants are commonly used in spinal surgery, such as in interbody fusion procedures, in which an implant (e.g., a spacer or cage) is placed in the disc space between two vertebrae to be fused together. At least a portion of the disc is typically removed before the implant is positioned in the intervertebral space, and the implant may be supplemented with bone graft material to promote fusion of the vertebrae. Interbody fusion procedures may also be performed in conjunction with other types of fixation, such as pedicle screw fixation, to provide additional stability, particularly while the vertebrae fuse together.

Different interbody fusion procedures can be distinguished by their location along the spine (e.g., in the cervical, thoracic, or lumbar regions); by the type of implant used; and by the surgical approach to the intervertebral space, in which different surgical approaches often imply different structural characteristics of the implant or implants used. Different surgical approaches to the spine include anterior, posterior, and lateral. Examples of interbody fusion techniques performed along a posterior approach include posterior lumbar interbody fusion (PLIF) and transforaminal lumbar interbody fusion (TLIF). PLIF techniques typically include positioning two intervertebral implants into the intervertebral space along a posterior to anterior direction, with one implant being positioned towards the left side of the spine and one implant being positioned towards the right side of the spine. The implants used in such PLIF techniques typically have a straight shape, in that they extend along a central axis. TLIF techniques, by contrast, typically include positioning one intervertebral implant into the intervertebral space (often towards the anterior portion of the intervertebral space) from the posterior of the patient, but the spine is approached on one side from a more lateral position than in PLIF techniques. The implants used in such TLIF techniques are often curved, such that they have an overall kidney bean-like shape. Interbody fusion techniques performed along a lateral approach, on the other hand, often involve implants that are generally symmetric along their linear longitudinal axis (e.g., having a substantially rectangular or oval shape), but the implants are typically larger than those used in PLIF or TLIF techniques. That is, intervertebral implants used in lateral approaches often cover a substantial portion of the disc space.

Included among the different types of intervertebral implants are expandable implants. Such implants often have an initially contracted configuration, such that they have a low profile in the superior-inferior direction, in order to ease insertion into the intervertebral space. Such expandable implants can then be expanded in the superior-inferior direction after implantation, so as to securely engage and stabilize the vertebrae on both sides of the intervertebral space. Examples of such expandable intervertebral implants are disclosed in U.S. Patent Application Publication No. 2017/0333199 (hereinafter "the '199 Publication"), U.S. Pat. No. 8,992,620 (hereinafter "the '620 Patent"), and in U.S. Patent Application Publication No. 2017/0290671 (hereinafter "the '671 Publication"), the disclosures of which are hereby incorporated by reference herein as if fully set forth herein. Expandable intervertebral implants having certain similar features to those in the '620 Patent, the '199 Publication, and the '671 Publication are disclosed herein, and therefore some similar nomenclature is used herein for clarity and consistency.

Various tools that interface with the expandable implants for insertion and expansion are used. Although considerable effort has been devoted in the art to optimization of such tools, still further improvement would be desirable.

BRIEF SUMMARY OF THE INVENTION

Some aspects of the present invention provide a delivery system for implantation of an implant into an intervertebral space. A delivery system in accordance with such aspects of the invention may include an elongated tool having a distal end removably securable to the implant. A proximal end of the elongated tool may have an attachment interface for detachable securement to a plurality of different modules. Each module may be adapted to effectuate a different function of the delivery system during implantation of the implant.

The different functions of the modules may include: grasping the elongated tool, providing an impaction surface for driving the advancement of the implant, advancing a graft material through the elongated tool into the implant, and actuating the expansion of the implant. For example, one of the modules may be a handle. At least one of the modules may define a flat impaction surface at a proximal end of a handle for driving the advancement of the elongated tool. That flat impaction surface may be defined on a connect cap removably attachable to the handle. Another one of the modules may be a bone graft supply system. The bone graft supply system may include a plunger advanceable in a distal direction to drive graft material distally through the elongated tool and into the implant. The distal advancement of the plunger may be driven by squeezing a trigger of a pistol-grip handle. Another one of the modules may be an expander for actuating the expansion of the implant. The expander may include a fluid delivery system for supplying hydraulic fluid into the implant to expand the implant. The fluid delivery system may include a pressure gauge for displaying the pressure of the hydraulic fluid supplied to the implant. The fluid delivery system may include a plunger advanceable within a fluid reservoir for driving the hydraulic fluid into the implant via a fluid delivery cannula. The fluid reservoir may be oriented transverse to the fluid delivery cannula, such that the plunger is advanceable within the reservoir along a direction transverse to the fluid delivery cannula. The fluid delivery system may include a selector mechanism for switching between two different modes of travel by the plunger. One of the two modes of travel by the plunger may include rotation of the plunger about its longitudinal axis, such that the plunger travels along a threaded connection. Another one of the two modes of travel by the plunger may include sliding the plunger linearly along the longitudinal axis of the plunger. The different modules may be securable to and detachable from the proximal end of the elongated tool by depressing a button on the respective module.

Other aspects of the invention provide a fluid delivery system for removable connection to a hydraulically expandable intervertebral implant. A fluid delivery system in accordance with such aspects of the invention may include a fluid delivery cannula and a plunger having a handle adapted to be grasped by a surgeon or other user. The handle may include a gauge configured to display an indication correlated to the hydraulic pressure supplied to the intervertebral implant via the fluid delivery cannula.

Yet other aspects of the invention provide a tool removably securable to an expandable intervertebral implant. A tool in accordance with such aspects of the invention is configured for supplying a hydraulic fluid into the implant to expand the implant. The tool preferably includes an elongated shaft having a fluid delivery cannula therein. The fluid delivery cannula may have a distal end engageable with the implant such that the distal end is in fluid communication with a port on the implant. At least the distal end of the fluid delivery cannula is desirably a relatively rigid structure. The tool is preferably adapted to induce movement of the fluid delivery cannula in a distal direction relative to the shaft, such that the distal end of the fluid delivery cannula moves into engagement with a lock release within the implant so as to unlock the expansion of the implant and permit the implant to collapse. In accordance with some aspects of the invention, the movement of the fluid delivery cannula in the distal direction relative to the shaft may be induced by a pivotable lever connected to the tool.

Other aspects of the invention provide an expandable intervertebral implant. An implant in accordance with such aspects of the invention preferably include a housing and a top plate movable away from the housing so as to expand the implant. The housing may include a side surface extending transverse to the top plate along a height dimension of the implant. The side surface may have an opening therein, which opening may communicate with an interior cavity of the implant so as to permit a graft material to be supplied into the interior cavity via the opening. The housing may also include a ramp extending between the opening and the interior cavity. The ramp is preferably oriented at an oblique angle to the side surface of the housing, so as to direct the graft material to a particular location of the interior cavity along the height dimension of the implant. A spinal implant system in accordance with yet further aspects of the invention may include such an expandable intervertebral implant and may further include a reamer having a flexible shaft. The shaft of such reamer is preferably adapted to be received through the opening in the side surface of the implant and along the ramp into the interior cavity of the implant. Desirably, such reamer may be used to clear graft blockages during backfilling of the implant.

Still other aspects of the invention provide a block for supporting an intervertebral implant while packing an interior cavity of the implant with graft material. A block in accordance with such aspects of the invention may include a base and a projection extending from the base. The projection is desirably sized to be received through a first opening in the implant such that the projection is positioned at least partially within the interior cavity of the implant. A spinal implant system in accordance with yet further aspects of the invention may include such a block and may further include an intervertebral implant. Such implant desirably includes a second opening on an opposite side of the implant from the first opening. When the implant is supported on the block with the projection received through the first opening in the implant, the second opening is preferably oriented upwardly so as to receive a supply of graft material into the interior cavity through the second opening. The projection of the block is desirably configured to closely fit within the interior cavity of the implant, such that graft material positioned within the interior cavity is prevented from flowing downwardly past an upper surface of the projection into a portion of the interior cavity occupied by the projection. In accordance with some aspects of the invention, the block may include a retaining mechanism configured to move into engagement with the implant to secure the implant to the block.

DETAILED DESCRIPTION

Figure 1:
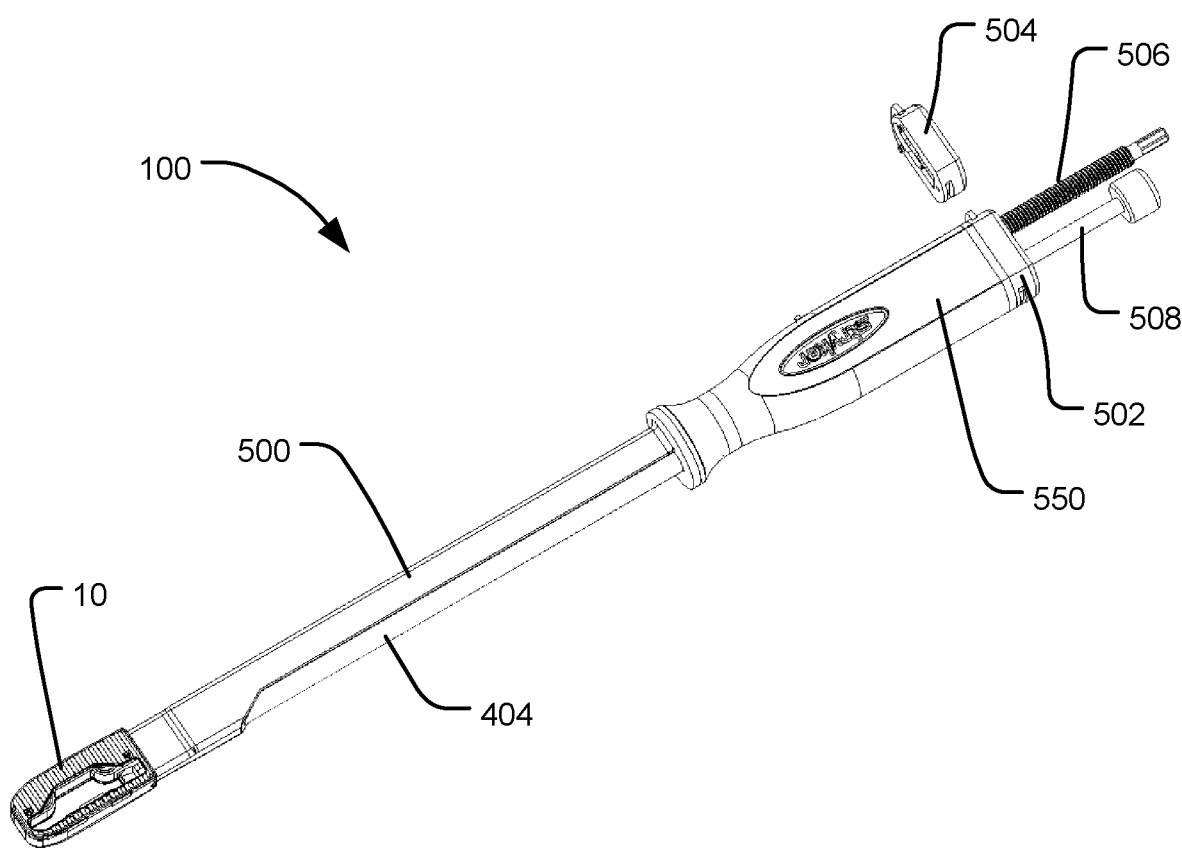
FIG. 1 is a perspective view of an implant delivery system in accordance with one embodiment of the present invention connected to an expandable implant.

FIG. 1 illustrates an embodiment of an implant delivery system for insertion of an expandable implant 10 into an intervertebral space in accordance with the present invention. The expandable implant 10 may, for example, be structured like any of the embodiments of expandable implants disclosed in the '199 Publication. A delivery tool 100 of the delivery system is comprised of a handle 550 connected to an insertion shaft 500. The handle 550 is adapted to be grasped by a surgeon or other user while the expandable implant 10 is inserted into the intervertebral space using the delivery tool 100, and the handle 550 includes features at its proximal end to facilitate engagement with, and control of, the expandable implant 10. The expandable implant 10 is connectable to the distal end of the insertion shaft 500. Various connect caps of the delivery system can be fitted to the proximal end of the handle 550 via a connection mechanism that allows for connect caps to be interchanged. Each connect cap serves a different purpose during implantation of the expandable implant 10 and can be readily switched without disconnecting the delivery tool 100 from the implant 10 and without removing the implant 10 from the intervertebral space.

Connect cap 502 allows for the advancement of plunger 506 for the fluid delivery system and plunger 508 for the bone graft supply line 404. Connect cap 504 provides for a durable impaction surface during insertion of the expandable implant 10. Both connect cap 502 and connect cap 504 have a button 503 that facilitates the attachment and removal of connect caps 502 and 504. The delivery tool 100 also has a flip lever 510 that allows for unlocking and collapsing the expandable implant 10.

Figure 2:
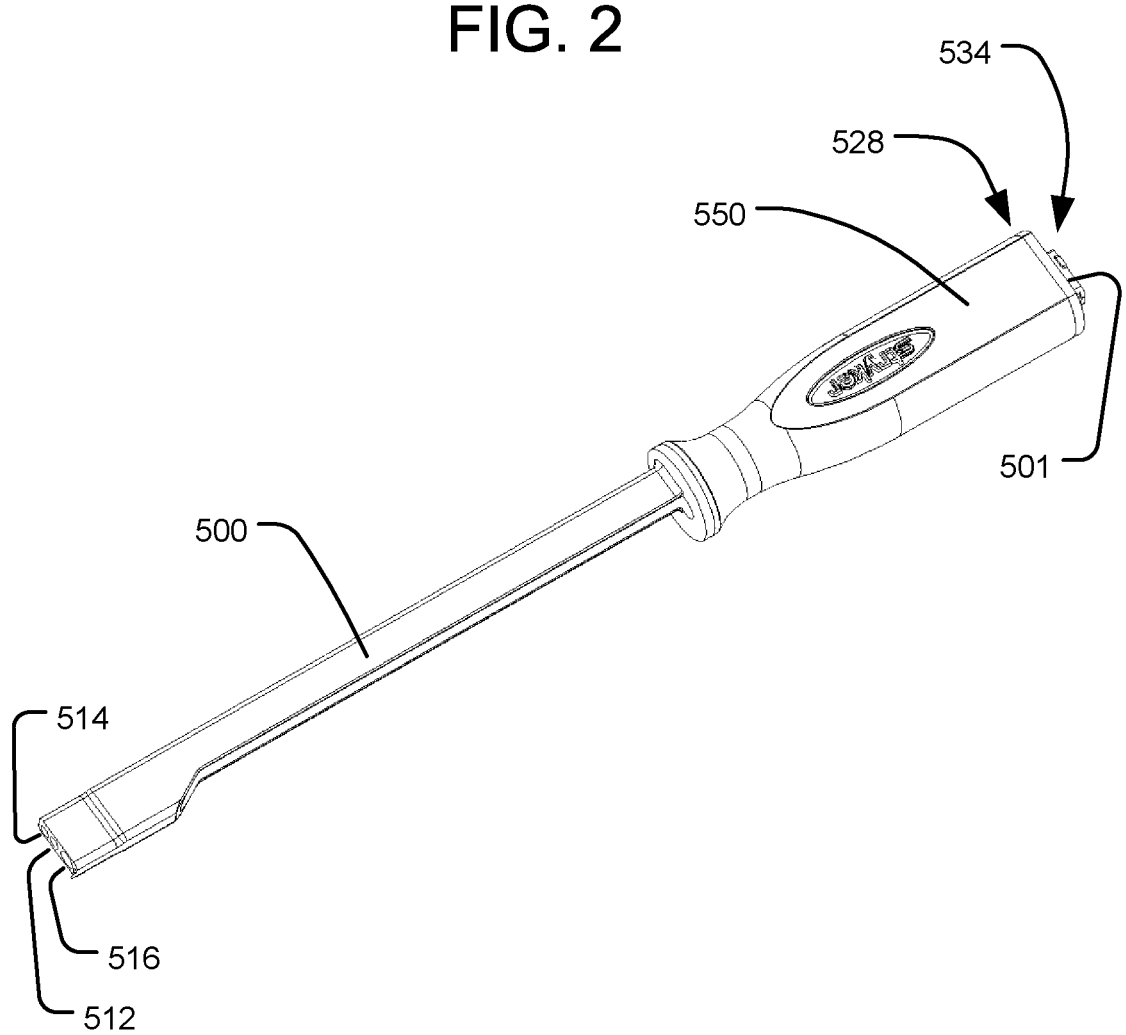
FIG. 2 is a perspective view of a delivery tool of the implant delivery system of FIG. 1.
Figure 3:
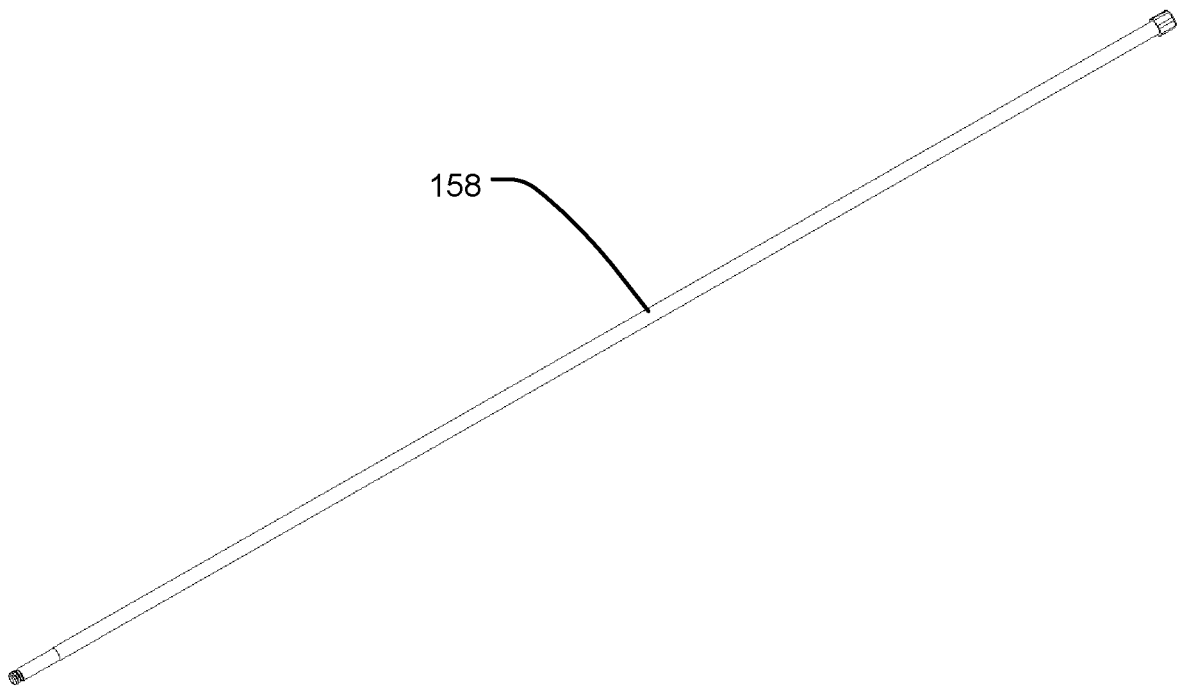
FIG. 3 is a perspective view of a rotatable threaded member.
Figure 4:
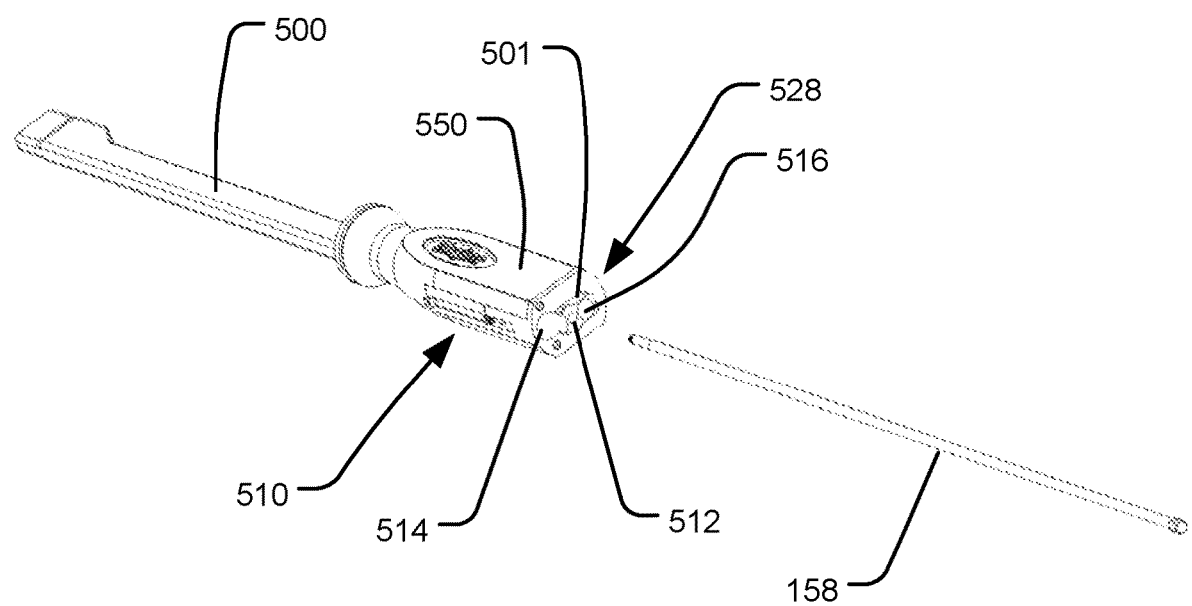
FIG. 4 is a perspective view of the insertion of the rotatable threaded member into the delivery tool.
Figure 5:
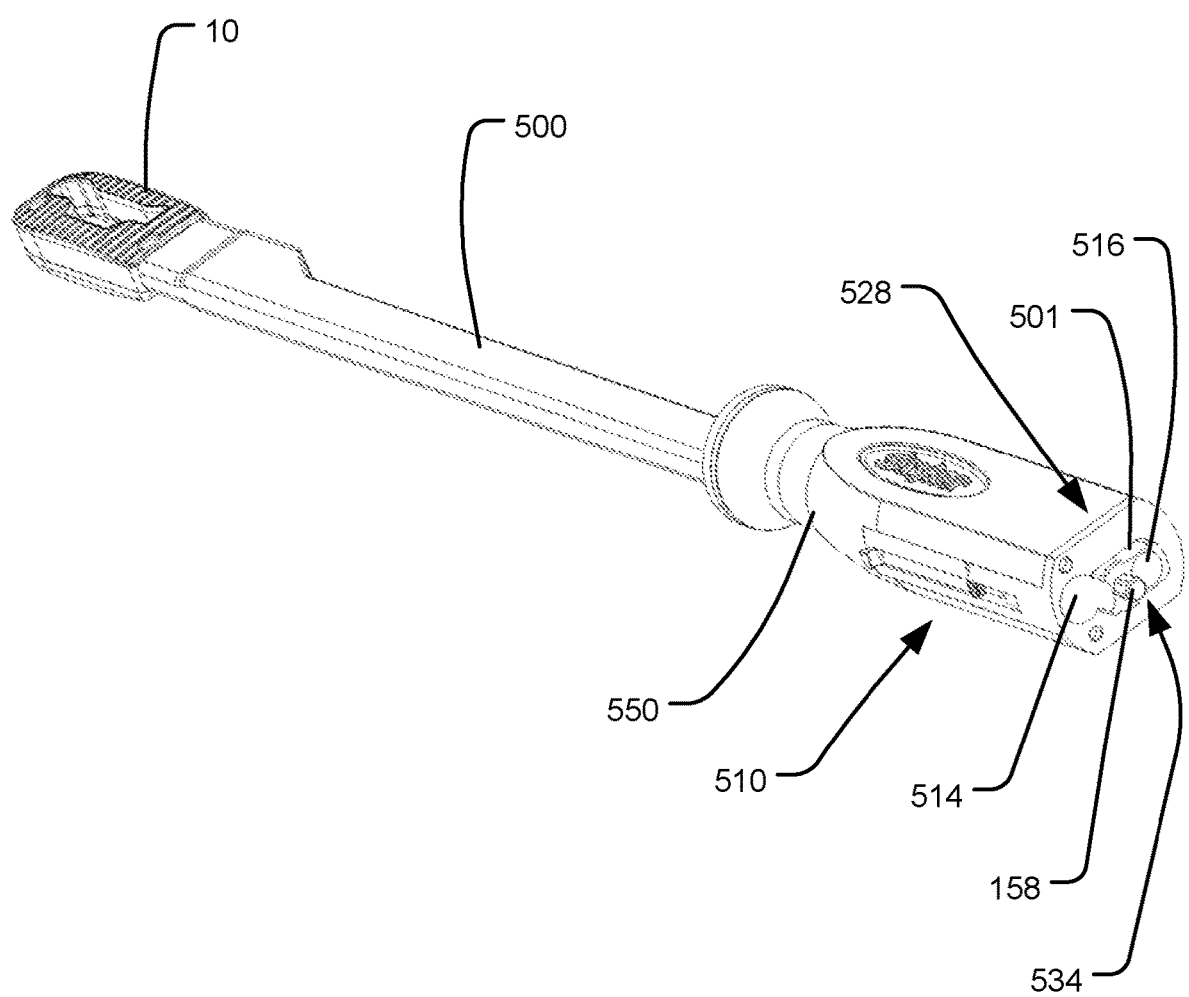
FIG. 5 is a perspective view of the rotatable threaded member inserted into the delivery tool connected to an expandable implant.

FIGS. 2-5 illustrate the insertion of rotatable threaded member 158. FIG. 2 illustrates the delivery tool 100 having a receptacle 512 for receiving a rotatable threaded member 158, a receptacle 514 for the fluid delivery cannula 154, and a receptacle 516 for the bone graft supply line 404. The receptacle 512 for receiving the rotatable threaded member 158 extends from the proximal end of the handle 500 through the distal end of the insertion shaft 500. The distal end of the rotatable threaded member 158, as illustrated in FIG. 3, is inserted into the proximal end of receptacle 512, as illustrated in FIG. 4. The distal end of the rotatable threaded member 158 extends out of the distal end of the insertion shaft 500 and connects with the proximal end of the expandable implant 10, as illustrated in FIG. 5, in order to secure the implant 10 to the delivery tool 100. Specifically, the expandable implant 10 is secured to the delivery tool 100 by threading the threaded distal end of the rotatable threaded member 158 into a delivery tool anchor in the form of a threaded receptacle on the proximal end of the expandable implant 10, as disclosed in the '199 Publication. When connecting the rotatable threaded member 158 to the expandable implant 10, connect cap 502 or 504 need not be attached to the handle 550 of the delivery tool 100.

Receptacle 514 is for receiving the fluid delivery cannula 154 of a fluid delivery system. The fluid delivery cannula 154 allows for hydraulic fluid to be delivered to expandable implant 10 to expand expandable implant 10. Beneficially, by receiving the hydraulic fluid delivery components within the handle 550 and insertion shaft 500 (e.g., in receptacle 514), the delivery tool 100 may be easier to manipulate than some delivery tools, which may include bulky external syringes for supplying hydraulic fluid.

Figure 6:
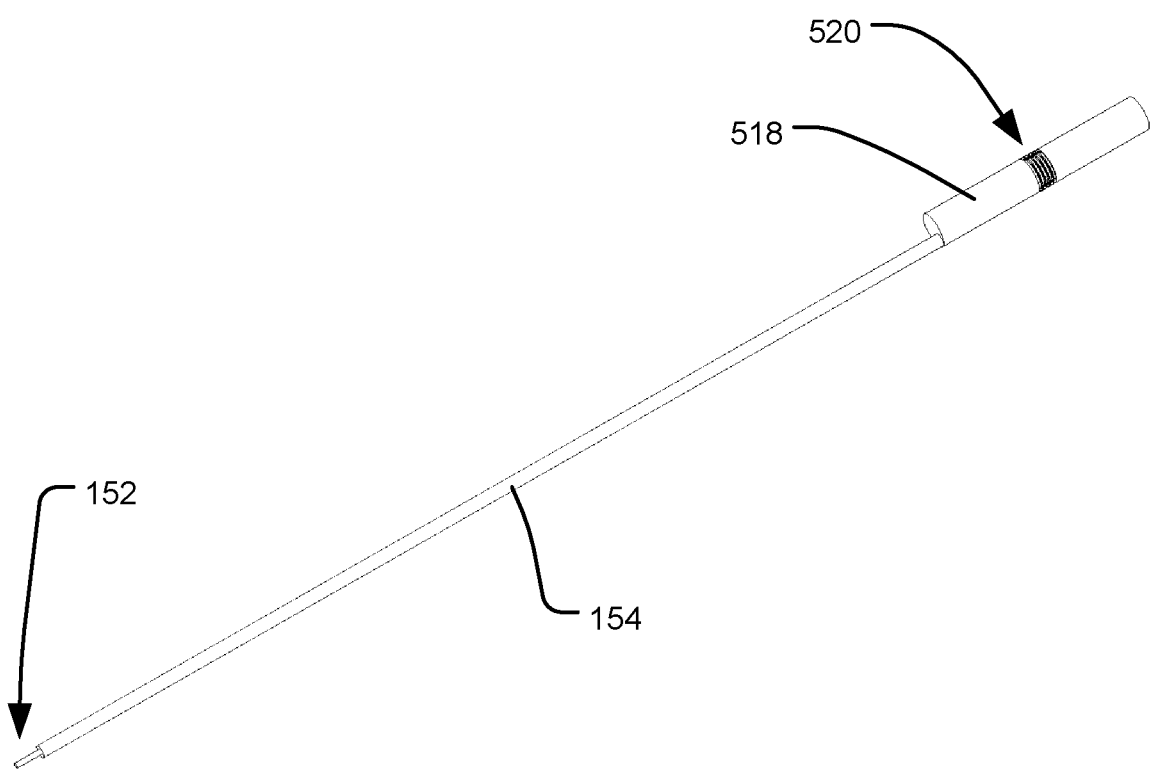
FIG. 6 is a perspective view of a fluid delivery cannula.
Figure 7A:
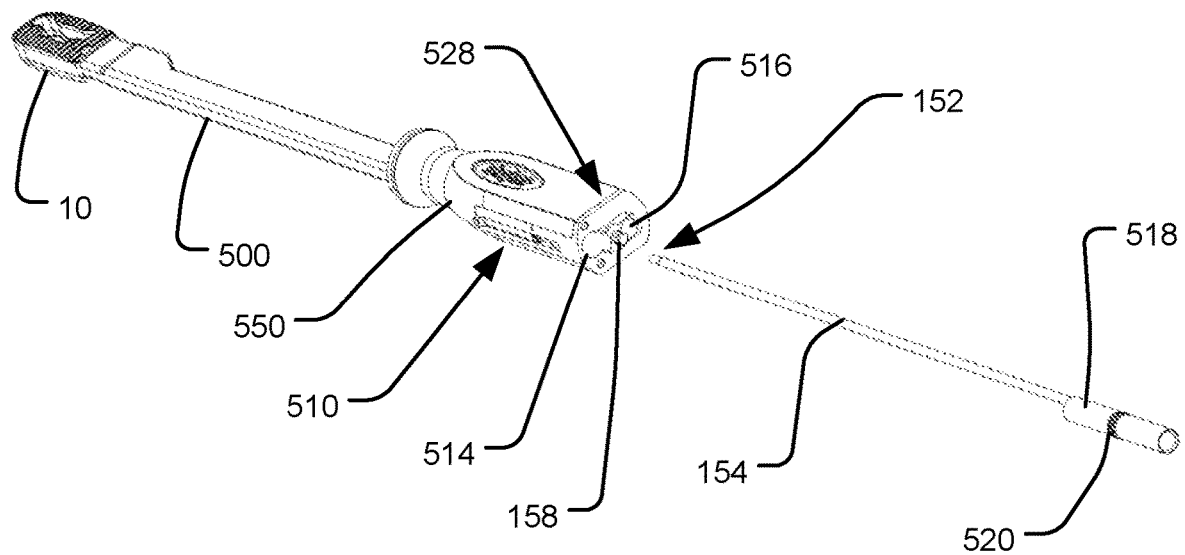
FIG. 7A is a perspective view of the insertion of the fluid delivery cannula into the delivery tool.
Figure 7B:
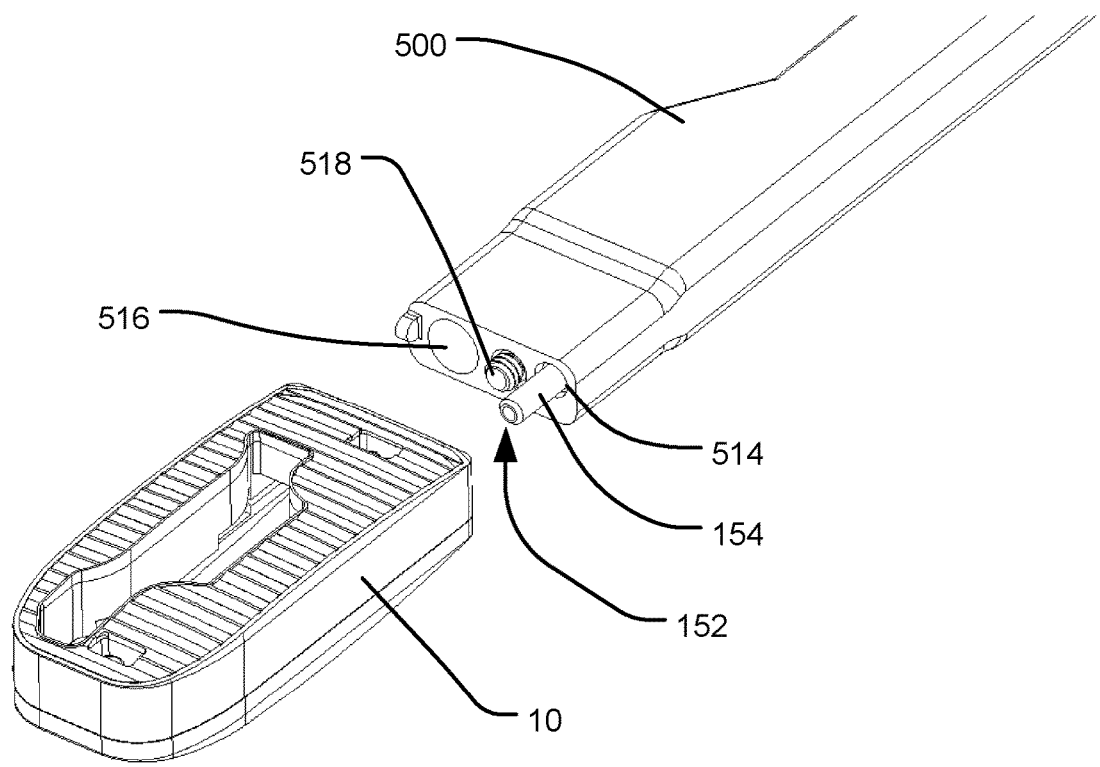
FIG. 7B is a perspective view of the distal end of the delivery tool with the fluid delivery cannula inserted and projecting distally towards the expandable implant.
Figure 15A:
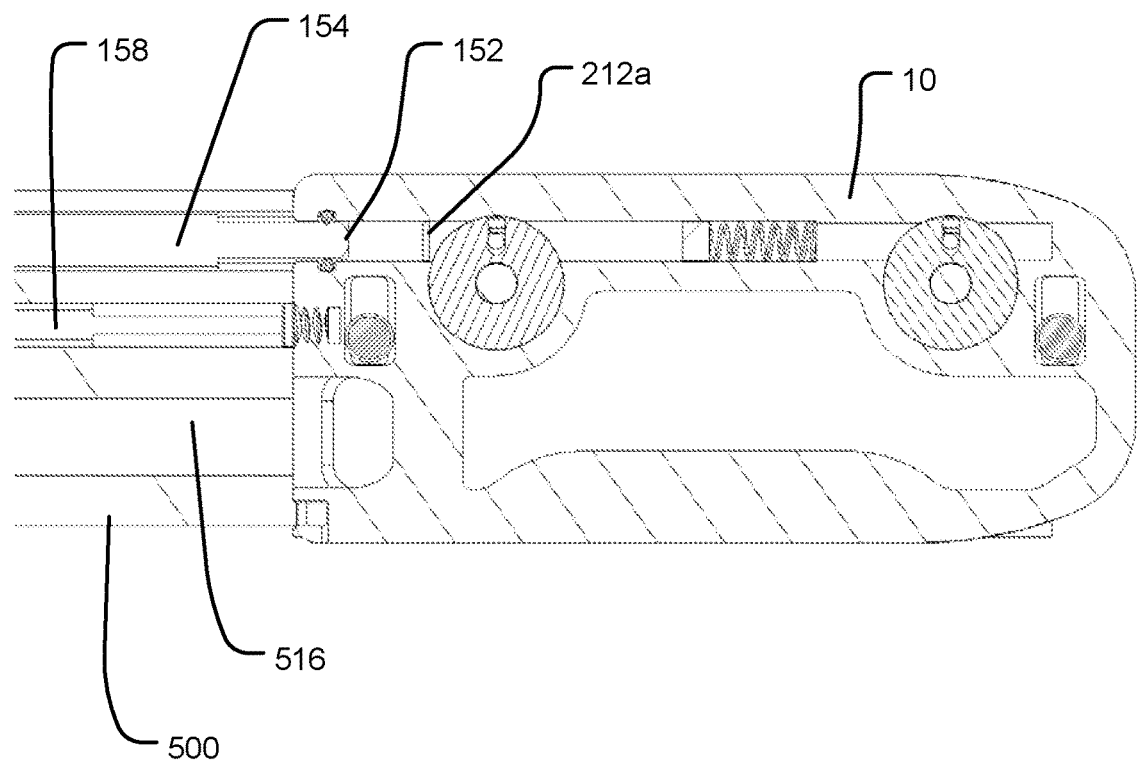
FIGS. 15A, 15C and 15D are top, cross-sectional views of the delivery tool connected to the expandable implant, showing the movement of the fluid delivery cannula by a flip lever of the delivery tool.

As illustrated in FIG. 6, fluid delivery cannula 154 includes a reservoir 518 at the proximal end of the fluid delivery cannula 154 and an outlet 152 for delivering pressurized fluid at the distal end of the fluid delivery cannula 154. The reservoir 518 has a rack mechanism 520 along its periphery that will interact with a pinion mechanism 522 at one end of flip lever 510, as shown in FIG. 15C (and discussed below). Outlet 152 for delivering pressurized fluid is inserted into receptacle 514 for the fluid delivery cannula at the proximal end of the handle 550, as illustrated in FIG. 7A. After the fluid delivery cannula 154 is seated in the handle 550 and insertion shaft 500, the outlet 152 for delivering pressurized fluid will be located at the distal end of the insertion shaft 500, where it can fluidly communicate with the inlet of a pressure channel on the proximal end of the expandable implant 10. As shown in FIGS. 15A and 7B, the outlet 152 may project from the distal end of the insertion shaft 500, such that it is partially received within the inlet of the expandable implant, where it can form a sealing connection by engaging an o-ring positioned within the pressure channel of the implant 10, as disclosed in the '199 Publication.

Figure 8:
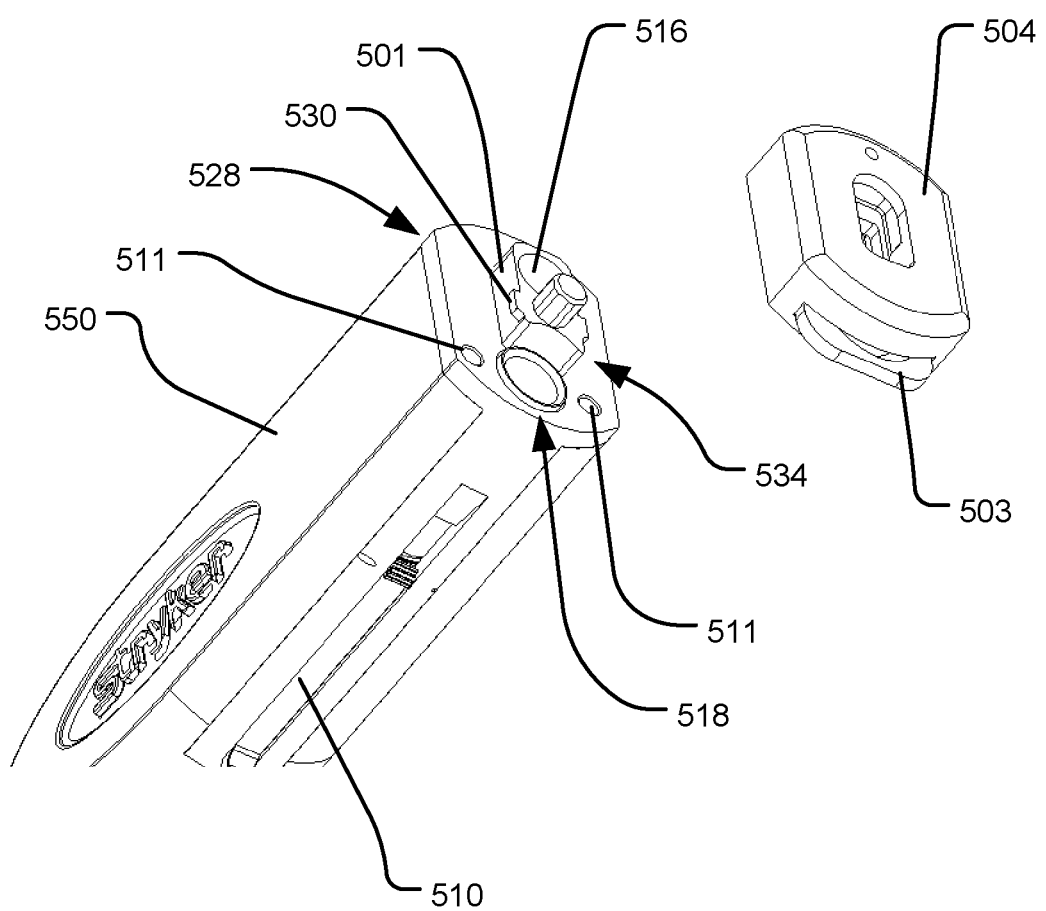
FIG. 8 is a perspective view of the attachment of a connect cap for impaction to the handle of the delivery tool.

FIGS. 8-11B illustrate how connect cap 504 attaches to the proximal end of handle 550 of delivery tool 100. Preparation for attachment of connect cap 504 to handle 550 is illustrated in FIG. 8. Connect cap 504 provides for a flat surface on its proximal end to provide a durable impaction surface to help insert or place expandable implant 10.

Connect cap 504 can be interchanged with connect cap 502 and connect cap 702 at various points during the use of the delivery tool 100. Connect cap 502 provides for plunger 506 and plunger 508 to be used in conjunction with the delivery tool 100. Connect cap 702 provides a pistol-grip handle 700 that can be used to back-fill interior cavity 15 of expandable implant 10 with graft material.

Figure 9:
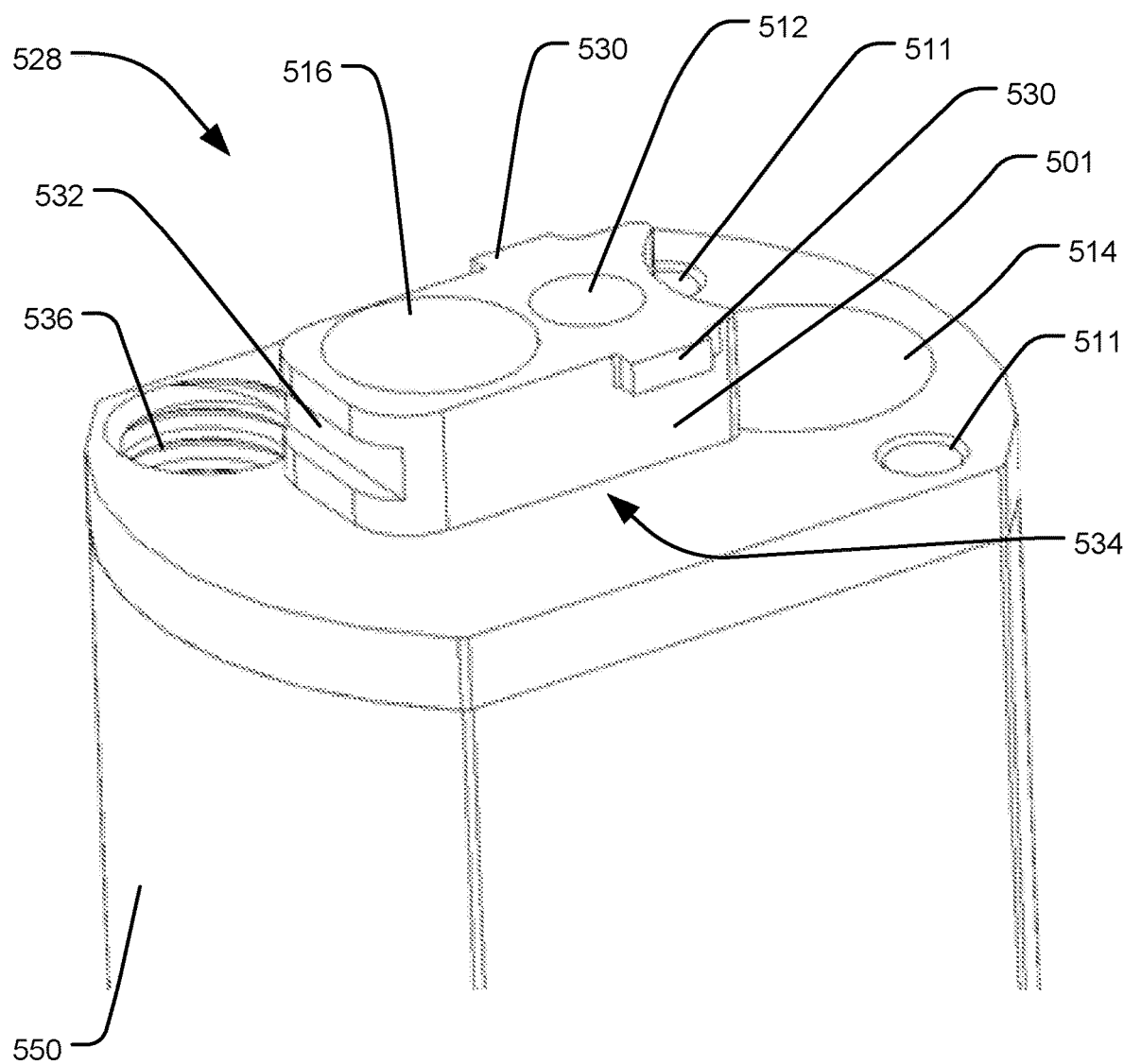
FIG. 9 is a perspective view of the proximal end of the handle of the delivery tool.

FIG. 9 illustrates an attachment interface 528 at the proximal end of the handle 550 to which the connect cap 504 will be attached. The attachment interface 528 includes two recesses 511 to allow for alignment between handle 550 and connect cap 504, by receiving corresponding projections 505 of the connect cap 504, as discussed below. The attachment interface 528 also includes a locking mechanism 534 for keeping the connect cap 504 securely attached to the attachment interface 528. The locking mechanism 534 includes a projection 501 having a recess 532 and one or more (e.g., two) overhead projections 530. Although not illustrated in the other figures, the proximal end of the handle 550 may also include a connection 536 (e.g., a threaded bore) for securely and removably connecting to a slap hammer to assist with removal of the delivery tool 100 and implant 10 in the proximal direction if the implant 10 becomes stuck in the intervertebral space.

Figure 10:
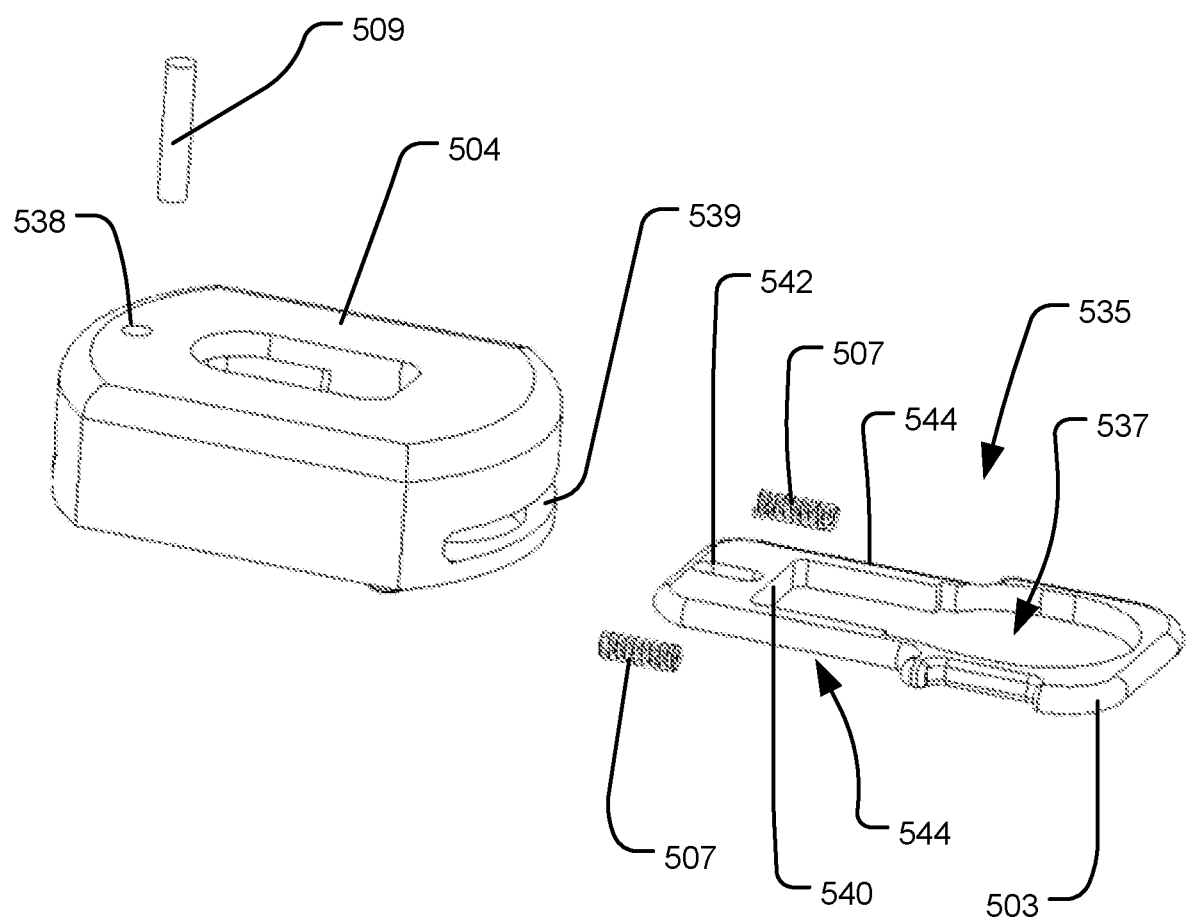
FIG. 10 is an exploded view of the connect cap of FIG. 8.

As illustrated in FIG. 10, connect cap 504 is comprised of a sliding lock mechanism 535 having a central hole 537 in it that is shaped to receive the projection 501 on the proximal end of handle 550. The sliding lock mechanism 535 is spring-biased, using springs 507. A stop pin 509 is received through a slot 542 in the sliding lock mechanism 535 to constrain the travel of the sliding lock mechanism 535, such that the sliding lock mechanism 535 is retained within the connect cap 504. The sliding lock mechanism 535 includes an outwardly projecting button 503, which may be a projecting portion of the sliding lock mechanism 535 projecting out of slot 539 on connect cap 504.

Figure 11A:
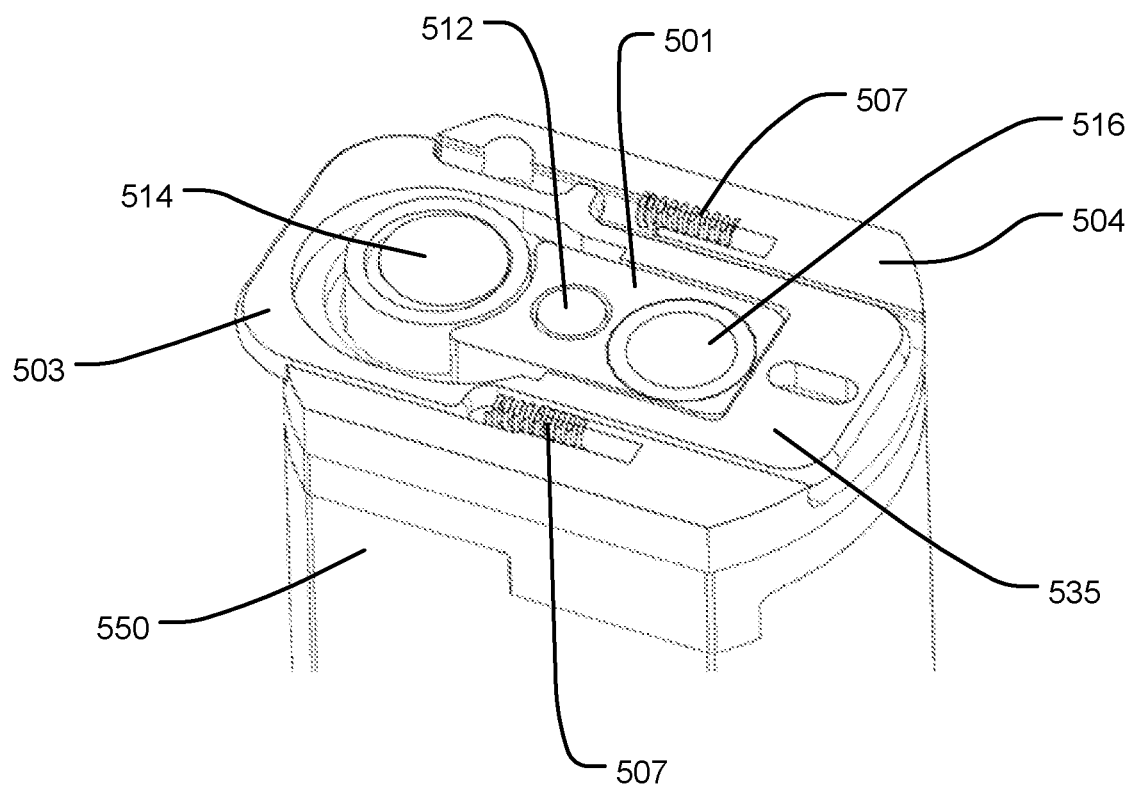
FIG. 11A is a perspective, cross-sectional view showing a sliding lock mechanism within the connect cap of FIG. 8.
Figure 11B:
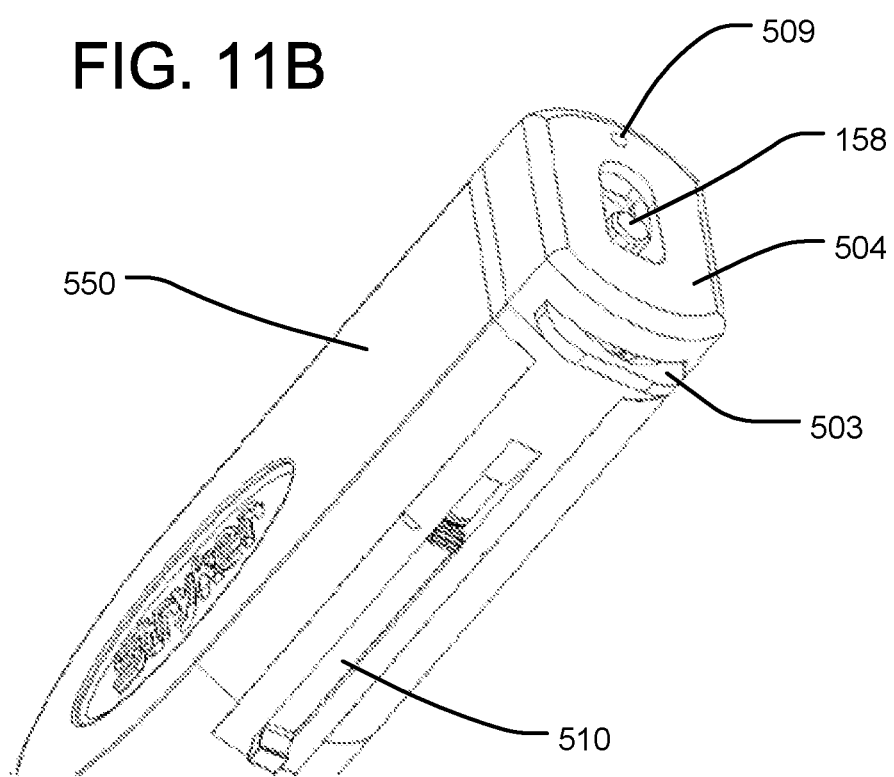
FIG. 11B is a perspective view of the connect cap of FIG. 8 connected to the proximal end of the handle of the delivery tool.

The sliding lock mechanism 535 allows for connect cap 504 to be locked to the locking mechanism 534 of the handle 550. Specifically, when connect cap 504 is being attached to the proximal end of handle 550, as illustrated in FIGS. 11A-11B, button 503 is pressed, causing springs 507 to compress, so that the central hole 537 becomes aligned with projection 501. Projections 505 on the distal end of connect cap 504 align with recesses 511 on the proximal end of handle 550. Once connect cap 504 is aligned and seated on the attachment interface 528 at the proximal end of handle 550, button 503 is released, causing springs 507 to de-compress and lock the locking mechanism 534 into place. Specifically, when the button 503 is released, the sliding lock mechanism 535 slides such that stop pin 509 slides within slot 542, the end 540 of central opening 537 slides into the recess 532 of projection 501, and the side peripheral edges 544 of the sliding lock mechanism 535 slide under the overhead projections 530. The inter-engagement of all those structures discussed above prevents the connect cap 504 from becoming disconnected from handle 550 when the button 503 is in its undepressed position.

Removal of connect cap 504 is done through a similar process as attaching connect cap 504. That is, to remove connect cap 504, button 503 is pressed, causing springs 507 to compress. This shifts sliding lock mechanism 535 such that it is no longer locked into place by the overhead projections 530 on projection 501 or by the recess 532 in projection 501. Once button 503 is pressed, connect cap 504 can be lifted off handle 550.

The connect cap 502 may have substantially the same attachment structure as the connect cap 504, and therefore attaching and removing connect cap 502 may use the same process as connect cap 504, as described above.

The structure of connect cap 502 allows for either or both of plunger 506 or plunger 508 to be received through or removed from the connect cap 502 during the use of the delivery tool 100. There are multiple receptacles in the connect cap 502. Receptacle 524 is threaded to receive the plunger 506 of the fluid delivery system, which is used to push the hydraulic fluid into the expandable implant 10.

Receptacle 526 receives plunger 508 that is used to push graft material in order to back-fill the expandable implant 10 after it has been expanded.

Figure 12:
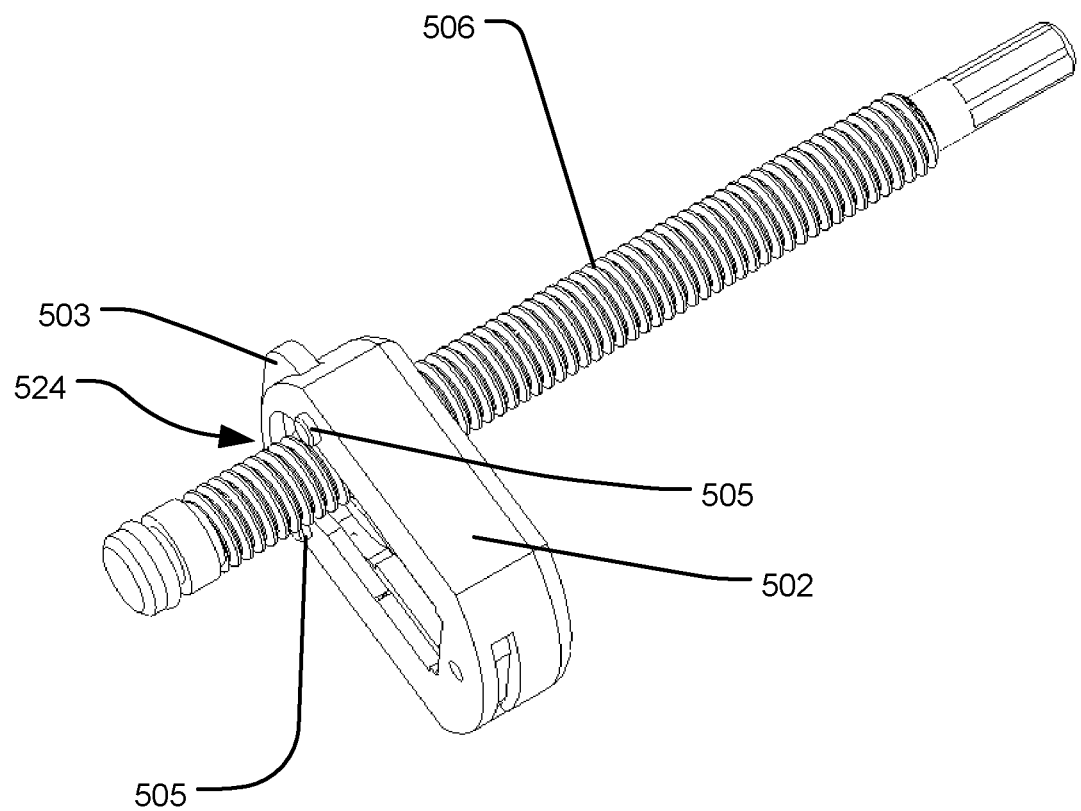
FIG. 12 is a perspective view of a different connect cap with a plunger for the fluid delivery cannula.
Figure 13:
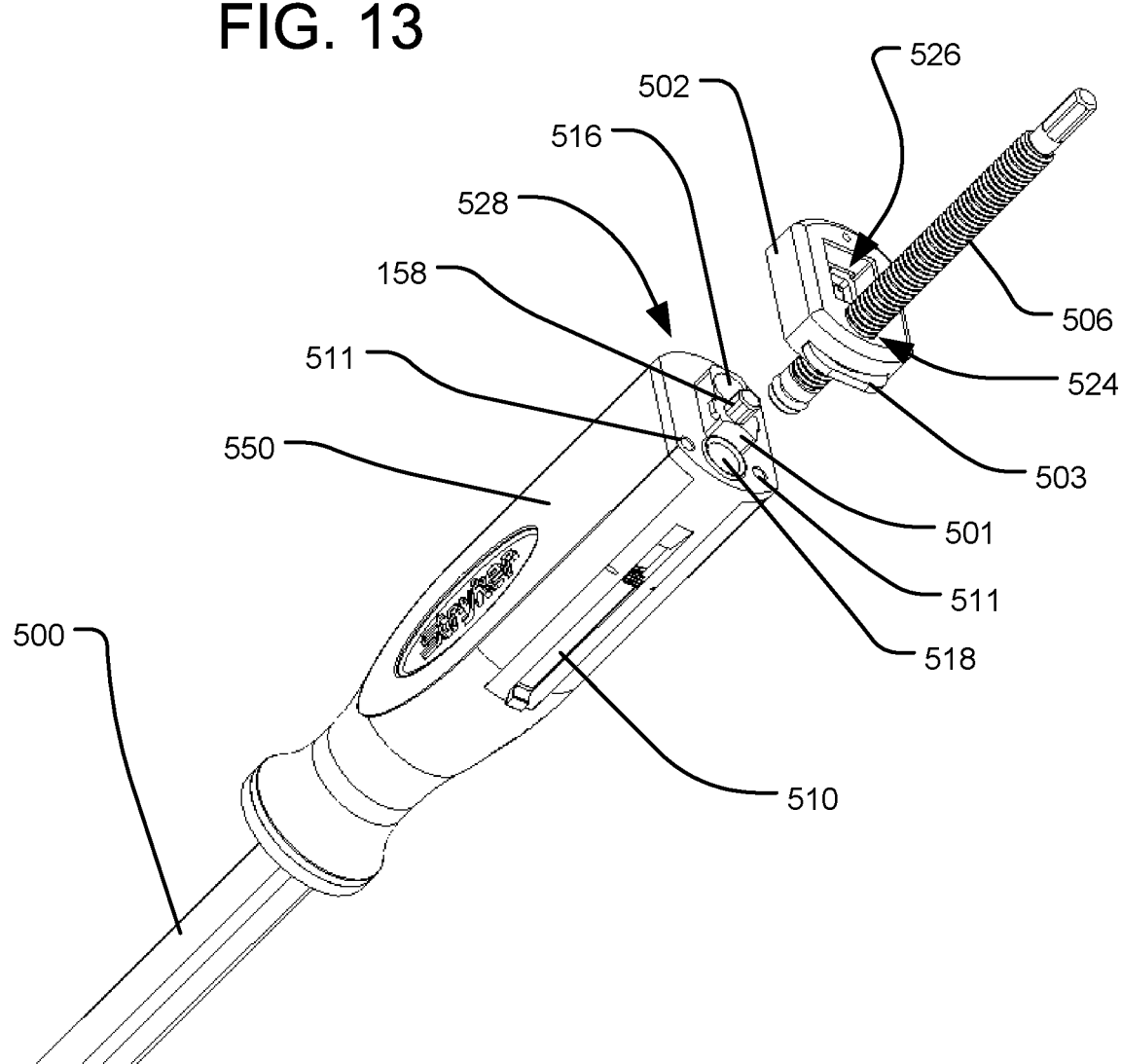
FIG. 13 is a perspective view of the attachment of the connect cap and plunger of FIG. 12 to the handle of the delivery tool.

The distal end of plunger 506 is inserted into receptacle 524 on connect cap 502, as seen in FIG. 12. Receptacle 524 is threaded to match the threading of plunger 506. FIG. 13 illustrates how connect cap 502 can be attached to the proximal end of the handle 550 of the delivery tool 100 after having already received plunger 506.

Figure 14:
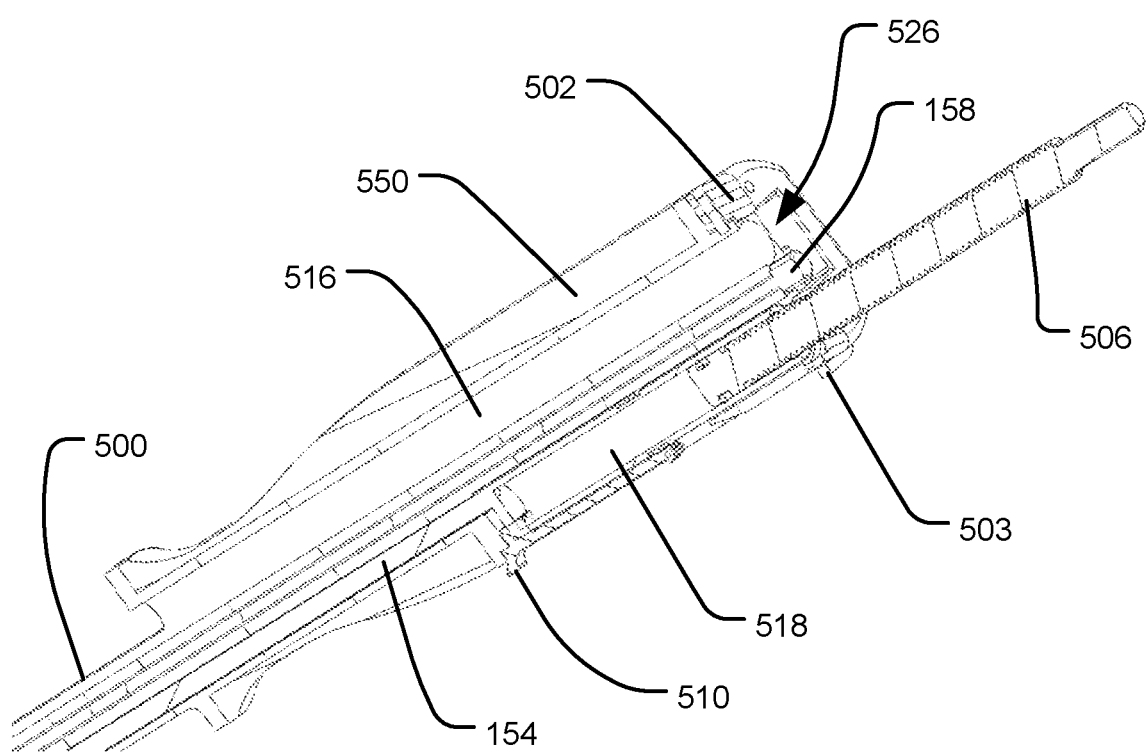
FIG. 14 is a perspective, cross-sectional view of the connect cap and plunger of FIG. 12 attached to the proximal end of the handle of the delivery tool.

FIG. 14 illustrates how connect cap 502 with plunger 506 align and function with all the other elements of handle 550. Plunger 506 is seated within reservoir 518. Threadedly advancing the plunger 506 pushes the hydraulic fluid through fluid delivery cannula 154 and out the outlet 152, which is in fluid communication with the inlet of a pressure channel of the expandable implant 10.

Figure 16A:
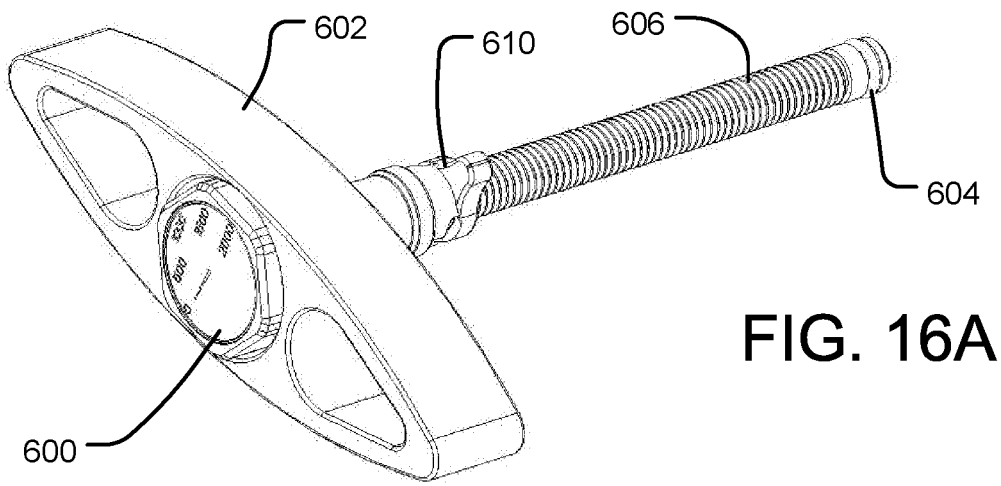
FIG. 16A is a perspective view of an alternative embodiment of a plunger containing a pressure gauge for the fluid delivery cannula.
Figure 16B:
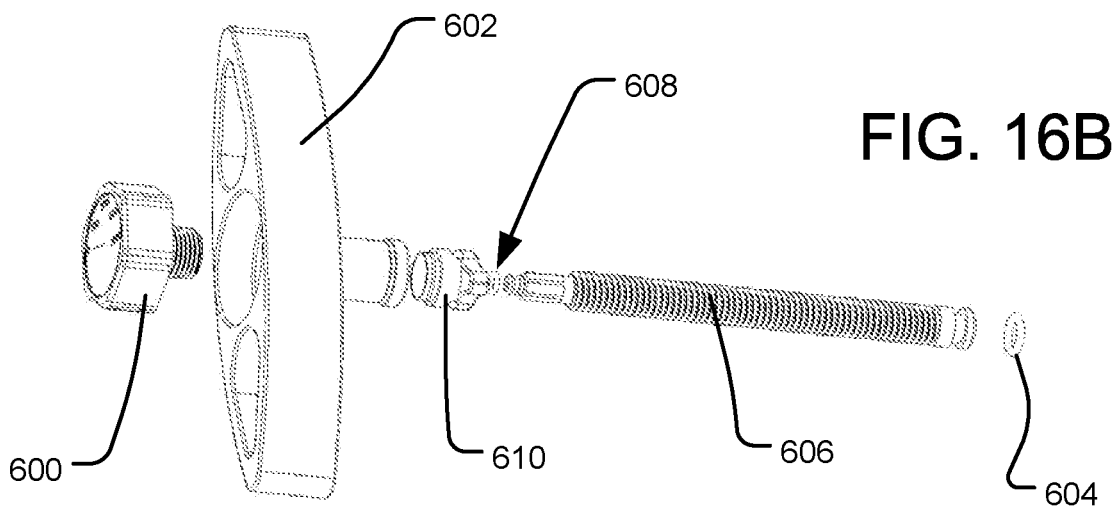
FIG. 16B is an exploded view of the plunger of FIG. 16A.
Figure 16C:
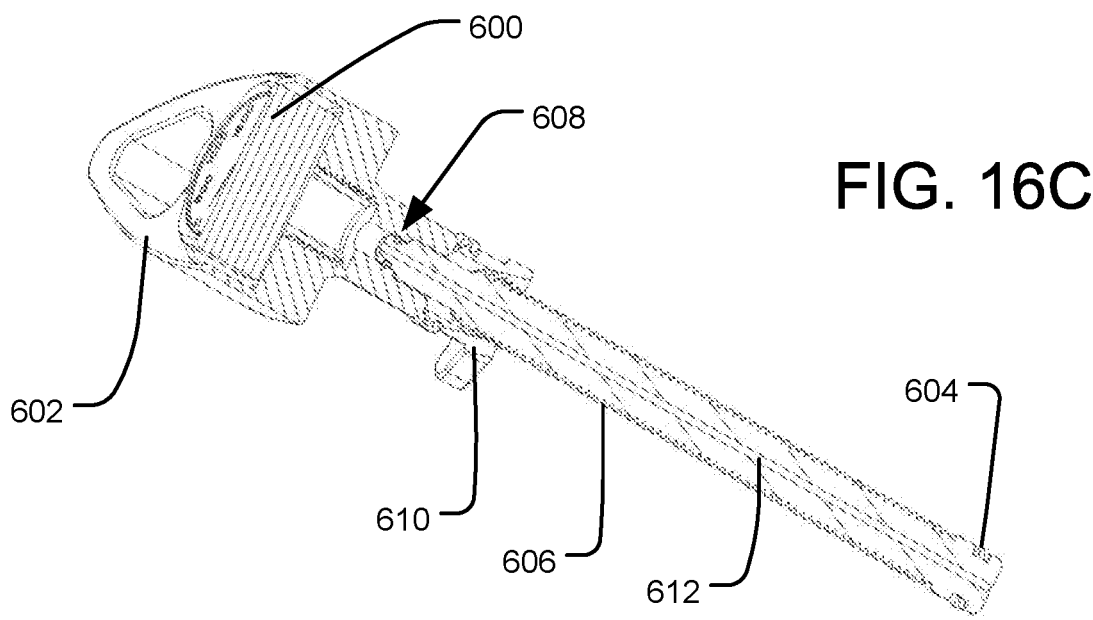
FIG. 16C is a cross-sectional view of the plunger of FIG. 16A.

Plunger 506 for the fluid delivery cannula 154 has a structure on the proximal end that allows for a variety of handles to be attached for turning plunger 506. FIGS. 16A-16C are exemplary of the shape of what the handle may look like. FIGS. 16A-16C illustrate the handle 602 with a pressure gauge 600 embedded in the handle. Another embodiment of handle 602 may be without such a recess or a pressure gauge embedded within it.

Plunger 506 can be operated by turning an attached handle. As the handle is turned, plunger 506 pushes hydraulic fluid from reservoir 518 through the fluid delivery cannula 154 and out the outlet 152 into the expandable implant 10 causing expandable implant 10 to expand.

In an alternative embodiment, as illustrated in FIGS. 31A-31E, connect cap 502 may be replaced with connect cap 1002, which includes a selector mechanism 1004 for selecting between two modes of travel by the plunger 1006 that pushes the hydraulic fluid into the implant 10. In one mode, the plunger 1006 may be threadedly engaged within a receptacle 1024 in the connect cap 1002 so that the plunger 1006 can travel (i.e., be advanced or retracted) by rotation about its longitudinal axis, similar to plunger 506. In another mode, the threads may be disengaged from the plunger 1006 so that the plunger can travel by sliding it linearly through the receptacle 1024. The process of attaching and removing connect cap 1002 is the same process as attaching and removing connect caps 502 and 504. That is, the connect cap 1002 may have a sliding lock mechanism 1035 constrained by a stop pin 1009 in the same manner as the sliding lock mechanism 535 and stop pin 509 of connect caps 502 and 504.

Figure 31A:
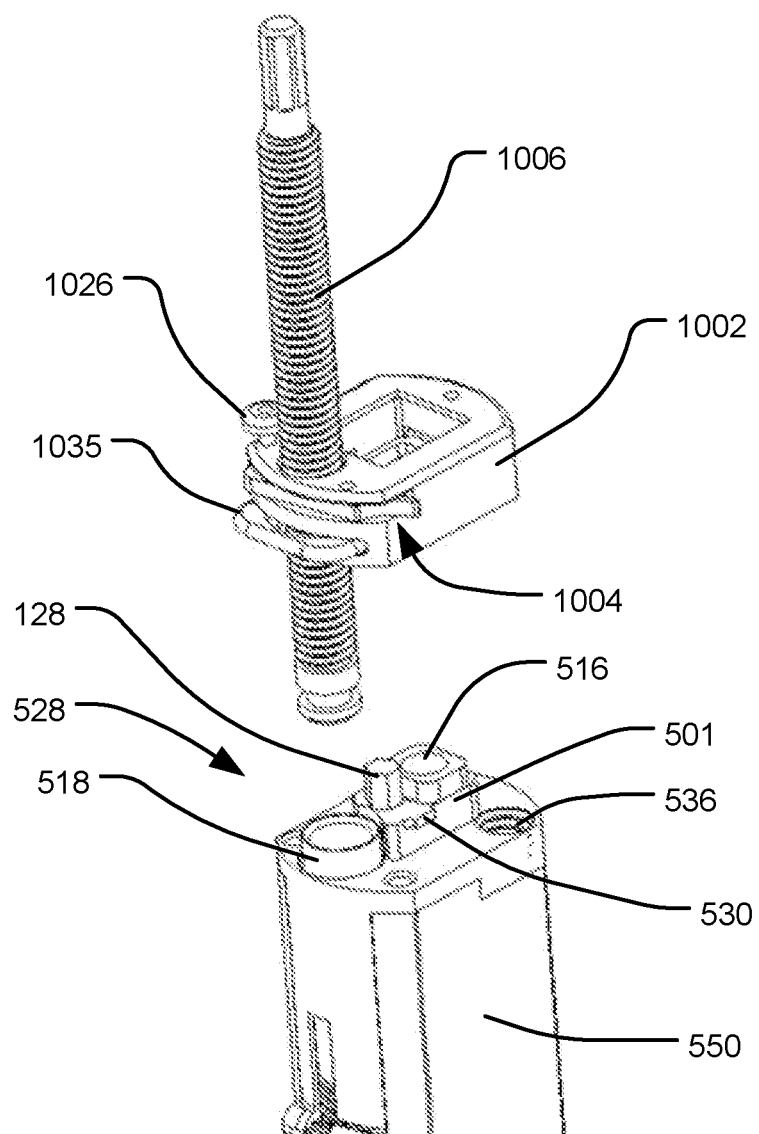
FIG. 31A is a perspective view of the attachment to the handle of the delivery tool of a connect cap with a fluid delivery plunger having two modes of travel.
Figure 31B:
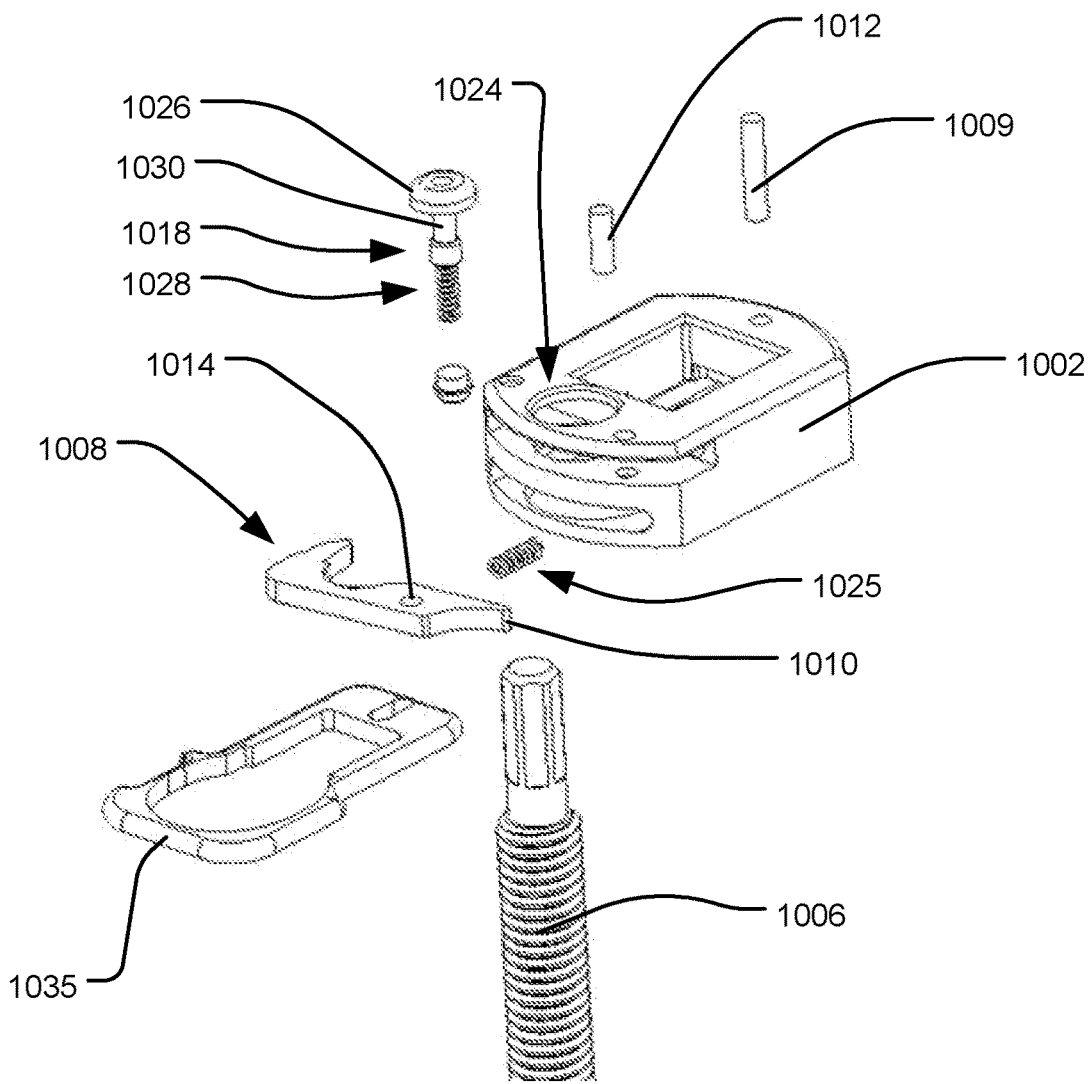
FIG. 31B is an exploded view of the connect cap of FIG. 31A.
Figure 31C:
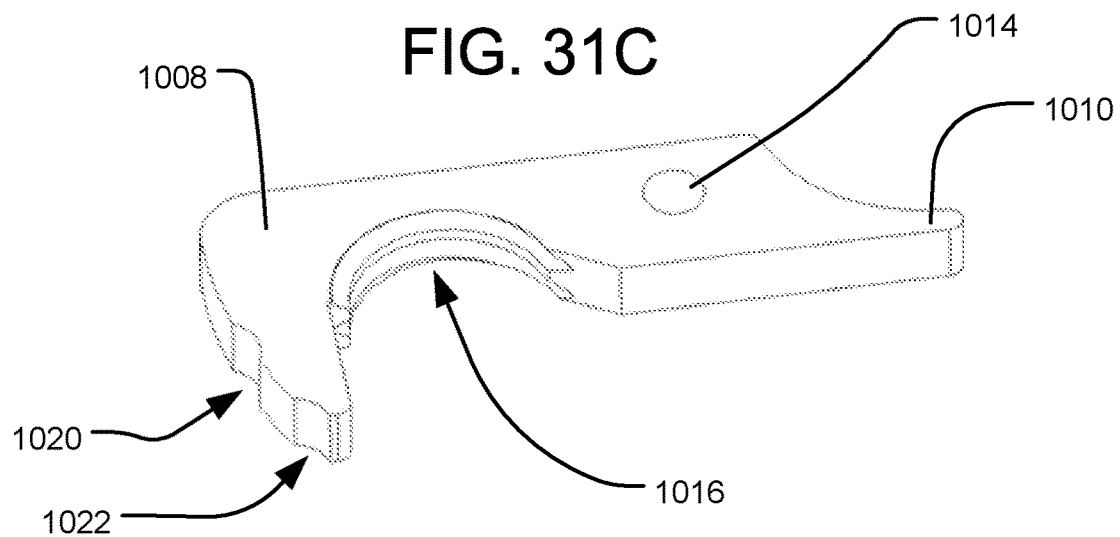
FIG. 31C is a perspective view of a lever of a selector mechanism of the connect cap of FIG. 31A.
Figure 31D:
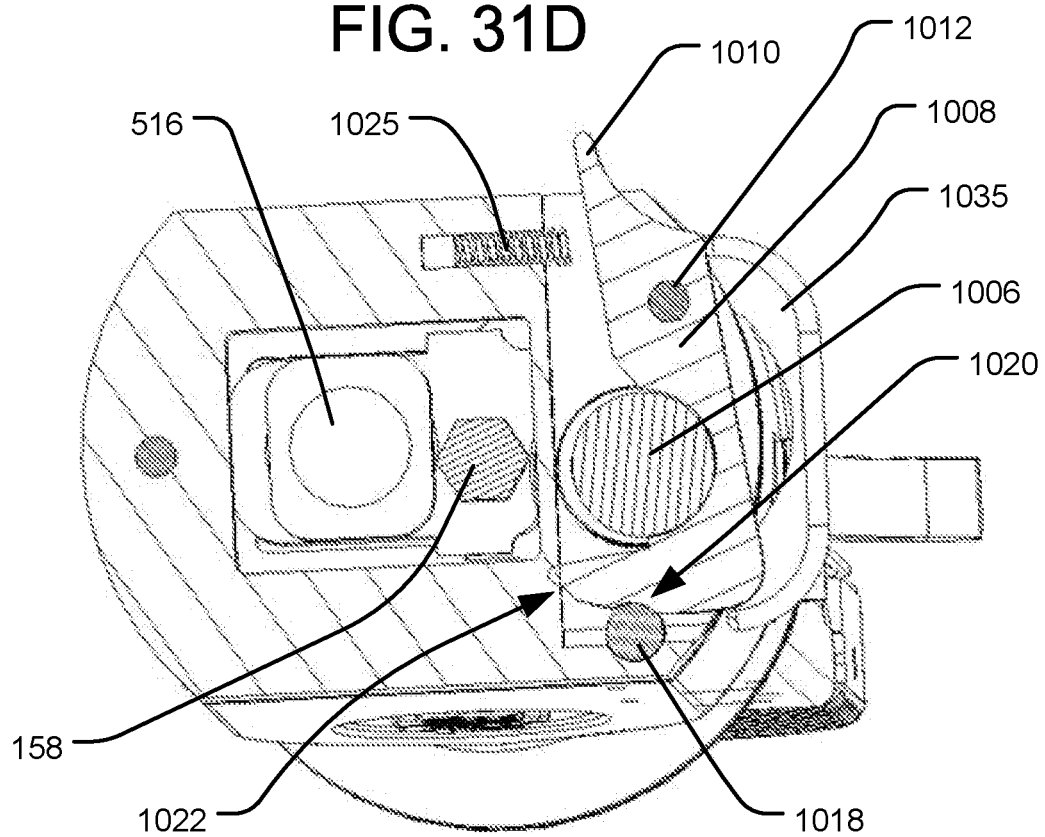
FIG. 31D is a cross-sectional view of the selector mechanism of the connect cap of FIG. 31A in an engaged position.
Figure 31E:
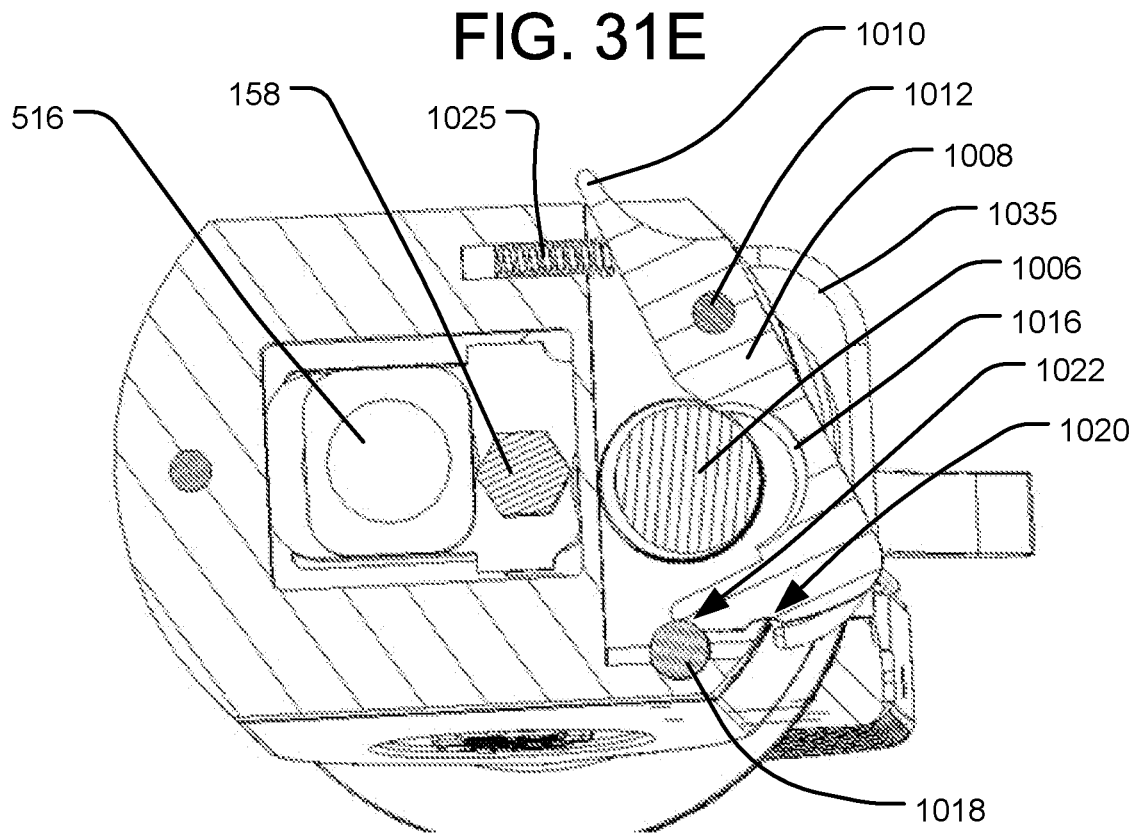
FIG. 31E is a cross-sectional view of the selector mechanism of the connect cap of FIG. 31A in a disengaged position.

The selector mechanism 1004 for selecting between the two modes of travel may include a pivotable lever 1008 controllable by manipulating an external projection 1010 such that the lever 1008 pivots about a pivot pin 1012 received through a hole 1014 in the lever 1008. Such pivoting of the lever 1008 may selectively bring threads 1016 on the lever 1008 into engagement with threads on the plunger 1006, as shown in FIG. 31D, or it may disengage the threads 1016 of the lever 1008 from the threads of the plunger 1006, as shown in FIG. 31E. The lever 1008 can be held in the engaged and disengaged positions by a pin 1018 that engages respective notches 1020 and 1022 formed on the lever 1008. Thus, by pressing on the projection 1010 when the lever 1008 is in the engaged position shown in FIG. 31D (in which the pin 1018 is received by notch 1020), the lever 1008 can be pivoted about the pivot pin 1012 to the disengaged position shown in FIG. 31E. The lever 1008 can then be held in that disengaged position, in which the threads 1016 are spaced apart from the plunger 1006, by having the pin 1018 positioned in notch 1022. A biasing spring 1025 may bias the lever 1008 back towards the engaged position. Thus, the lever 1008 may be returned to the engaged position of FIG. 31D by pushing distally on a button 1026 connected to the pin 1018, so that the pin 1018 compresses a spring 1028 until a narrowed region 1030 of the pin 1018 becomes aligned with the notch 1022, thus allowing the lever 1008 to rotate back towards the engaged position under the influence of the biasing spring 1025. Alternatively, the lever 1008 may be moved back to the engaged position by simply pulling on the projection 1010 until the pin 1018 disengages the notch 1022.

The two modes of travel discussed above may desirably permit the plunger 1006 to advance the hydraulic fluid into the implant in the rotational, threaded engagement mode, and then the plunger 1006 can be quickly released by disengaging the lever 1008 and pulling the plunger 1006 in the proximal direction. The two states of engagement between the lever 1008 and the plunger 1006 may also give the surgeon a choice between two modes for delivery of the hydraulic fluid into the implant. That is, the surgeon may use the threaded advancement mode if a slower and more controlled advancement is appropriate, and/or if it is desirable to employ the mechanical advantage provided by the screw drive to amplify the input force. The surgeon may also choose to use the sliding, non-threaded mode if more rapid advancement of the plunger is desirable. The sliding, non-threaded mode may also desirably allow the plunger 1006 to be initially positioned into or removed from the receptacle 1024 of the connect cap 1002 relatively quickly, by eliminating the need to threadedly advance or retract the plunger 1006 the entire distance to the desired position.

Figure 15B:
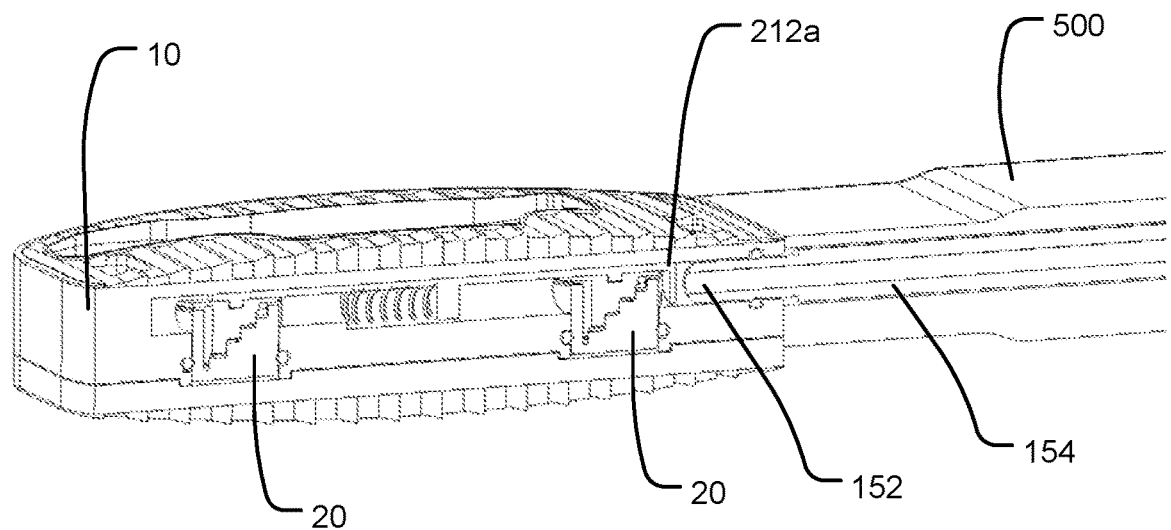
FIG. 15B is a perspective, cross-sectional view of the expandable implant connected to the distal end of the delivery tool.
Figure 15C:
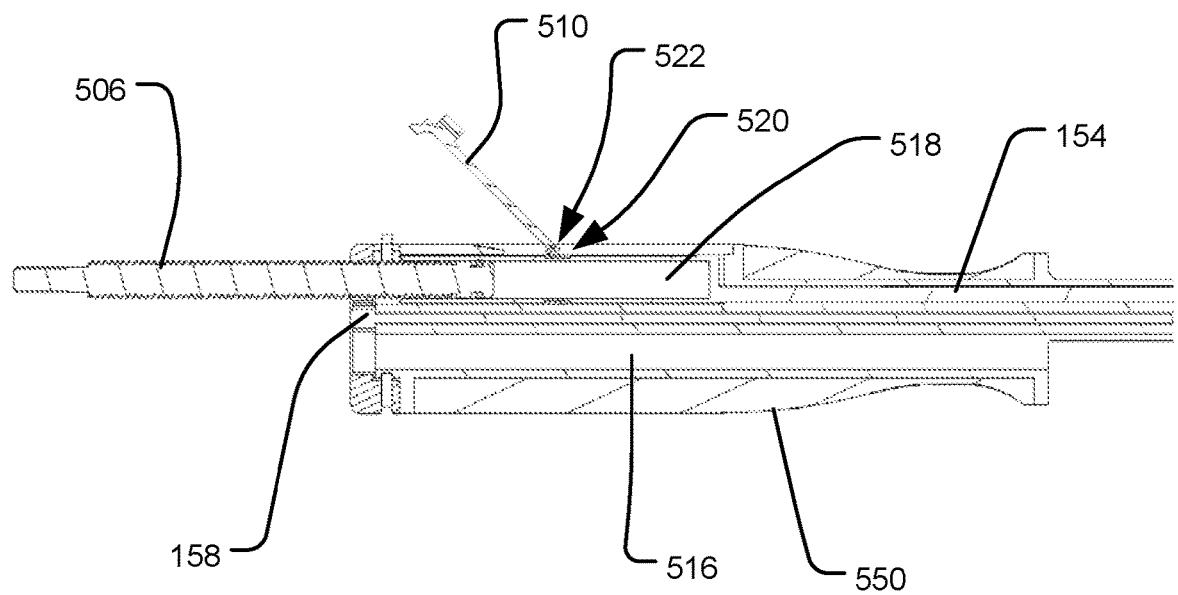

FIGS. 15A-15D illustrate the interaction between rack mechanism 520 on reservoir 518 and pinion mechanism 522 on flip lever 510. Before flip lever 510 is activated, outlet 152 for delivering pressurized fluid at the distal end of the fluid delivery cannula 154 is a distance away from the pushable unlocking tether 212a in the expandable implant 10, as illustrated in FIGS. 15A-B. As disclosed in the '199 Publication, pressing distally on the pushable unlocking tether 212a allows for expandable implant 10 to collapse so that it can be repositioned if necessary. That is, the expandable implant 10 may include a pushable unlocking tether 212a engaged with a lower lock support so as to rotate the lower lock support 20 in the unlock direction when the pushable unlocking tether 212a is pushed in the distal direction.

Figure 15D:
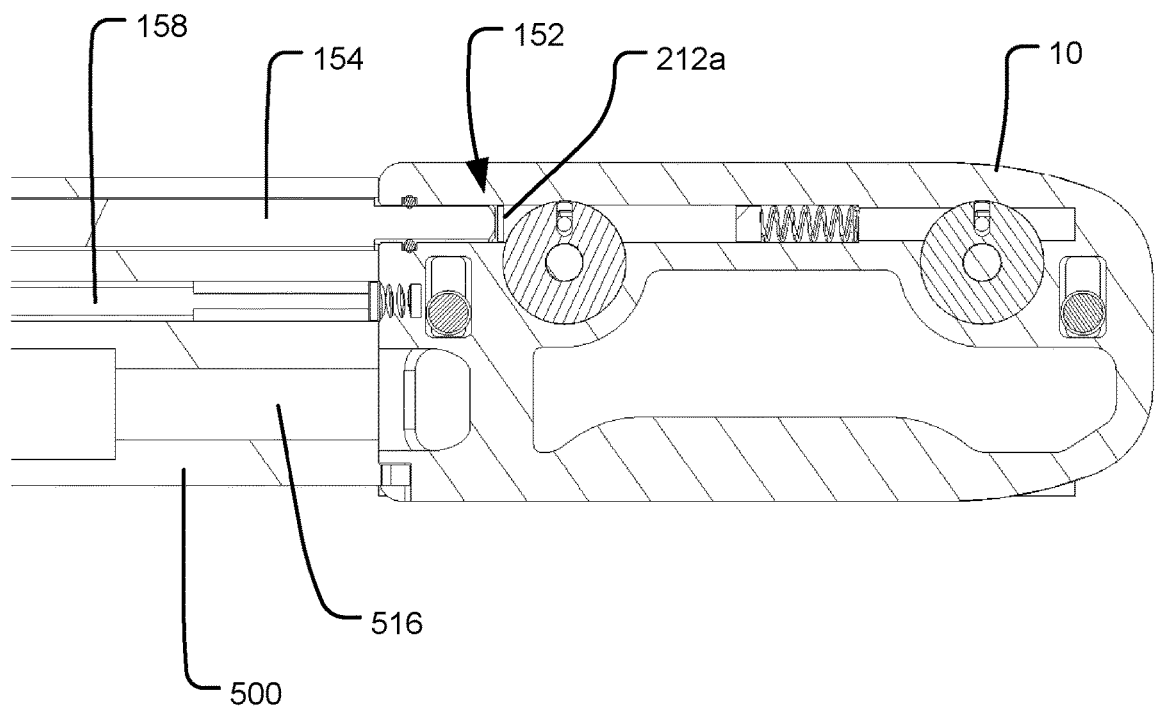

FIG. 15C illustrates the activation of flip lever 510. As the flip lever 510 is pivoted outwardly from its initial position extending along and substantially flush with the outer surface of the handle 550 as shown in FIGS. 13-14, the pinion mechanism 522 on the flip lever 510 interacts with rack mechanism 520 on reservoir 518 to cause reservoir 518 and fluid delivery cannula 154 to move towards the distal end of insertion shaft 500. As reservoir 518 and fluid delivery cannula 154 move towards the distal end of insertion shaft 500, outlet 152 for delivering pressurized fluid also moves distally and pushes on the internal unlocking mechanism within the expandable implant 10, as shown in FIG. 15D. This causes the expandable implant 10 to collapse so that the expandable implant 10 can be repositioned if necessary. Returning flip lever 510 to the original position withdraws outlet 152, fluid delivery cannula 154, and reservoir 518 back to the original depth, allowing expandable implant 10 to be re-expanded.

Instead of using a thin, flexible wire to push the unlocking mechanism within the expandable implant 10, as may be done in some other delivery tools, the flip lever 510 may beneficially allow for the relatively rigid structure of fluid delivery cannula 154 to move to activate the unlocking mechanism within expandable implant 10.

In another embodiment of delivery tool 100, FIGS. 16A-16C exemplify handle 602 having a pressure gauge 600 to measure the pressure of the fluid in the fluid delivery cannula 154 as the handle 602 is turned. Pressure gauge 600 provides numerical readings of the pressure of the fluid inside the expandable implant 10. Handle 602 has a recess to receive pressure gauge 600. The distal end of pressure gauge 600 has a threaded member that allows for a secure connection between pressure gauge 600 and handle 602.

The distal end of handle 602 is threaded to receive the threaded proximal end of handle connector 610. A secure connection between handle 602 and handle connector 610 is formed such that the rotation of handle 602 is transmitted to the handle connector 610. Handle connector 610 connects handle 602 to plunger 606. The proximal end of plunger 606 is fitted to have o-ring 608 as part of its assembly when connected to the distal end of handle connector 610.

Plunger 606 has a passageway 612 to provide fluid communication between the fluid delivery cannula 154 and the pressure gauge 600, so that the pressure gauge 600 can read the pressure in the fluid delivery cannula 154 as hydraulic fluid is delivered to the expandable implant 10. The passageway 612 in plunger 606 communicates with passageways in handle 602 and handle connector 610, as shown in FIG. 16C. O-ring 608 is in place to create a seal between the plunger 606 and handle connector 610 to minimize leakage between those components. Plunger 606 also has an o-ring 604 located at the distal end of plunger 606 that creates a movable seal between the plunger 606 and the reservoir 518 of the fluid delivery cannula 154 as the plunger 606 advances within the reservoir 518.

The distal end of plunger 606 is inserted into the proximal end of receptacle 524 on connect cap 502. The threading of plunger 606 is the same as plunger 506, allowing the threading of plunger 606 to also match the threading of receptacle.

Plunger 606 is operated by turning handle 602. As the handle 602 is turned, plunger 606 pushes hydraulic fluid from reservoir 518 through the fluid delivery cannula 154 and out the outlet 152 into the expandable implant 10, causing expandable implant 10 to expand. Beneficially, the pressure gauge 600 may provide an absolute reading, instead of a relative measure, of the pressure of the fluid in the expandable implant 10. This may help prevent the surgeon from over-pressurizing the expandable implant 10. In an alternative embodiment, the gauge may provide a relative pressure reading, such as by displaying color-coded regions associated with different pre-defined ranges of pressure.

Figure 17:
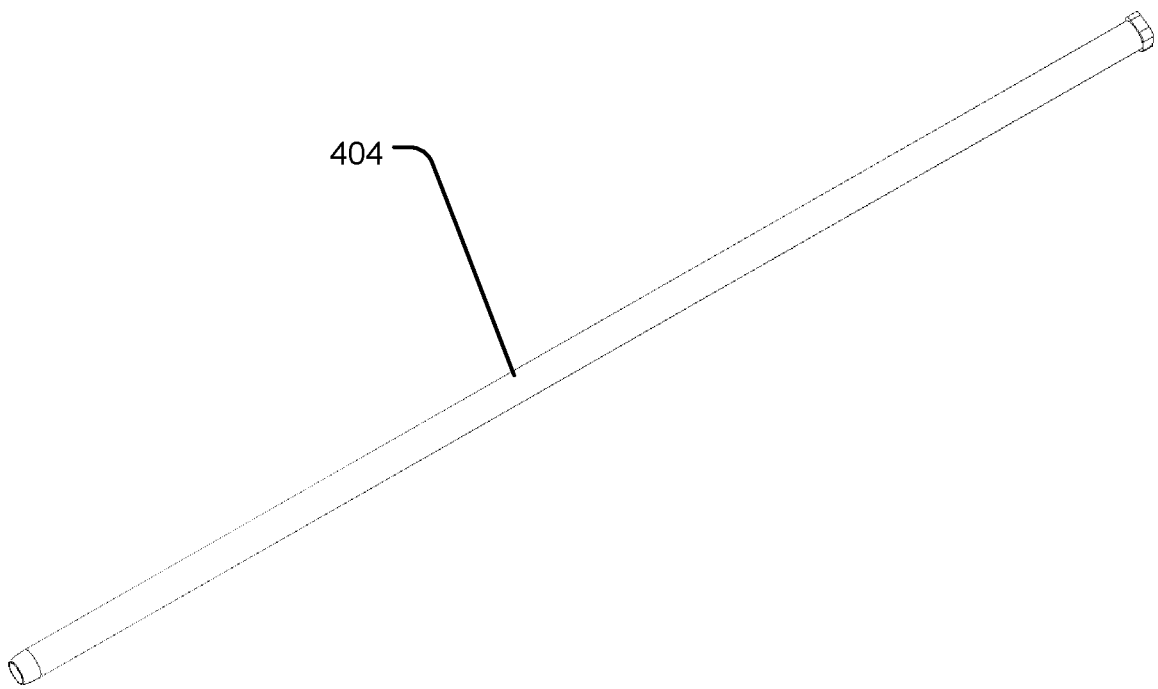
FIG. 17 is a perspective view of a bone graft supply line.

The delivery system provides a bone graft supply system for back-filling the expandable implant 10 with graft material. The bone graft supply line 404 of the bone graft supply system, as illustrated in FIG. 17, is a cannula that does not have to be inserted into the delivery tool 100 until after the expandable implant 10 is inserted. By inserting the bone graft supply line 404 into the delivery tool 100 after the expandable implant 10 is inserted, there will be better visualization of the anatomy and the expandable implant 10 during insertion and graft material can be prepared and loaded at the same time the expandable implant 10 is being inserted. The cannula used for the bone graft supply line 404 may also be translucent, which allows for better visualization of the amount of graft material being delivered.

In some embodiments it may be preferable to have a large diameter bone graft supply line 404 for receiving different sizes of graft material. In one embodiment, the diameter of the bone graft supply line 404 is 6 mm ID. In contrast to other commercial products, providing such a larger diameter bone graft supply line 404 may beneficially allow for the use of more types of graft materials, such as cancellous chips, autograft, or synthetic bone graft materials such as those manufactured by Orthovita, Inc. under the trademark VITOSS®.

Figure 18:
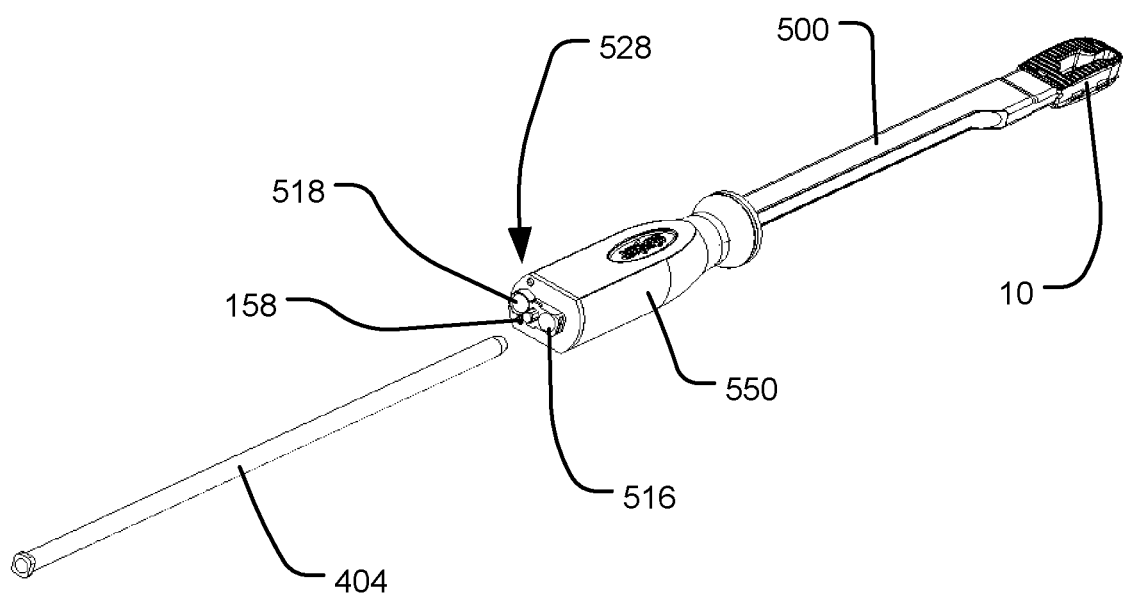
FIG. 18 is a perspective view of the insertion of the bone graft supply line into the delivery tool.
Figure 19:
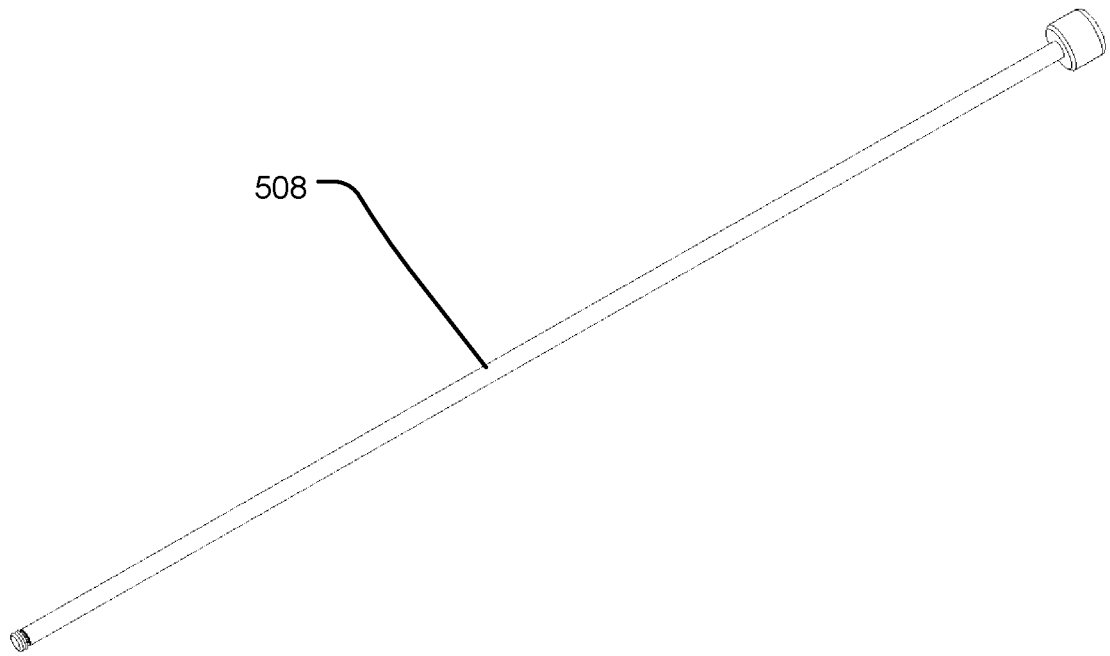
FIG. 19 is a perspective view of a plunger for the bone graft supply line.
Figure 20A:
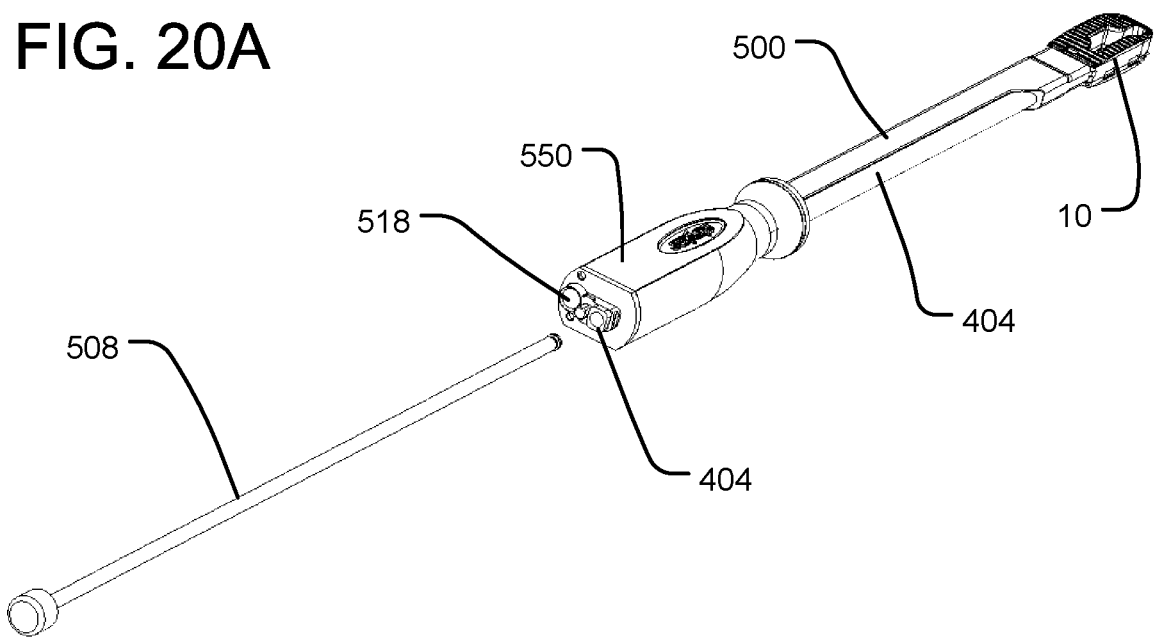
FIGS. 20A-20B are perspective views of the insertion of the plunger into the bone graft supply line.
Figure 20B:
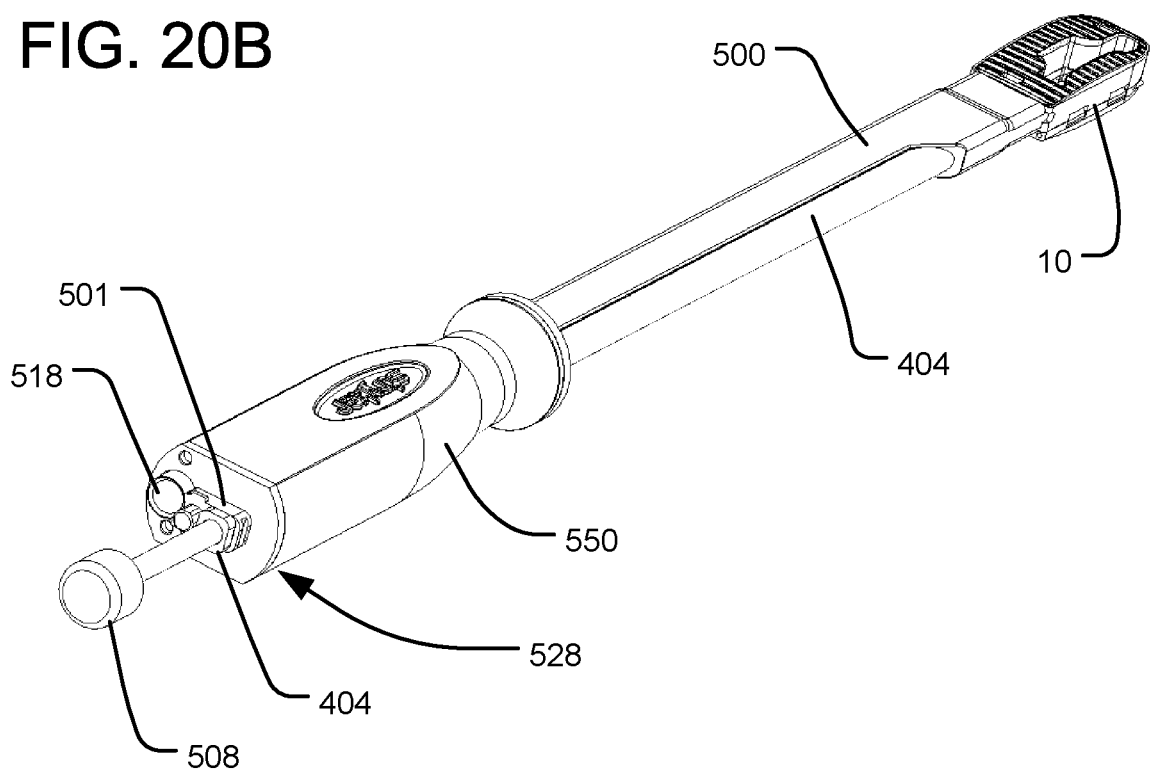
Figure 21A:
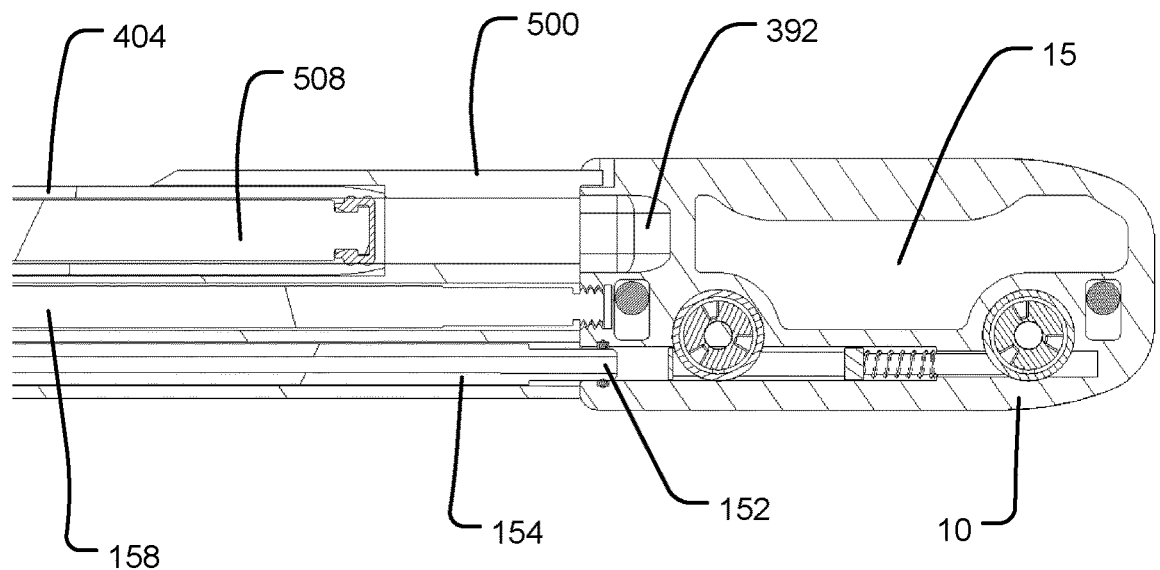
FIGS. 21A-21B are cross-sectional views of the movement of the plunger of FIG. 19 within the bone graft supply line.
Figure 21B:
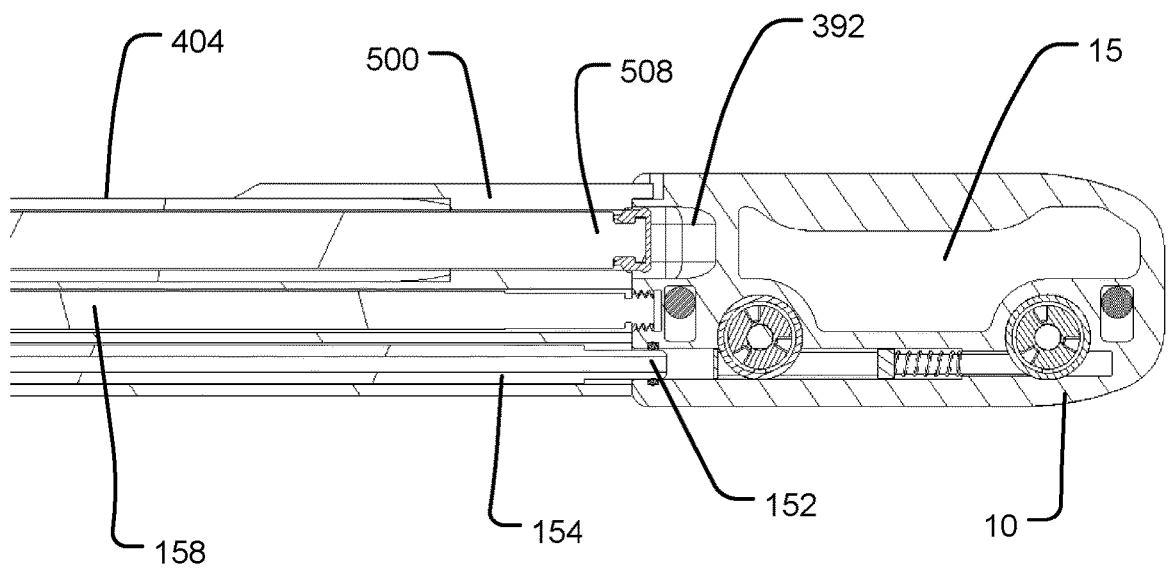

As illustrated in FIG. 18, the distal end of the bone graft supply line 404 is inserted into the proximal end of receptacle 516 on the handle 550. Once bone graft supply line 404 is seated within receptacle 516 in handle 550, a plunger 508 of the bone graft supply system is introduced and inserted into the proximal end of the bone graft supply line 404, as illustrated in FIGS. 19-20B, for dispensing the graft material. Although FIG. 20 does not illustrate connect cap 502 being connected to handle 500, it may be in place when using plunger 508, in which case the plunger 508 can be introduced through the receptacle 526 of the connect cap when inserting the plunger 508 into the bone graft supply line 404. As illustrated in FIGS. 21A-21B, plunger 508 is pushed in the distal direction, causing graft material to move distally through the bone graft supply line 404 and into the passage for graft material 392 of the expandable implant 10, to back-fill the interior cavity 15 of the expandable implant 10.

Figure 22A:
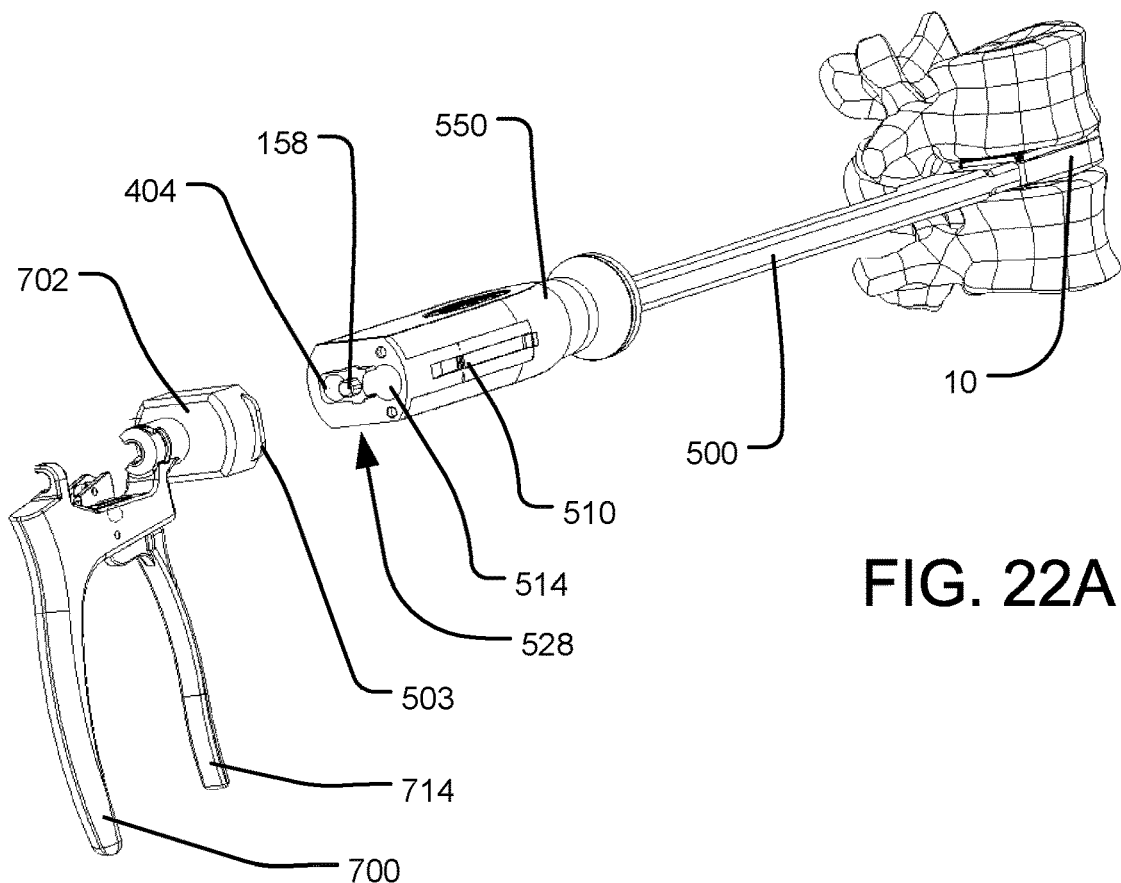
FIGS. 22A-22B are perspective views of the attachment of a connect cap fitted with a pistol-grip handle.
Figure 22B:
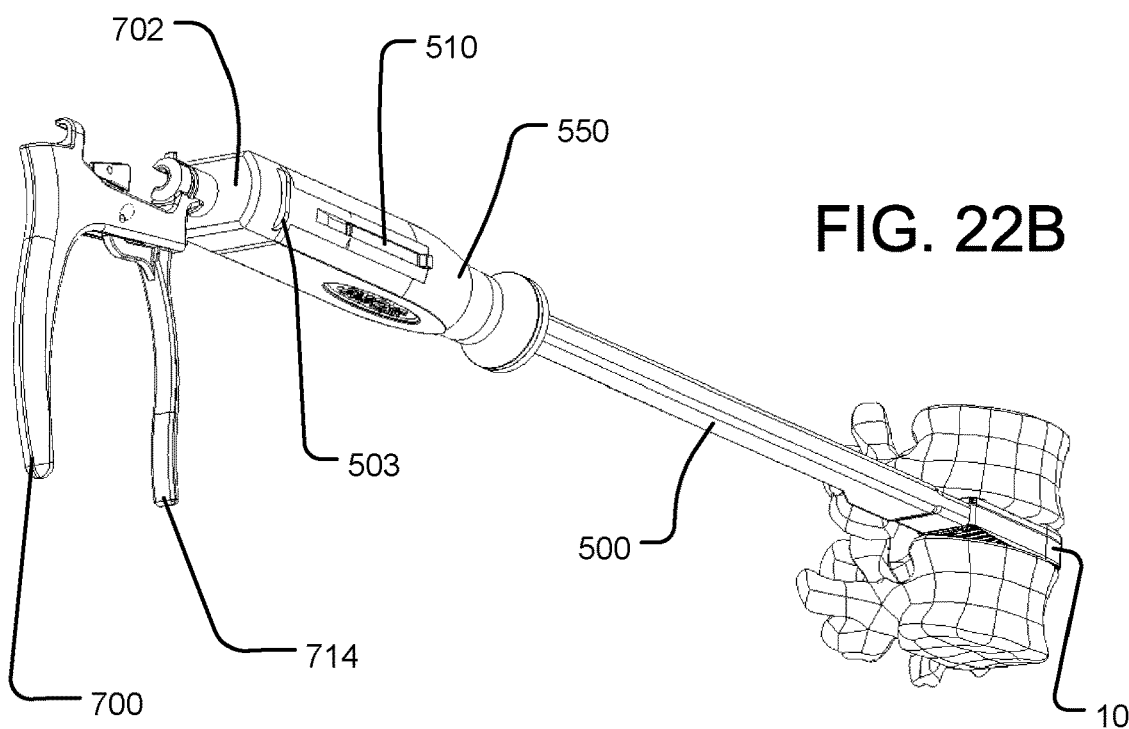

In another embodiment of a bone graft supply system, as illustrated in FIGS. 22A-22B, connect cap 502 may be replaced with connect cap 702, which is fitted with a pistol-grip handle 700 to form a bone graft gun for delivering graft material to the expandable implant 10. The process of attaching and removing connect cap 702 is the same process as attaching and removing connect caps 502 and 504.

Figure 23:
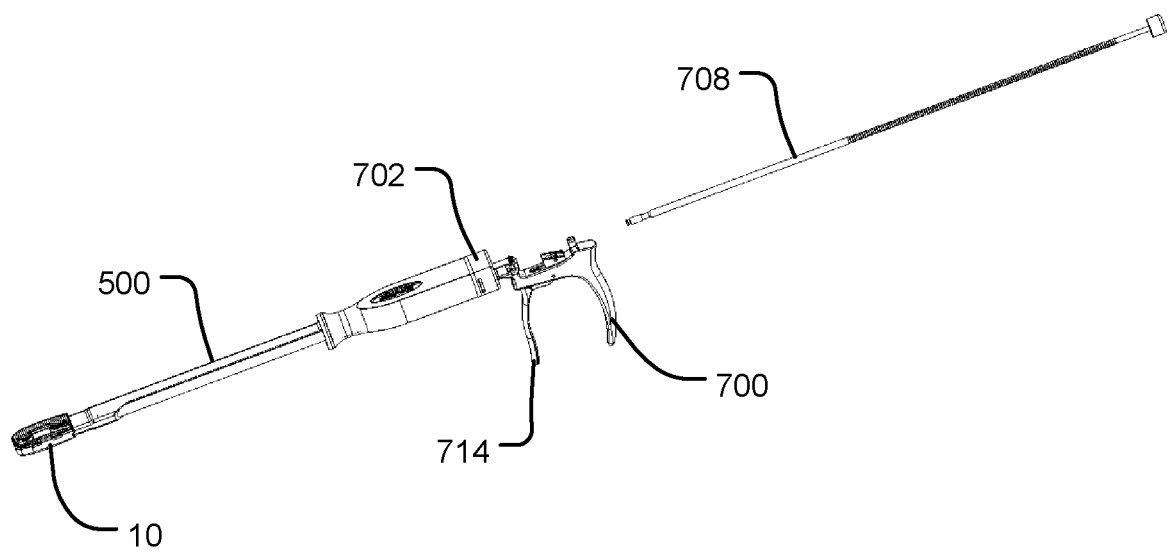
FIG. 23 is a perspective view of the insertion of a plunger that fits within the pistol-grip handle.
Figure 24A:
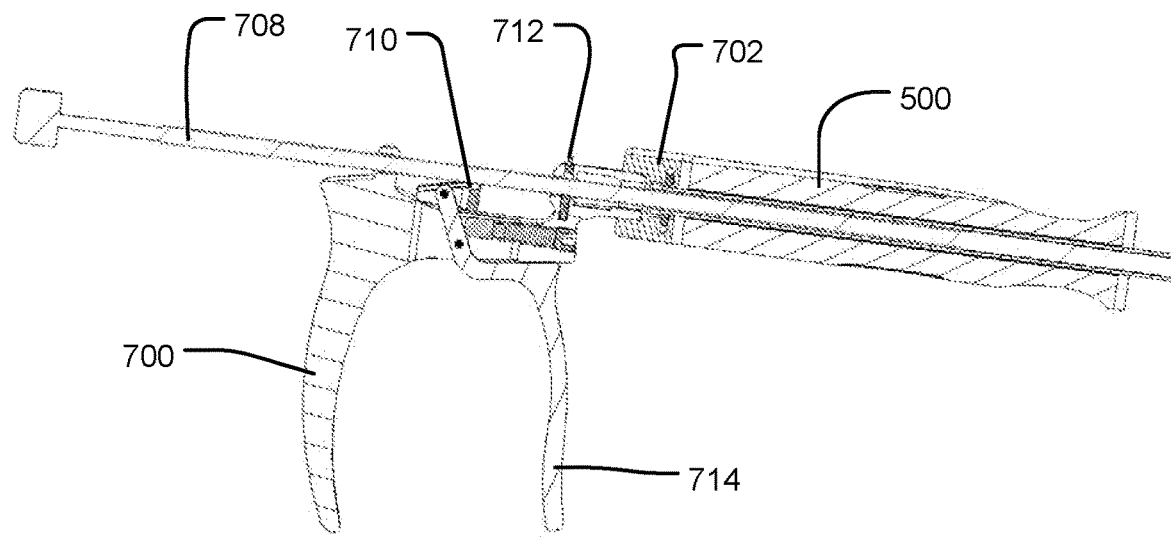
FIGS. 24A-24B are side, cross-sectional views of the pistol-grip handle with the plunger inserted to deliver graft material to the expandable implant.
Figure 24B:
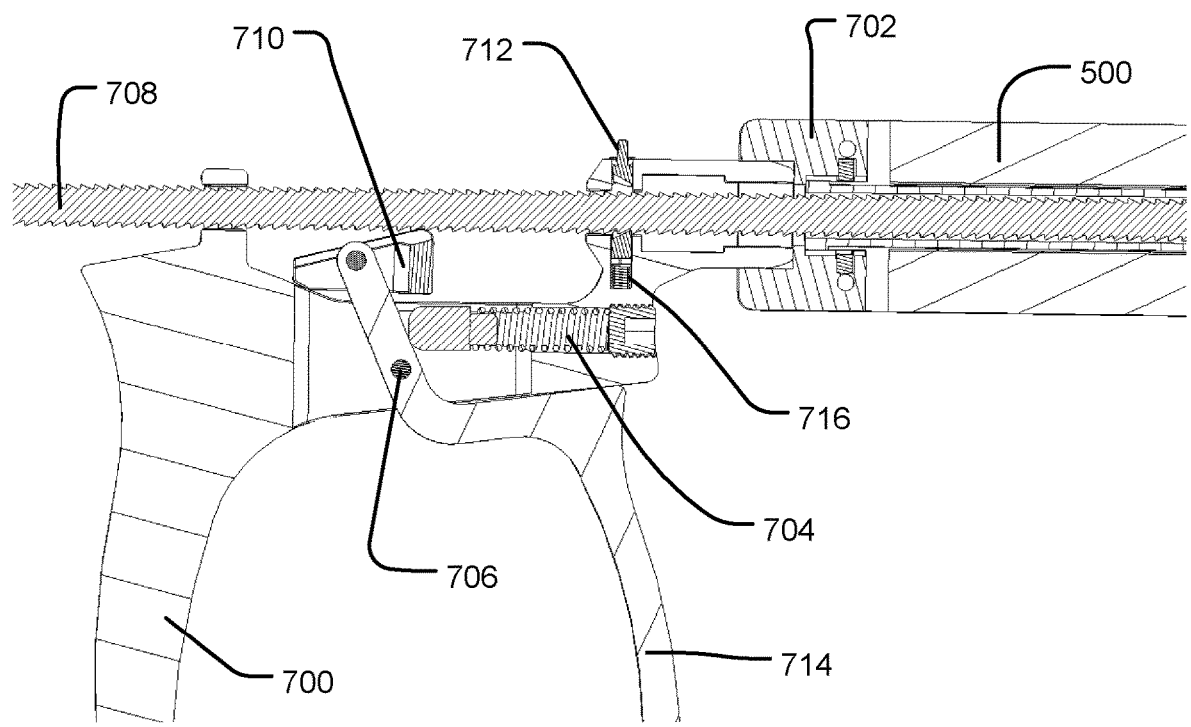

After connect cap 702 is connected to handle 550, the distal end of plunger 708 is inserted into the proximal end of the pistol-grip handle 700, as illustrated in FIG. 23. Plunger 708 is designed to work with the pistol-grip handle 700 using a ratcheting advancement mechanism. As the pistol-grip trigger 714 is squeezed towards the handle 700, the trigger 714 pivots about pivot point 706 such that movable pawl 710 connected to the trigger 714 engages ratchet teeth on the plunger 708 and pushes the plunger 708 distally. When the trigger 714 is released, a biasing spring 704 moves the trigger 714 back to its original position. As the plunger 708 is advanced in the distal direction, the ratchet teeth are pushed through a spring-biased fixed pawl 712 that prevents the plunger 708 from retracting in the proximal direction, unless the fixed pawl 712 is released from engagement with the plunger 708 by pushing the fixed pawl 712 against its spring 716. The distal movement of the plunger 708 pushes graft material through bone graft supply line 404 and into the passage for graft material 392 of the expandable implant 10 to fill the interior cavity 15 of the expandable implant 10. This process is exemplified in FIGS. 24A-24B. It is believed that using a ratcheting mechanism in this manner is preferable over tamping the bone graft material, as tamping may cause jamming of the bone graft material.

Figure 25:
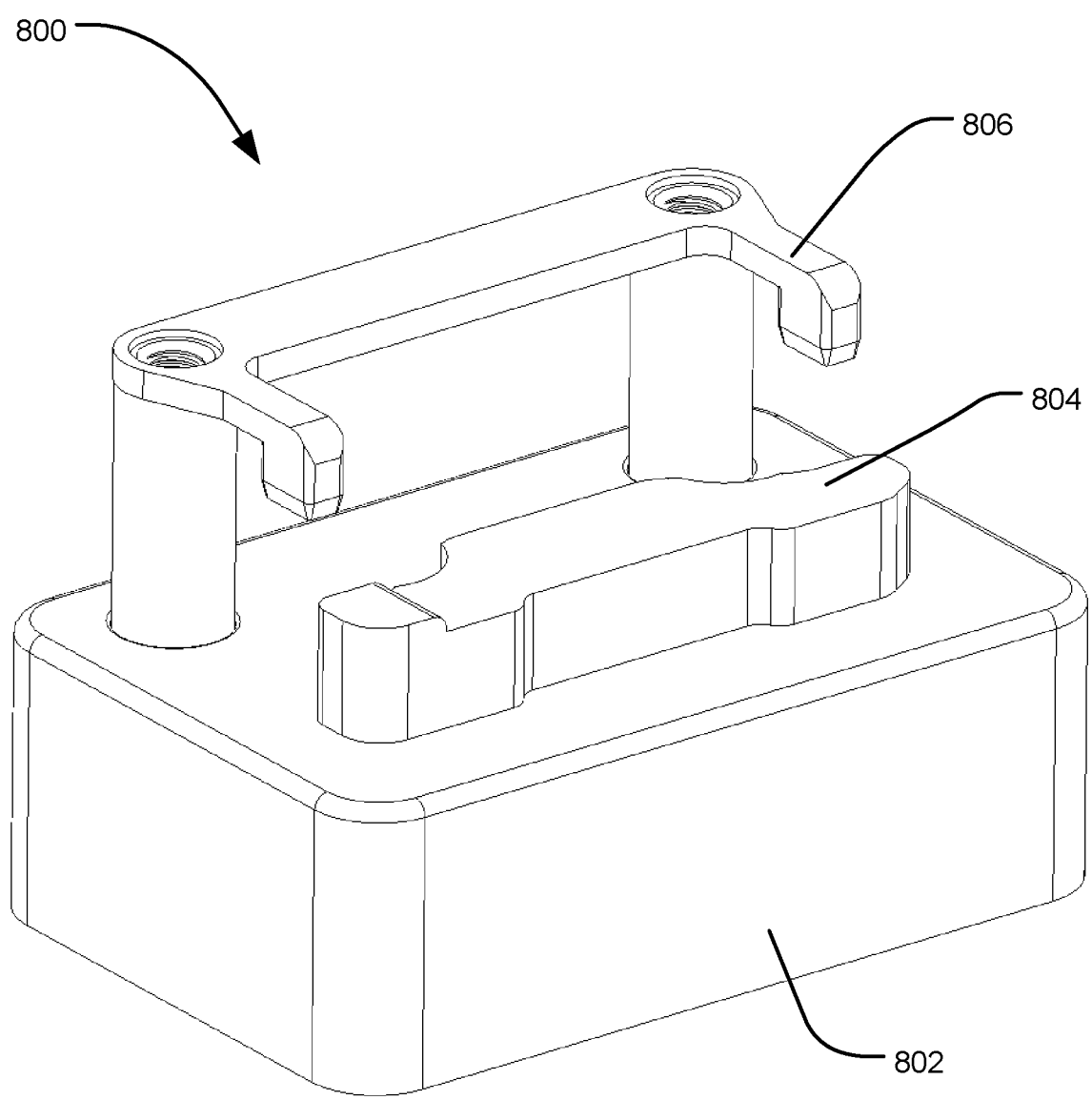
FIG. 25 is a perspective view of a grafting block.
Figure 28A:
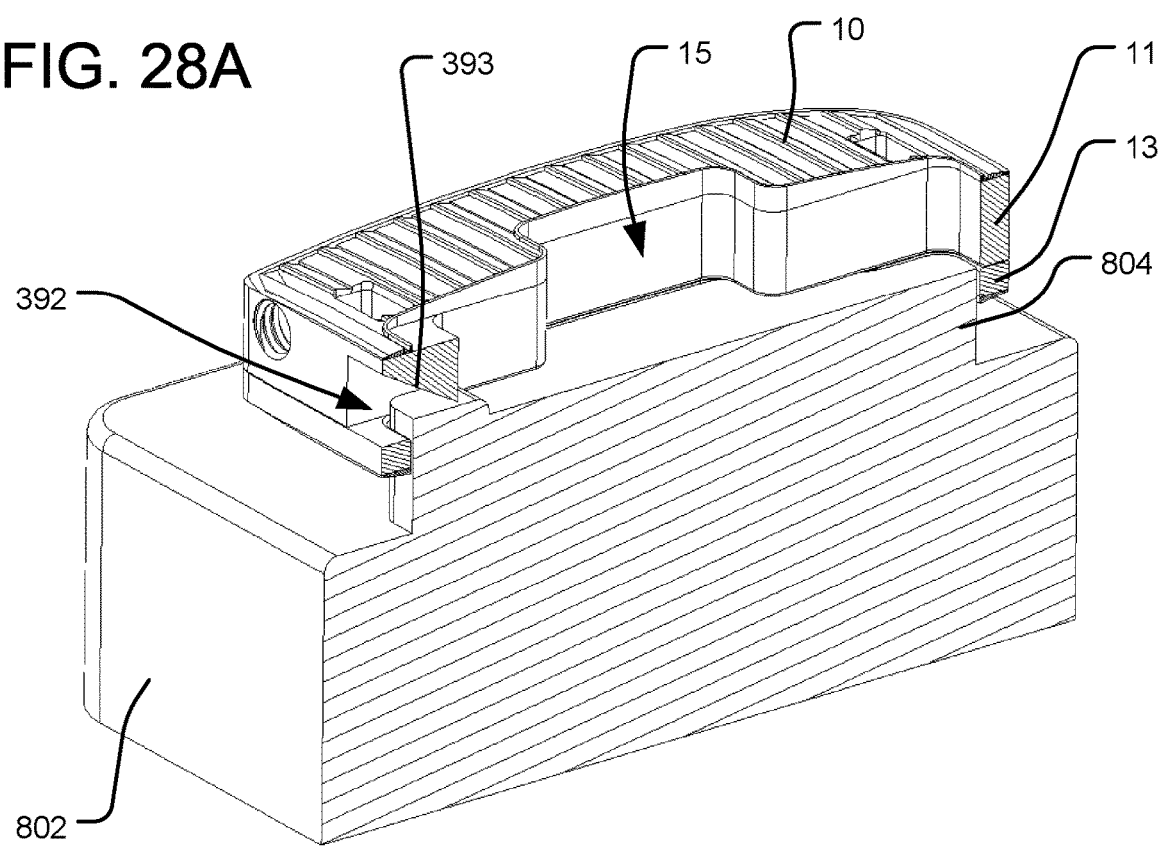
FIGS. 28A-28B are perspective, cross-sectional views of the expandable implant on the grafting block of FIG. 27.
Figure 28B:
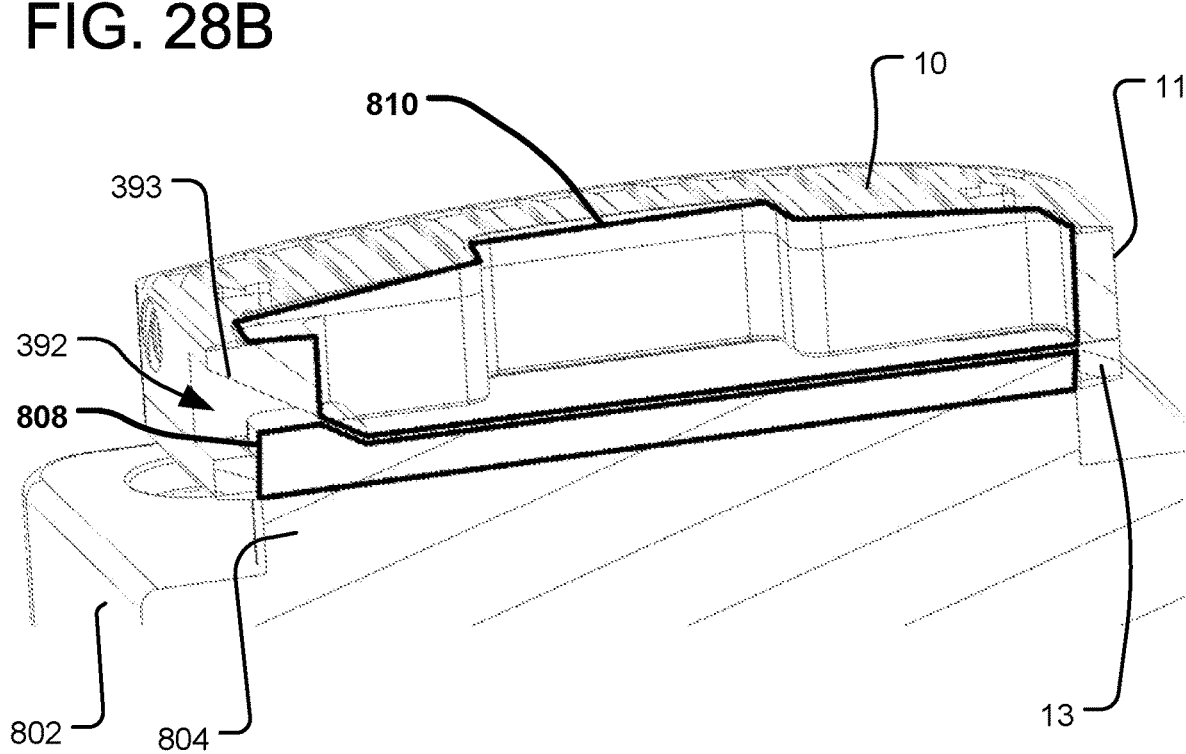

The expandable implant 10 can be pre-packed with graft material, back-filled with graft material after implantation, or a combination of both. FIG. 25 illustrates one embodiment of a grafting block 800 that can be used to help pre-pack the implant 10 with graft material. A projection 804 from a base 802 of the grafting block 800 is shaped to be at least partially received within the interior cavity 15 of the expandable implant 10, as shown in FIGS. 28A-28B, such that the projection 804 occupies a portion 808 of the interior cavity 15 extending from the passage 392, while leaving a remaining open region 810 of the interior cavity 15 unoccupied. In that way, that projection 804 will prevent graft material packed into the open region 810 of the interior cavity 15 from filling the portion 808 extending from the passage 392, which might cause a blockage to the later-inserted graft material when back-filling the expandable implant 10 after insertion. For example, the projection 804 may be configured at one end to a height that matches the apex of the ramp 393 inside the expandable implant 10. The remainder of the projection 804 may be configured to a height that is aligned with the boundary between the implant housing 11 and the expandable top end plate 13. In that way, any back-filled graft material added later will primarily fill the initial portion 808 that was blocked out, as well as the new volume created by the expansion of the implant.

Figure 26A:
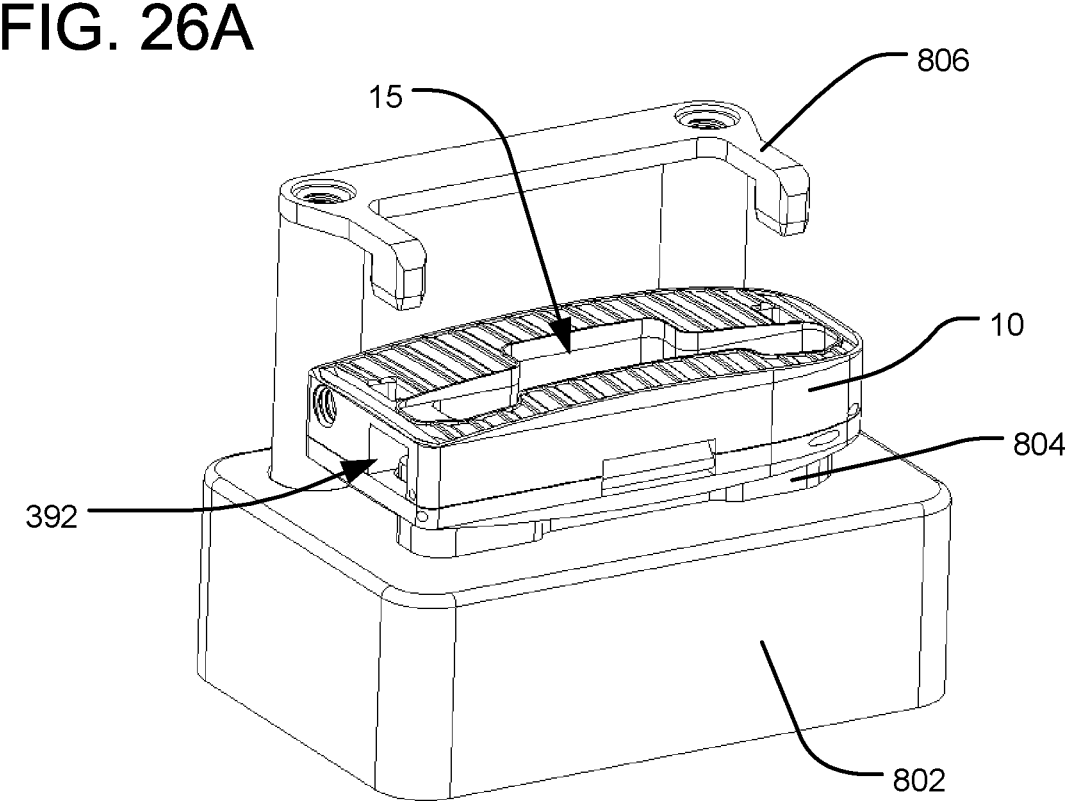
FIGS. 26A-26B are perspective views of the grafting block with the expandable implant placed upon it and a retaining mechanism at varying heights.
Figure 26B:
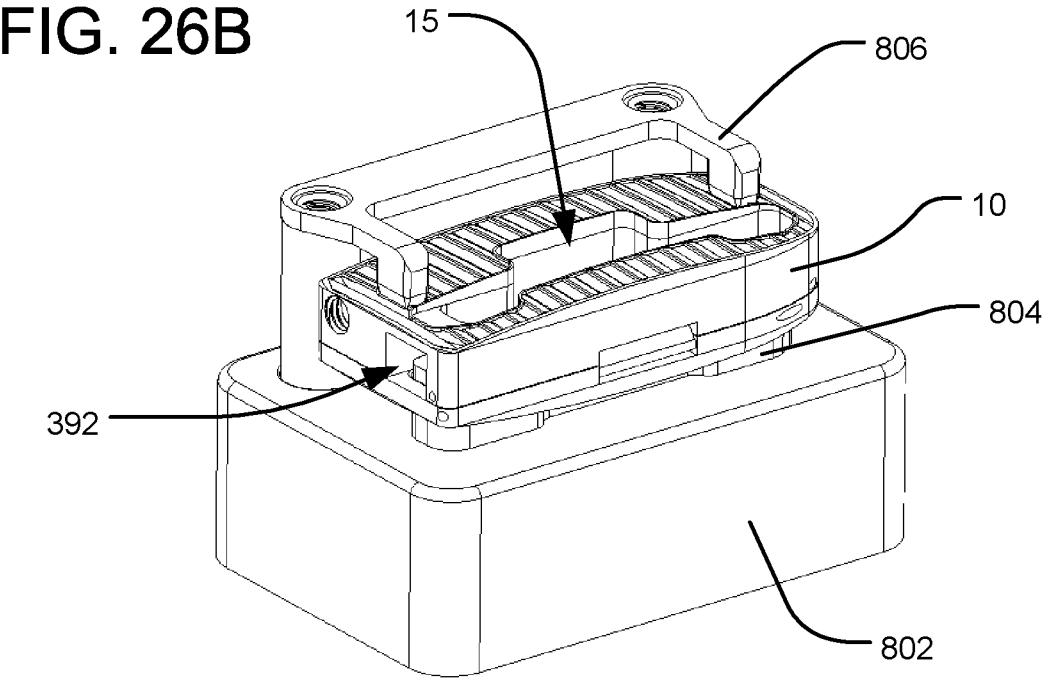
Figure 26C:
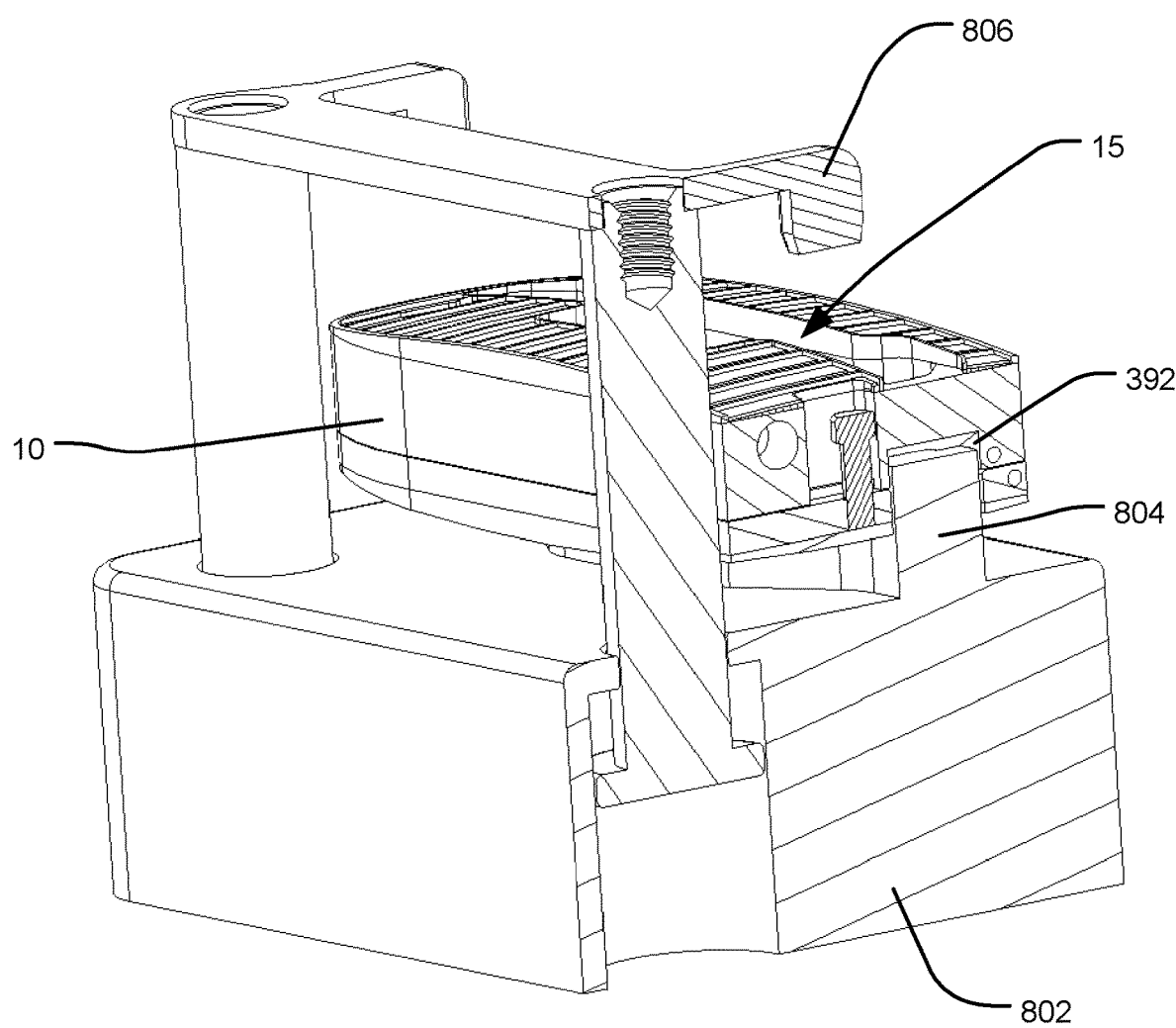
FIG. 26C is a perspective, cross sectional view of the grafting block with retaining mechanism having the expandable implant placed upon it.

In one embodiment, there is a retaining mechanism 806 that will assist in keeping the expandable implant 10 on the grafting block 800. The retaining mechanism 806 is adjustable in height, as illustrated in FIGS. 26A-26C. Retaining mechanism 806 allows for the expandable implant 10 to be placed on the projection 804 when the retaining mechanism 806 is in the raised position. When the retaining mechanism 806 is lowered after the expandable implant 10 is placed on the projection 804, the retaining mechanism 806 assists in keeping the expandable implant 10 on the grafting block 800.

Figure 27:
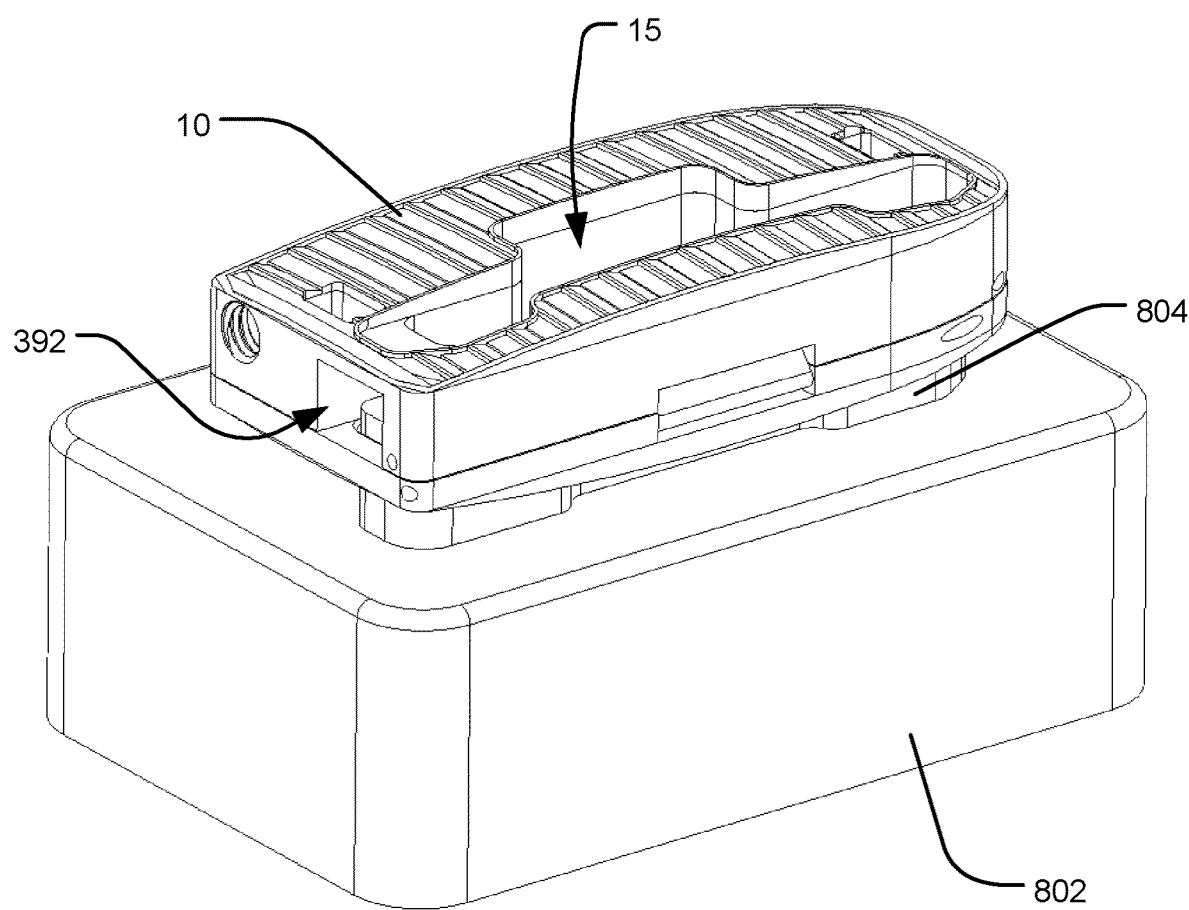
FIG. 27 is a perspective view of the expandable implant on an alternative embodiment of a grafting block without a retaining mechanism.

FIGS. 27-28B show an alternative embodiment of the grafting block 800. In the alternative embodiment, the grafting block 800 does not have the retaining mechanism 806. As with other instruments and devices disclosed herein, the use of the grafting block 800 is optional. In one example, when no pre-packing of the graft material is performed (e.g., where the graft material is entirely supplied via the bone graft supply line 404 after the implant 10 has been implanted), the grafting block 800 may not be used.

The ramp 393 inside the expandable implant 10 is used to guide graft material into the area of the interior cavity 15 that was not pre-packed using the grafting block 800. The ramp 393 guides new graft material into the expanded volume that is created once the expandable implant 10 is inserted and expanded.

Figure 29:
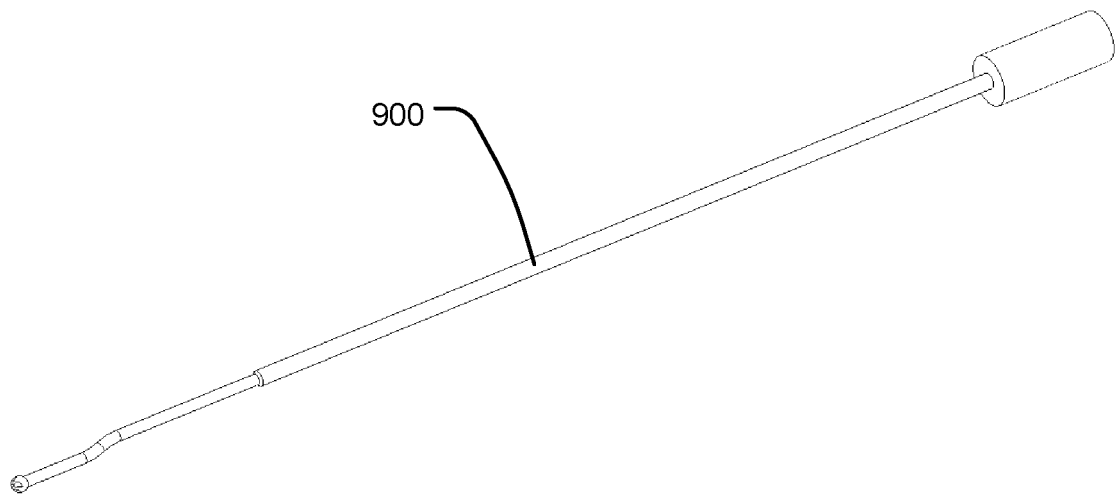
FIG. 29 is a perspective view of a graft reamer.

FIG. 29 illustrates a flexible graft reamer 900 that can be used to clear blockages during backfilling. Graft reamer 900 can also be used to re-establish a grafting channel within passage 392.

Figure 30A:
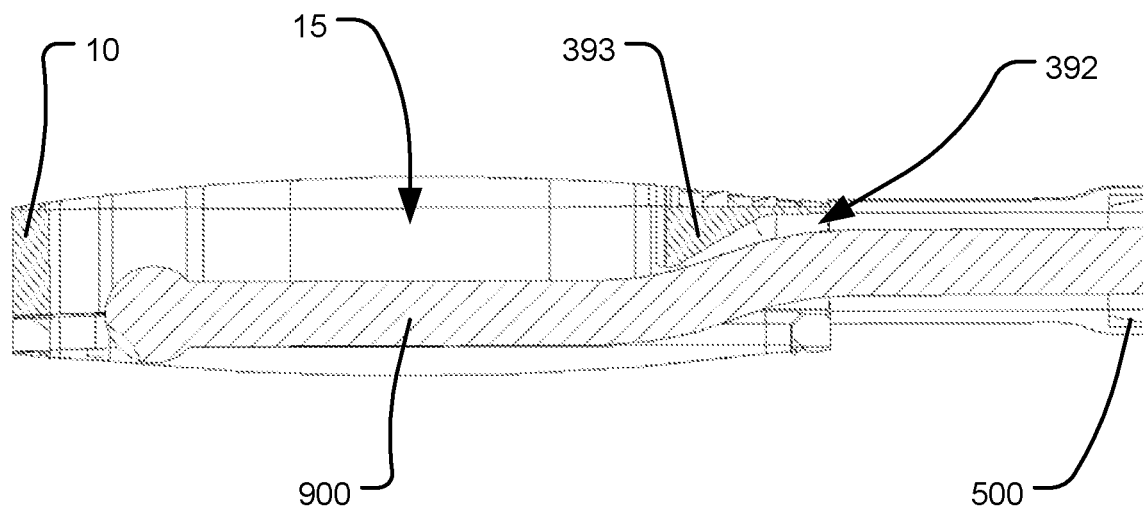
FIGS. 30A-30B are side, cross sectional views of the graft reamer inserted into the expandable implant.
Figure 30B:
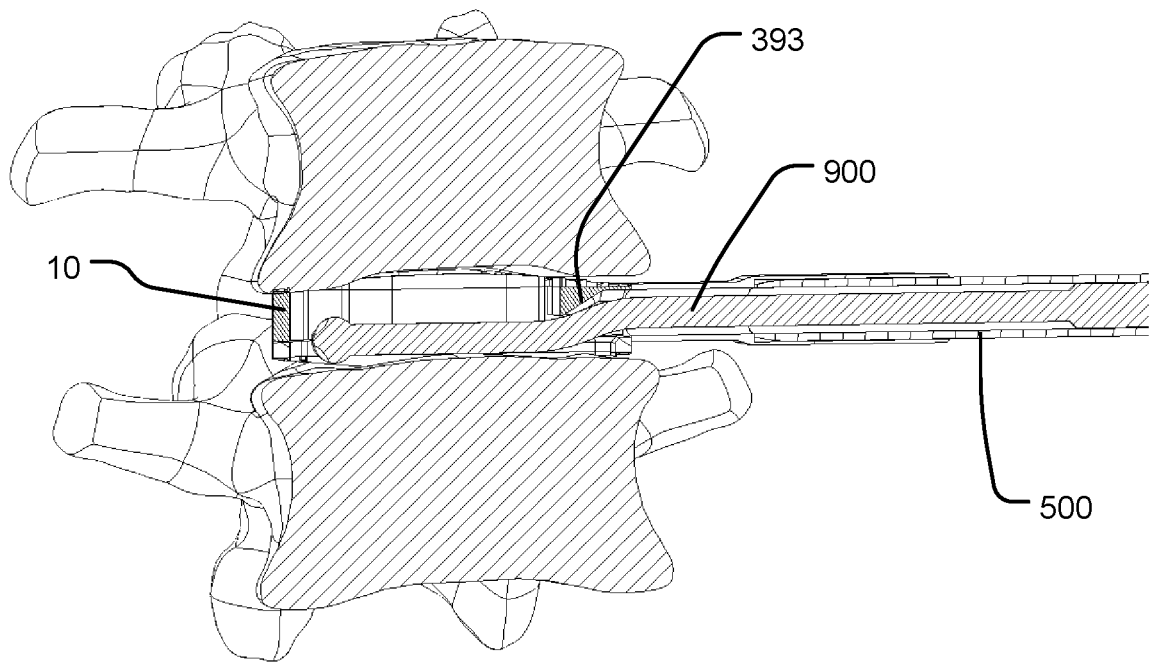

As illustrated in FIGS. 30A-30B, the graft reamer 900 fits within delivery tool 100 while the insertion shaft 500 is connected to the expandable implant 10. The flexibility of graft reamer 900 allows graft reamer 900 to fit within passage 392 in the expandable implant 10 and around ramp 393 in the expandable implant 10.

The components of another embodiment of a delivery system are illustrated in FIGS. 32-44. The components of such embodiment are adapted to provide a surgeon with improved viewability of the expandable implant 10 (both directly and using fluoroscopy), as well as to improve the speed and efficiency of surgery, so as to minimize the time that tissue is retracted.

Figure 32:
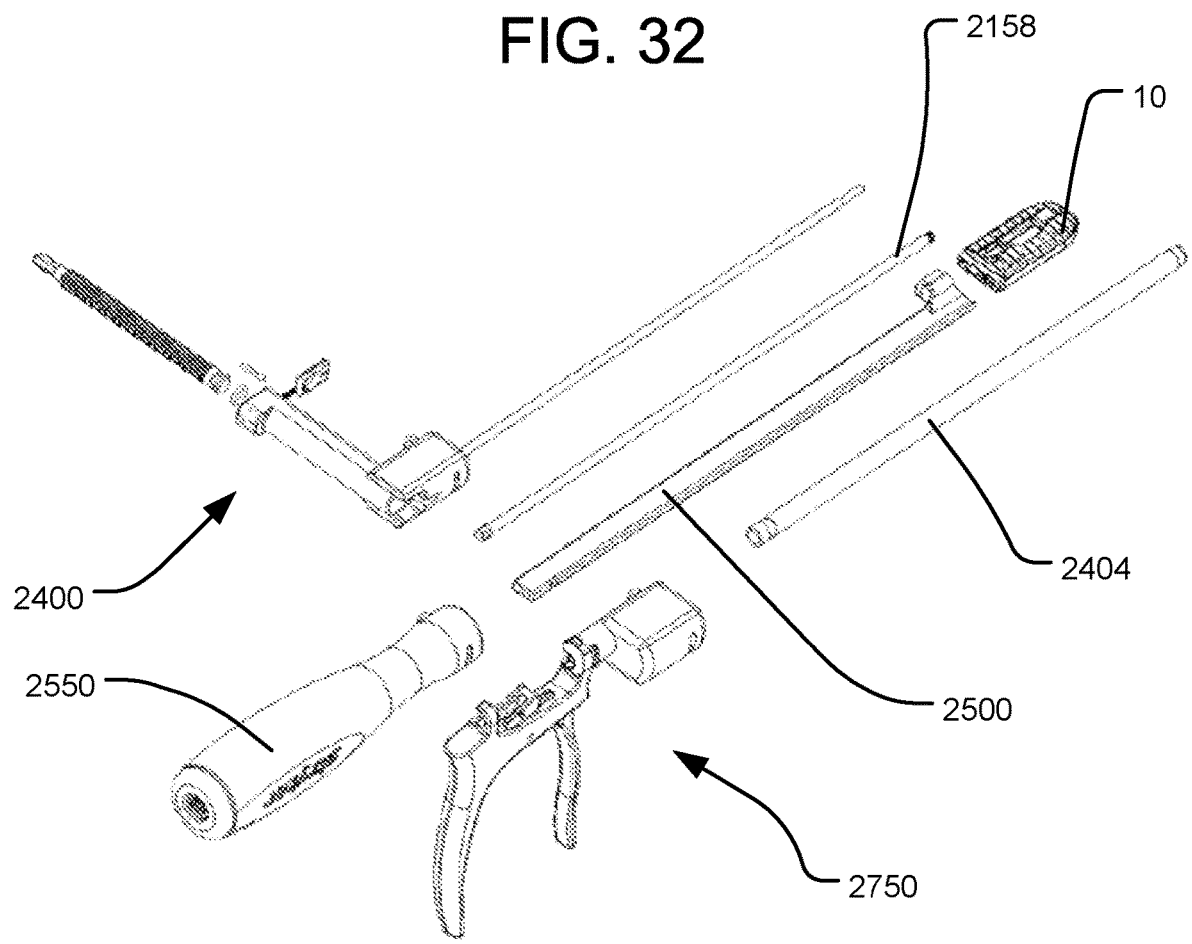
FIG. 32 is an exploded view of an implant delivery system in accordance with another embodiment of the present invention.

In this embodiment, modular parts (including the handle of the delivery tool itself) can be attached to and detached from the insertion shaft of the delivery tool between each phase of the procedure. As illustrated in FIG. 32, the modular instruments consist of a handle 2550, an insertion shaft 2500, a rotatable threaded member 2158, a fluid delivery system 2400, a bone graft gun 2750, and a bone graft supply line 2404. The modular parts can be attached to the insertion shaft using a sliding lock mechanism 2535. The sliding lock mechanism 2535 of the handle 2550 is illustrated in FIGS. 33A-C, but a similar sliding lock mechanism 2535 may be incorporated into the fluid delivery system 2400 and the bone graft gun 2750 for securely (yet removably) coupling those components with the insertion shaft 2500.

Figure 33A:
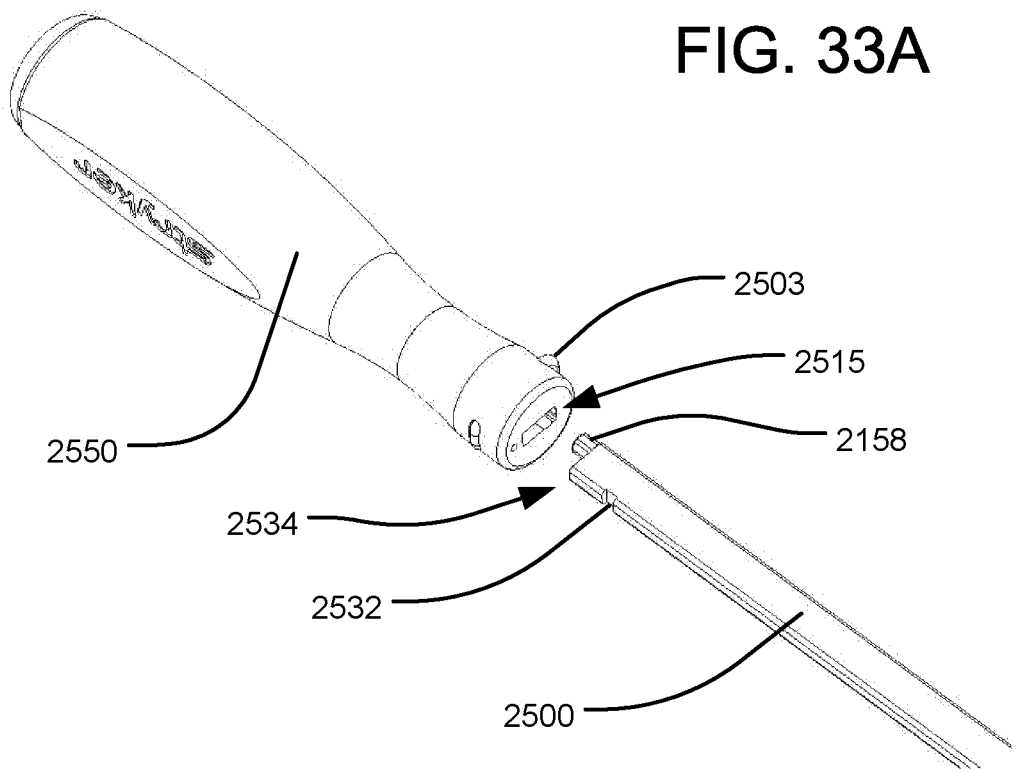
FIG. 33A is a perspective view of the attachment of a handle of the implant delivery system of FIG. 32 to an insertion shaft of the implant delivery system.
Figure 33B:
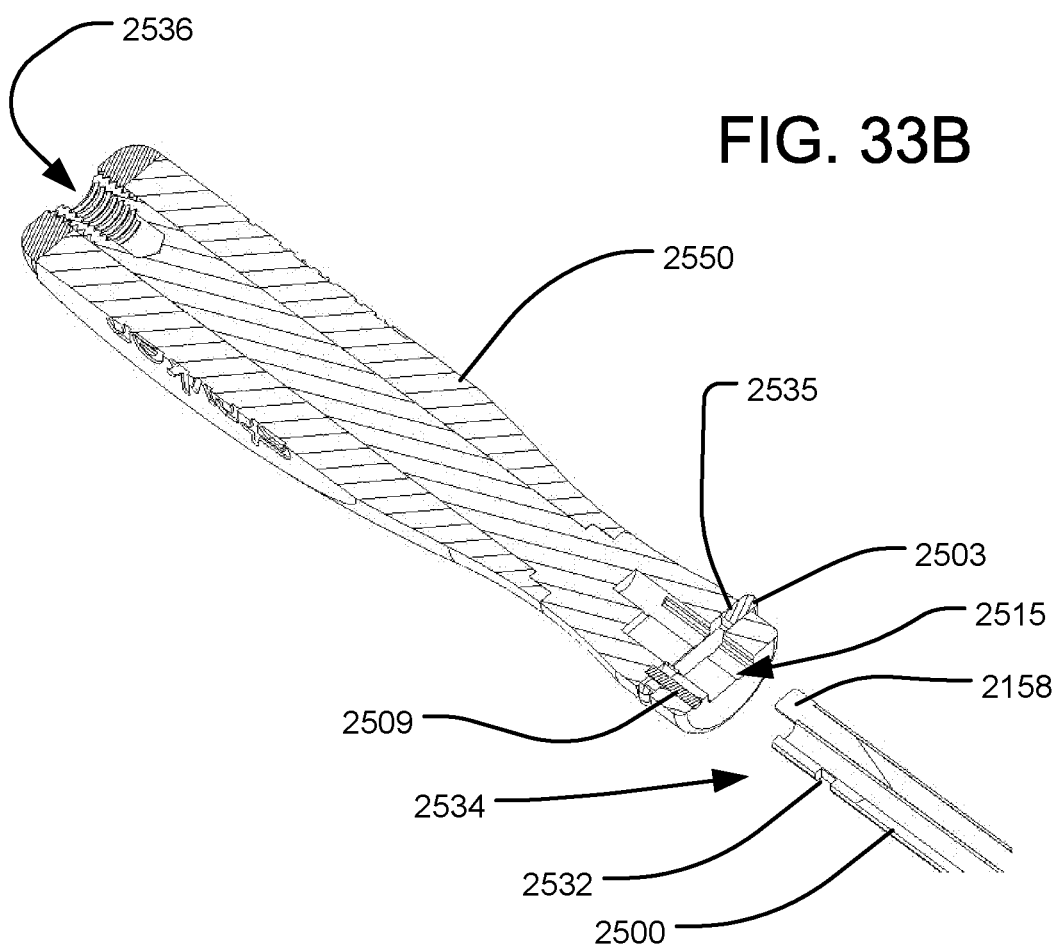
FIG. 33B is a cross-sectional view of the arrangement of FIG. 33A.
Figure 33C:
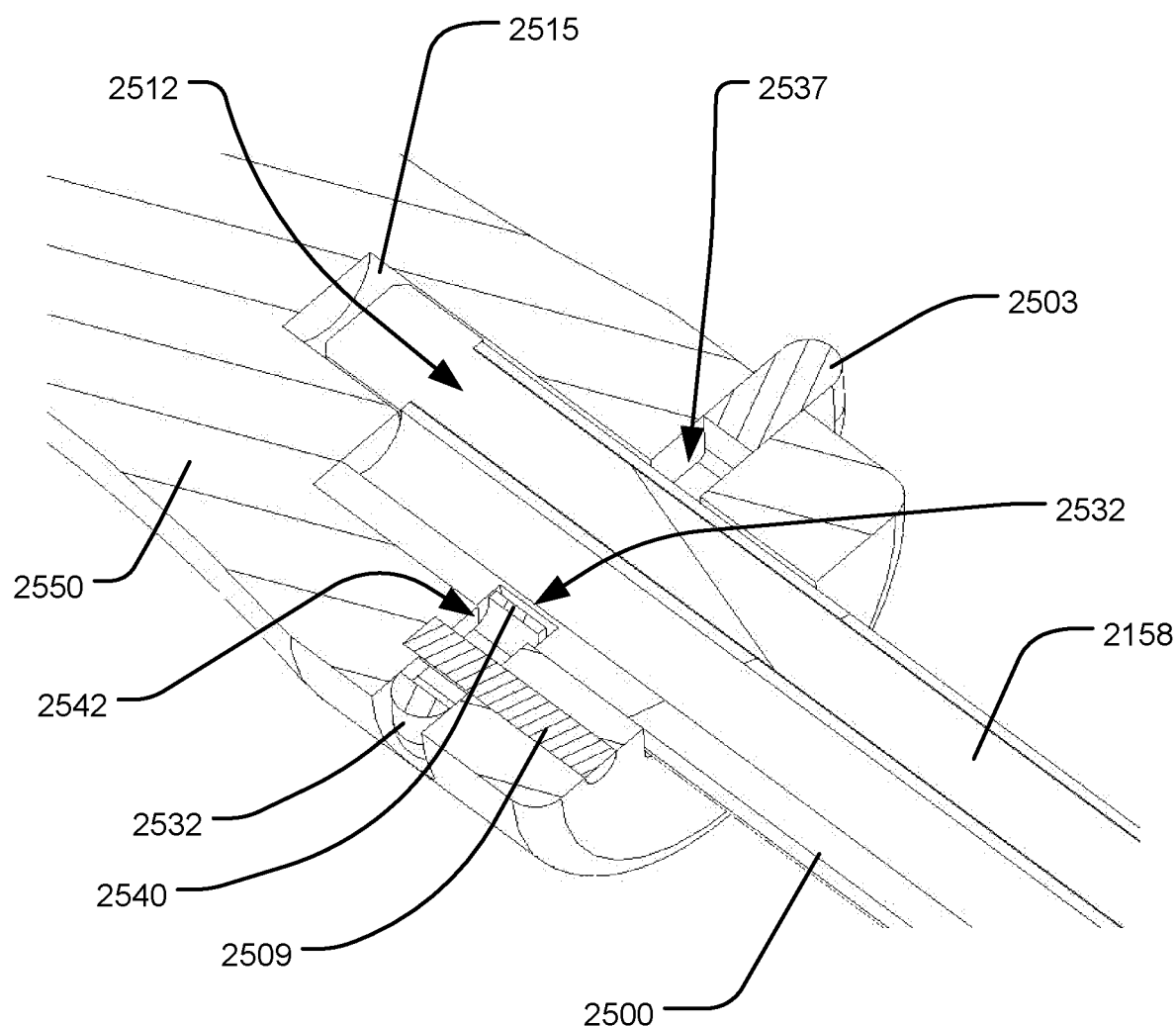
FIG. 33C is an enlarged, cross-sectional view of the handle and insertion shaft of FIGS. 33A-B connected to one another.

As shown in FIGS. 33A-C, the proximal end of the insertion shaft 2500 may define a locking mechanism 2534 for securely coupling to the sliding lock mechanism 2535. Specifically, the locking mechanism 2534 is shaped to fit securely within a correspondingly shaped receptacle 2515 in the distal end of the handle 2550. The locking mechanism 2534 includes a recess 2532 for engaging the sliding lock mechanism 2535, as discussed below. The sliding lock mechanism 2535 operates similarly to the sliding lock mechanism 535 of the connect cap 504 illustrated in FIG. 11A. That is, the sliding lock mechanism 2535 may be slidable within the distal end of the handle 2550, and it may be biased by one or more springs 2507 so that a button 2503 of the sliding lock mechanism 2535 is biased to project outwardly from an exterior surface of the handle 2550. A stop pin 2509 is received through a slot 2542 in the sliding lock mechanism 2535 to constrain the travel of the sliding lock mechanism 2535, such that the sliding lock mechanism 2535 is retained within the handle 2550. The sliding lock mechanism 2535 includes a central hole 2537 that is shaped to receive the locking mechanism 2534 of the insertion shaft 2500. When handle 2550 is being attached to the proximal end of the insertion shaft 2500, as illustrated in FIGS. 33A-33C, button 2503 is pressed, causing the springs 2507 to compress, so that the central hole 2537 becomes aligned with the locking mechanism 2534. Once the receptacle 2515 of the handle 2550 receives the locking mechanism 2534 of the insertion shaft 2500, button 503 is released, causing the springs 2507 to de-compress and lock the locking mechanism 2534 to the sliding lock mechanism 2535. Specifically, when the button 2503 is released, the sliding lock mechanism 2535 slides such that stop pin 2509 slides within the slot 2542, and the end 2540 of central opening 2537 slides into the recess 2532 of the locking mechanism 2534. Due to the close fit between the locking mechanism 2534 and the correspondingly shaped receptacle 2515 in the distal end of the handle 2550, the engagement of the sliding lock mechanism 2535 with the recess 2532 prevents the handle 2550 from moving longitudinally and becoming disconnected from the insertion shaft 2500 when the button is in its undepressed position. Removal of the handle 2550 is then done through the reverse process, by pressing the button 2503 of the sliding lock mechanism 2535 and lifting the handle 2550 off of the insertion shaft 2500.

Figure 34A:
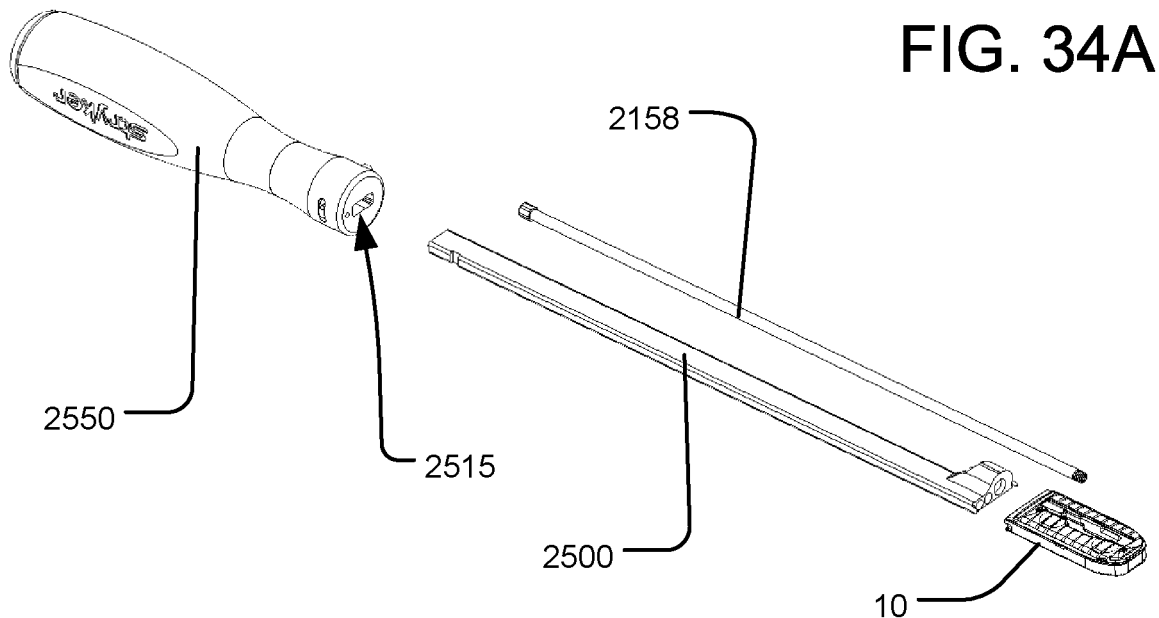
FIG. 34A is an exploded view of a delivery tool of the implant delivery system of FIG. 32.
Figure 34B:
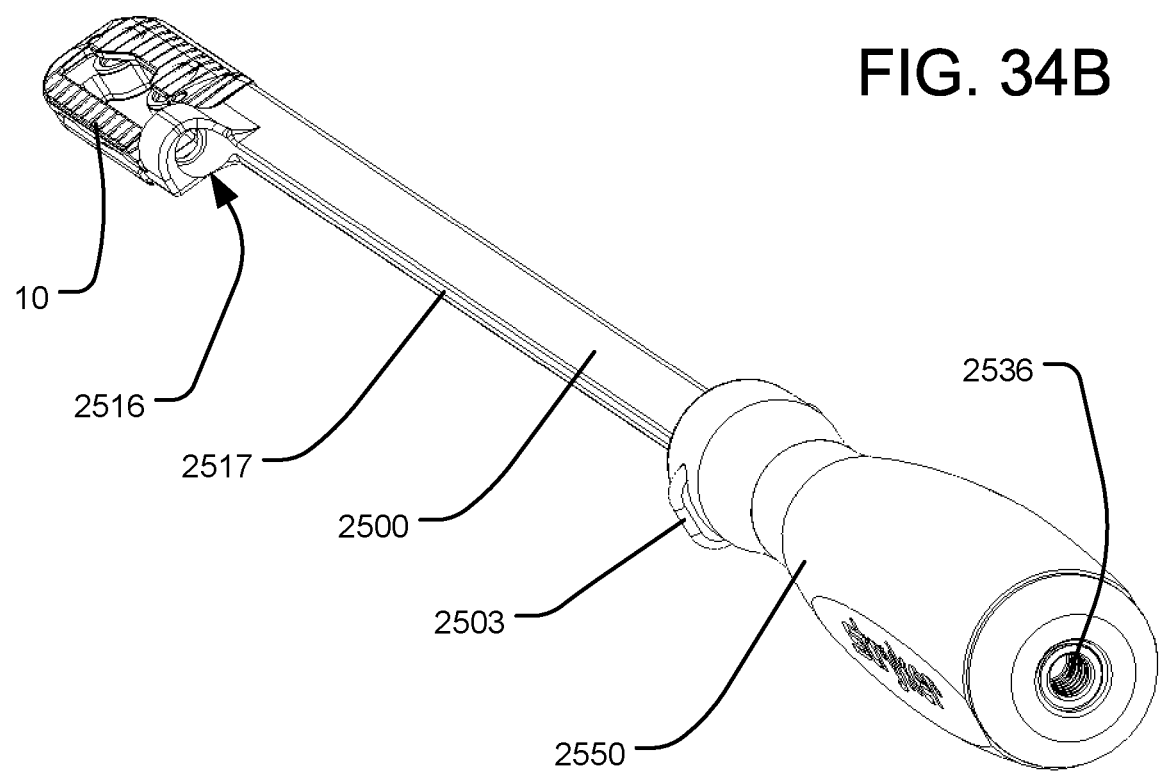
FIG. 34B is a perspective view of the delivery tool of FIG. 34A connected to an expandable implant.
Figure 35A:
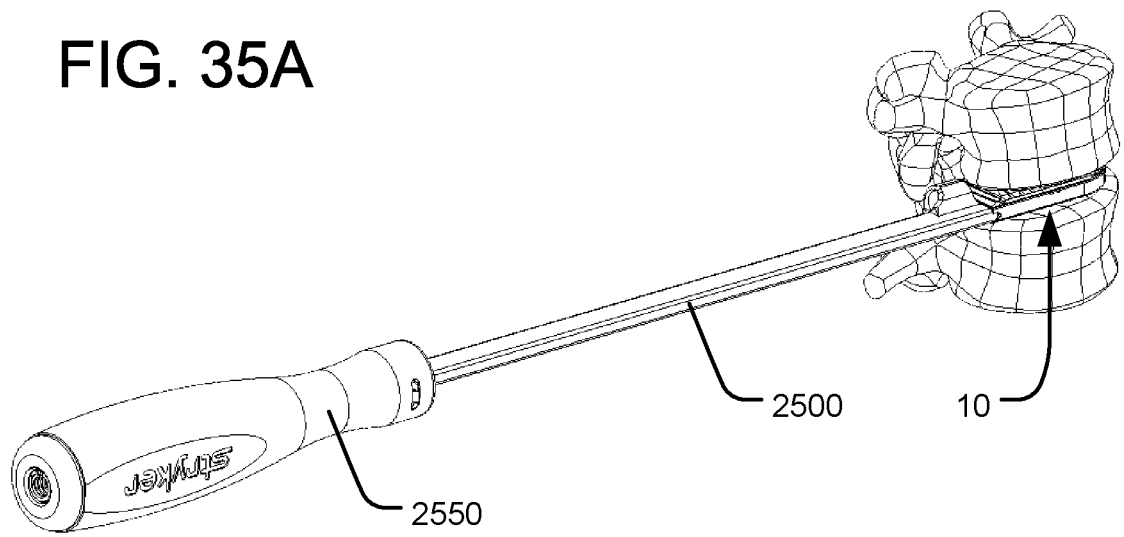
FIG. 35A is a perspective view of the delivery tool inserting and placing the implant into the intervertebral space.
Figure 35B:
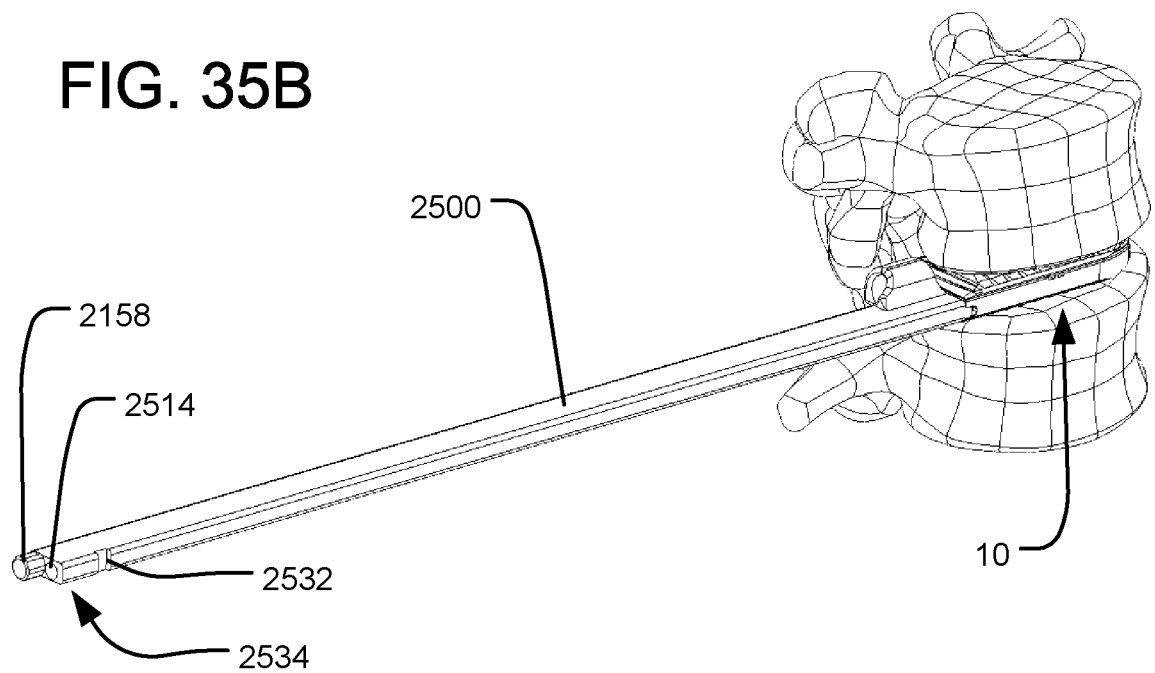
FIG. 35B is a perspective view of the arrangement of FIG. 35A, with the handle removed from the insertion shaft of the delivery tool.

The insertion of the implant 10 may be accomplished using the components illustrated in FIGS. 34A-35B. FIG. 34A shows an exploded view of the handle 2550, the insertion shaft 2500, the rotatable threaded member 2158, and the implant 10. The rotatable threaded member 2158 includes a threaded portion on its distal end, which is inserted into the proximal end of a receptacle 2512 in the insertion shaft 2500. The rotatable threaded member 2158 then extends out the distal end of the insertion shaft 2500 and screws into the implant 10 to attach the implant 10 to the insertion shaft 2500, a system which can remain intact throughout the procedure. The handle 2550 then attaches to the proximal end of the insertion shaft 2500, e.g., via sliding lock mechanism 2535, so that the handle 2550 can be grasped by the surgeon during insertion of the implant 10 into the intervertebral space. The proximal end of the handle 2550 also desirably provides a durable impaction surface to help insert or place expandable implant 10. As shown in FIG. 34B, the handle 2550 includes a threaded bore 2536 on its proximal end for receiving a slap hammer, which can help with removal of the implant 10 if necessary. Placement of the implant 10 into the disc space is shown in FIG. 35A. After placement is complete, the handle 2550 can be removed from the insertion shaft 2500, as shown in FIG. 35B. The insertion shaft 2500 is designed to have minimal cross-sectional dimensions, so as to increase visualization of the implant and its expansion, both directly by the surgeon as well as via fluoroscopy. The removal of the handle 2550 enhances visibility even further.

Figure 36:
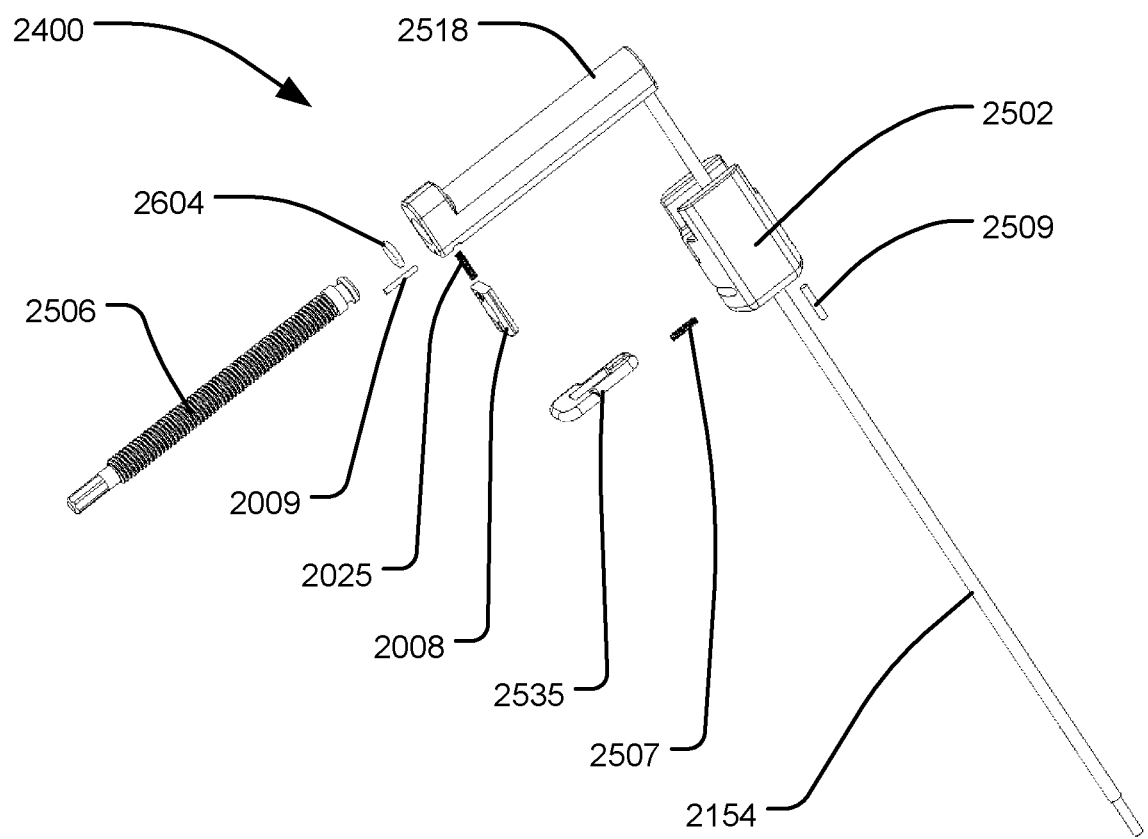
FIG. 36 is an exploded view of a fluid delivery system of the implant delivery system of FIG. 32.
Figure 37A:
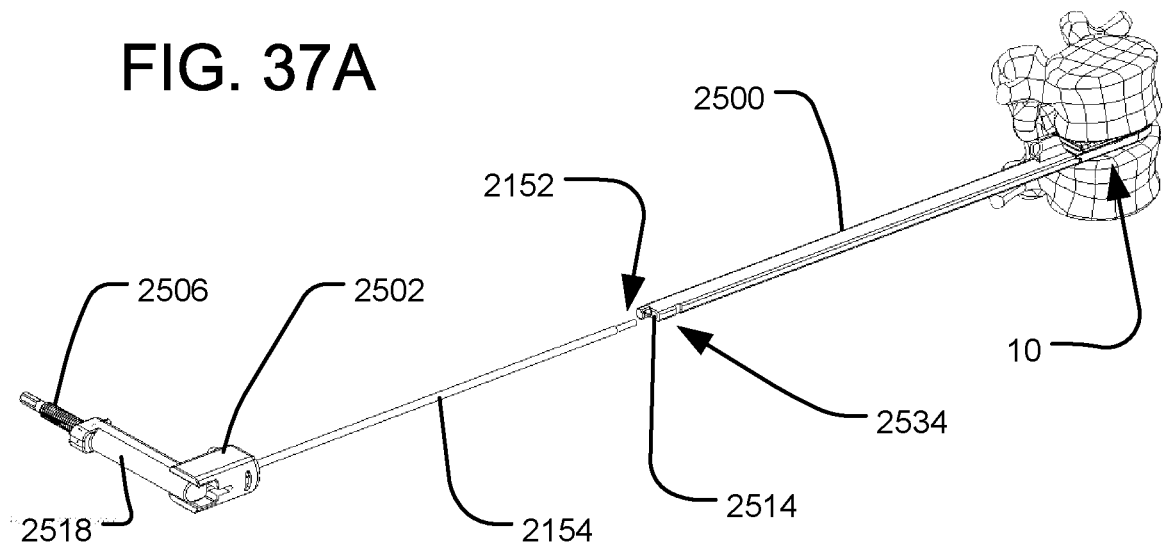
FIGS. 37A-37B are perspective views of the insertion of the fluid delivery system of FIG. 36 into the delivery tool.
Figure 37B:
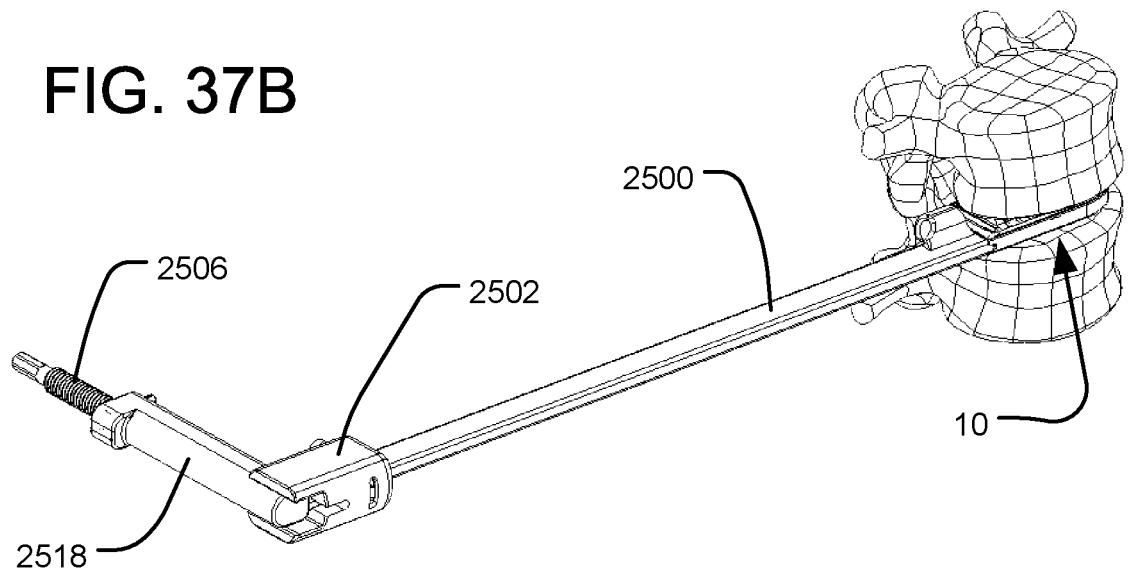

After removing the handle 2550 from the insertion shaft 2500, the fluid delivery system 2400 may be attached to the insertion shaft 2500 to expand the implant 10. An exploded view of the fluid delivery system 2400 is illustrated in FIG. 36. The fluid delivery system 2400 includes a fluid delivery cannula 2154, a reservoir 2518, a plunger 2506, and a connect cap 2502. The connect cap 2502 desirably includes a sliding lock mechanism 2535 for attaching the fluid delivery system 2400 to the locking mechanism 2534 at the proximal end of the insertion shaft 2500, in the same manner shown in FIGS. 33A-C. As shown in FIGS. 37A-37B, the distal end of the fluid delivery cannula 2154 may be inserted into a receptacle 2514 on the proximal end of the insertion shaft 2500. After the fluid delivery cannula 2154 is seated in the insertion shaft 2500, the outlet 2152 for delivering pressurized fluid will be located at the distal end of the insertion shaft 2500, where it can fluidly communicate with the inlet of a pressure channel on the proximal end of the expandable implant 10. Specifically, in the same manner shown in FIGS. 15A and 7B, the outlet 2152 of this embodiment may likewise project from the distal end of the insertion shaft 2500, such that it is partially received within the inlet of the expandable implant, where it can form a sealing connection by engaging an o-ring positioned within the pressure channel of the implant 10. In the present embodiment, the reservoir 2518 may be angled with respect to the fluid delivery cannula 2154, which preferably positions the reservoir 2518 out of the line of site of the surgeon and/or the fluoroscope to the implant. Desirably, such positioning improves visibility for viewing the implant 10, as well as relocating a user's hands outside the radiation area of the fluoroscope. Preferably, the reservoir 2518 may be angled at 90 degrees with respect to the fluid delivery cannula 2154, although other angles to position the reservoir 2518 away from the viewing area could also be used.

Figure 38A:
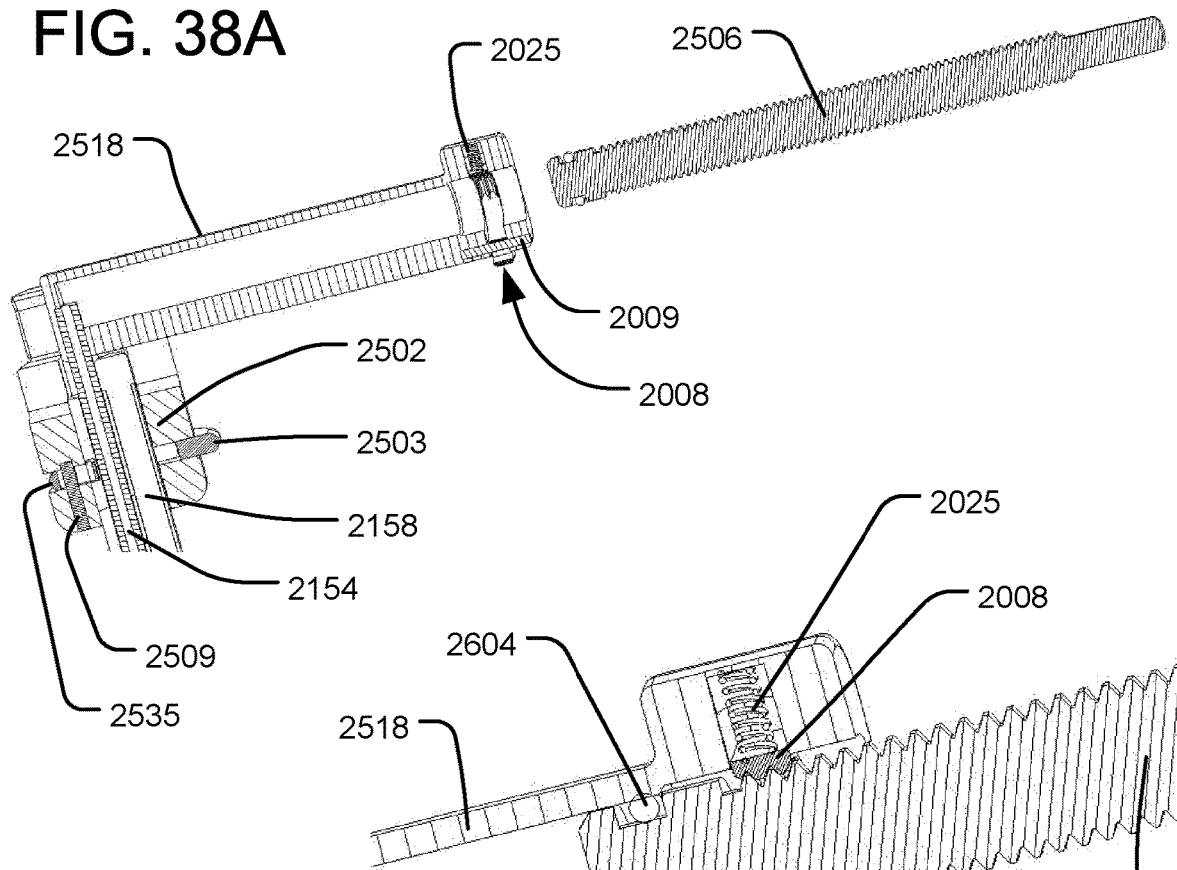
FIG. 38A-38B are cross-sectional views of the insertion of a plunger of the fluid delivery system of FIG. 36 into a reservoir of the fluid delivery system.
Figure 38B:
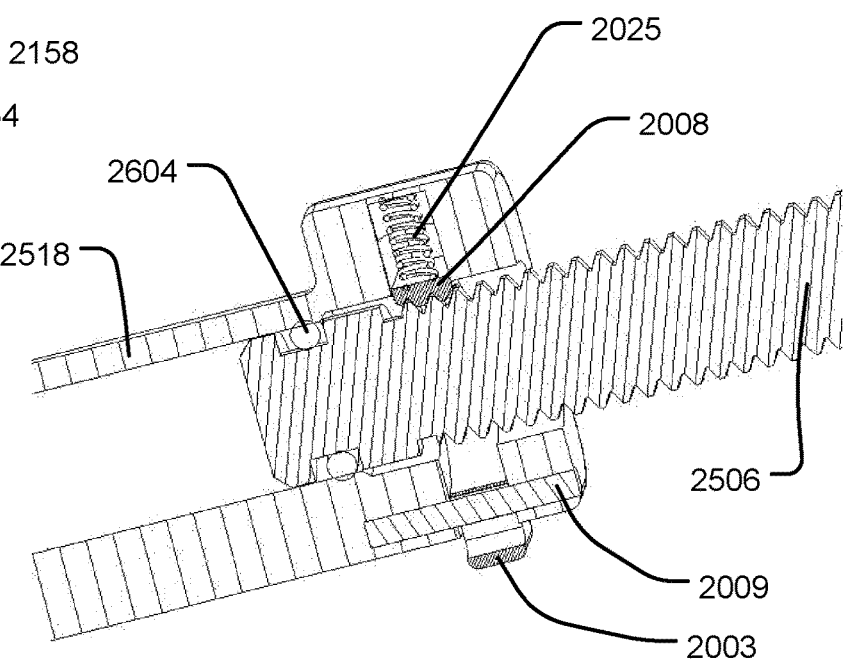
Figure 38C:
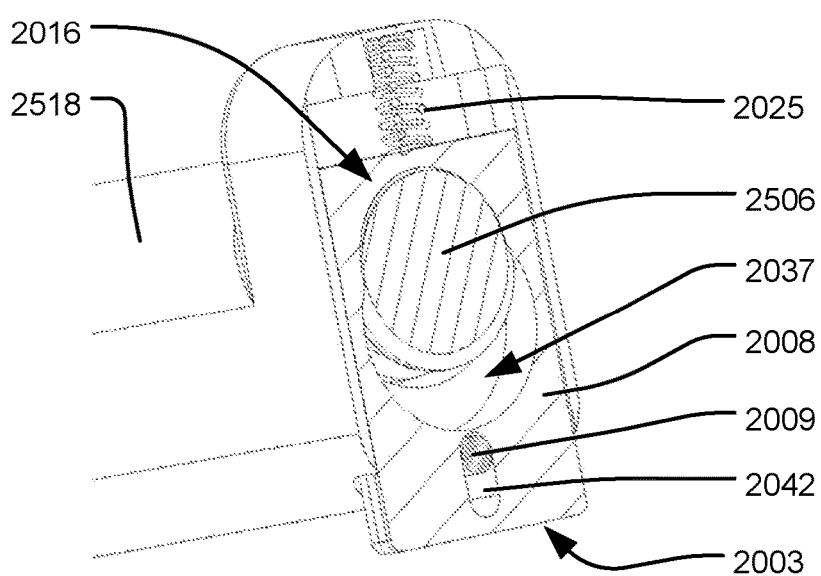
FIG. 38C is a perspective, cross-sectional view of a plunger engagement mechanism engaging the plunger of the fluid delivery system of FIG. 36.

The reservoir 2518 may receive the threaded plunger 2506 to pressurize the system. The plunger 2506 may be engaged by a plunger engagement mechanism 2008, as shown in FIGS. 38A-C. Like the selector mechanism 1004 of FIGS. 31A-31E, the plunger engagement mechanism 2008 of the embodiment of FIGS. 38A-C may be designed to allow two modes of travel by the plunger 2506. The plunger engagement mechanism 2008 is slidable within a proximal portion of the reservoir 2518, and it may be biased by one or more springs 2025 so that a button 2003 of plunger engagement mechanism 2008 is biased to project outwardly from an exterior surface of the reservoir 2518. A stop pin 2009 is received through a slot 2042 in the plunger engagement mechanism 2008 to constrain the travel of the plunger engagement mechanism 2008, such that the plunger engagement mechanism 2008 is retained within the reservoir 2518. The plunger engagement mechanism 2008 includes a central hole 2037 that is shaped to receive the plunger 2506 through it. At least one side of the hole includes a threaded portion 2016 structured to engage the threads of the plunger 2506. When the plunger 2506 is inserted into the reservoir 2518, button 2003 is pressed, causing the spring 2025 to compress, so that plunger 2506 can freely slide though the central hole 2037. Thus, holding the button 2003 in a depressed state allows for one of the two modes of travel by the plunger 2506, in which the threaded portion 2016 of the plunger engagement mechanism 2008 is disengaged from the threads of the plunger 2506, so that the plunger can travel along the reservoir 2518 by sliding the plunger 2506 linearly through the opening 2037 in the plunger engagement mechanism 2008. By releasing the button 2003, the spring 2025 will de-compress and cause the threaded portion 2016 of the plunger engagement mechanism 2008 to move into engagement with the threads of the plunger 2506, which activates the other mode of travel by the plunger 2506. That is, due to the threaded engagement between the threads of the plunger 2506 and the threaded portion 2016 of the plunger engagement mechanism 2008, the plunger can travel along the reservoir 2518 by rotation about the longitudinal axis of the plunger.

As with the embodiment of the selector mechanism 1004 of FIGS. 31A-31E, the two modes of travel of the plunger 2506 through the plunger engagement mechanism 2008 may desirably permit the plunger 2506 to advance the hydraulic fluid into the implant in the rotational, threaded engagement mode, and then the plunger 2506 can be quickly released by depressing the button 2003 and pulling the plunger 2506 in the proximal direction. The two states of engagement between the plunger engagement mechanism 2008 and the plunger 2506 may also give the surgeon a choice between two modes for delivery of the hydraulic fluid into the implant. That is, the surgeon may use the threaded advancement mode if a slower and more controlled advancement is appropriate, and/or if it is desirable to employ the mechanical advantage provided by the screw drive to amplify the input force. The surgeon may also choose to use the sliding, non-threaded mode if more rapid advancement of the plunger is desirable. The sliding, non-threaded mode may also desirably allow the plunger 2506 to be initially positioned into or removed from the reservoir 2518 relatively quickly, by eliminating the need to threadedly advance or retract the plunger 2506 the entire distance to the desired position.

After the implant 10 has been expanded under the influence of the pressurized fluid, the implant 10 may be repositioned (if desired) by unlocking the expansion mechanism, such as by pressing distally on the unlocking tether 212a. In one embodiment of the fluid delivery system 2400, the fluid delivery cannula 2154 may be advanceable distally relative to the reservoir 2518, so as to push on the unlocking tether 212a within the expandable implant 10, in the same manner as illustrated in FIG. 15D. In another embodiment, the fluid delivery system 2400 may be removed from the insertion shaft 2500, and then a tube or other rigid, elongate component may be inserted into the same receptacle 2514 at the proximal end of the insertion shaft, so as to travel through the insertion shaft 2500 and push the unlocking tether 212a of the implant 10.

Figure 39A:
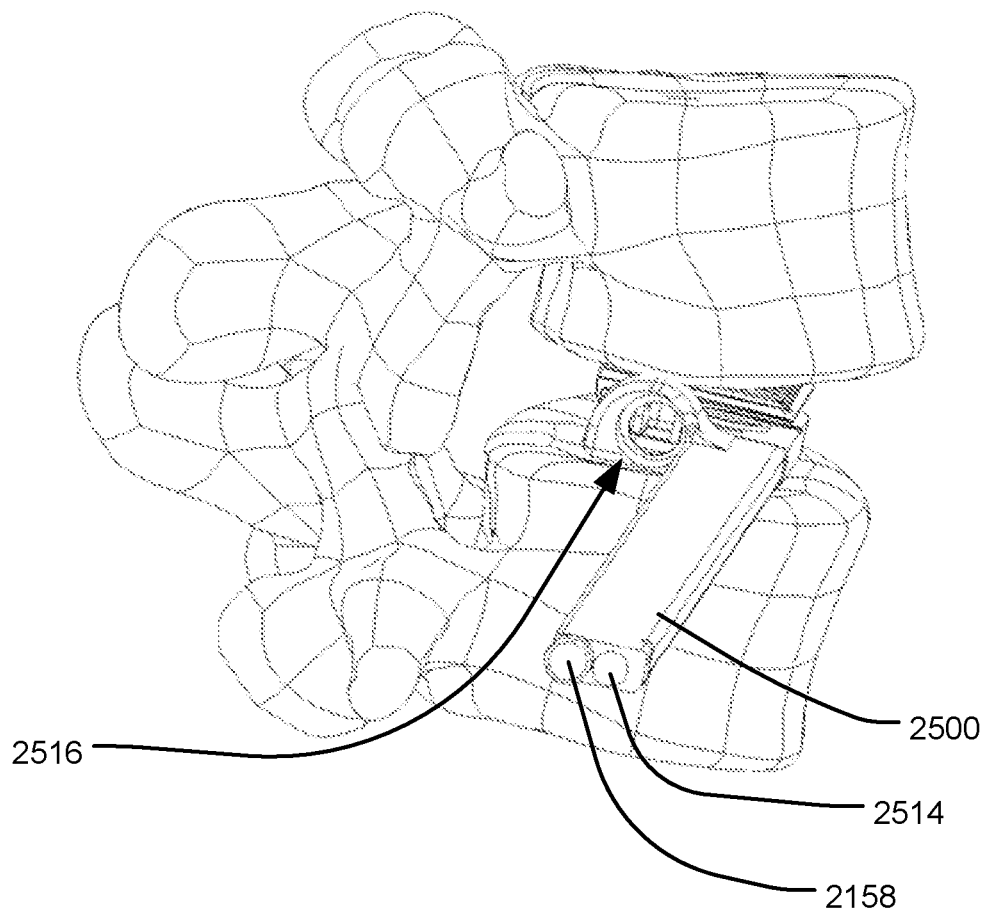
FIGS. 39A-39B are perspective views of the insertion shaft of the implant delivery system of FIG. 32 connected to the expanded implant within the intervertebral space.
Figure 39B:
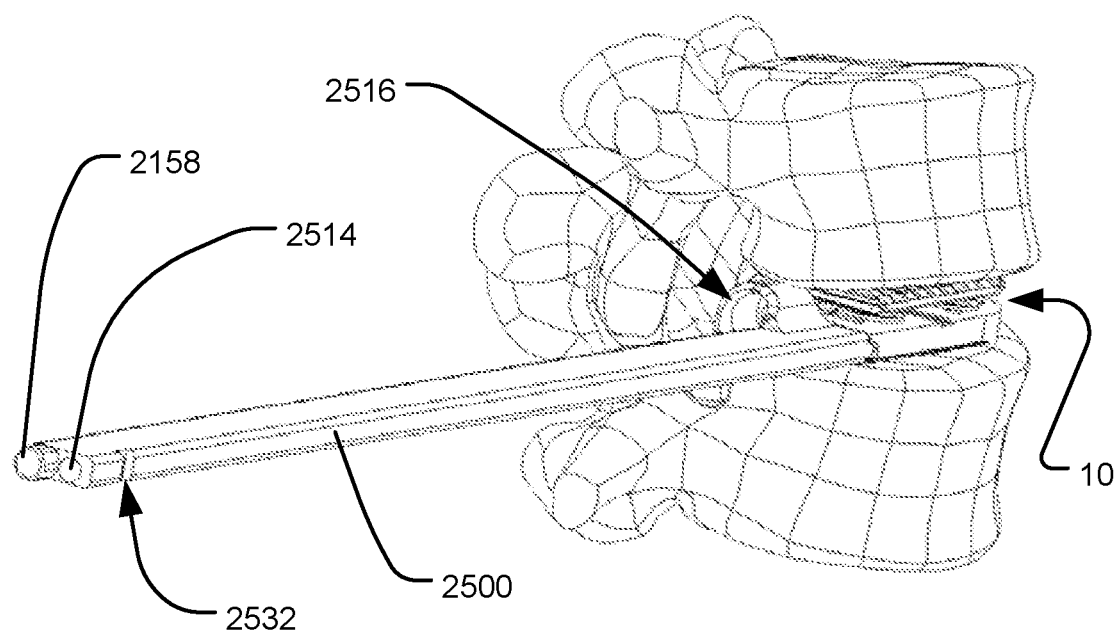
Figure 40A:
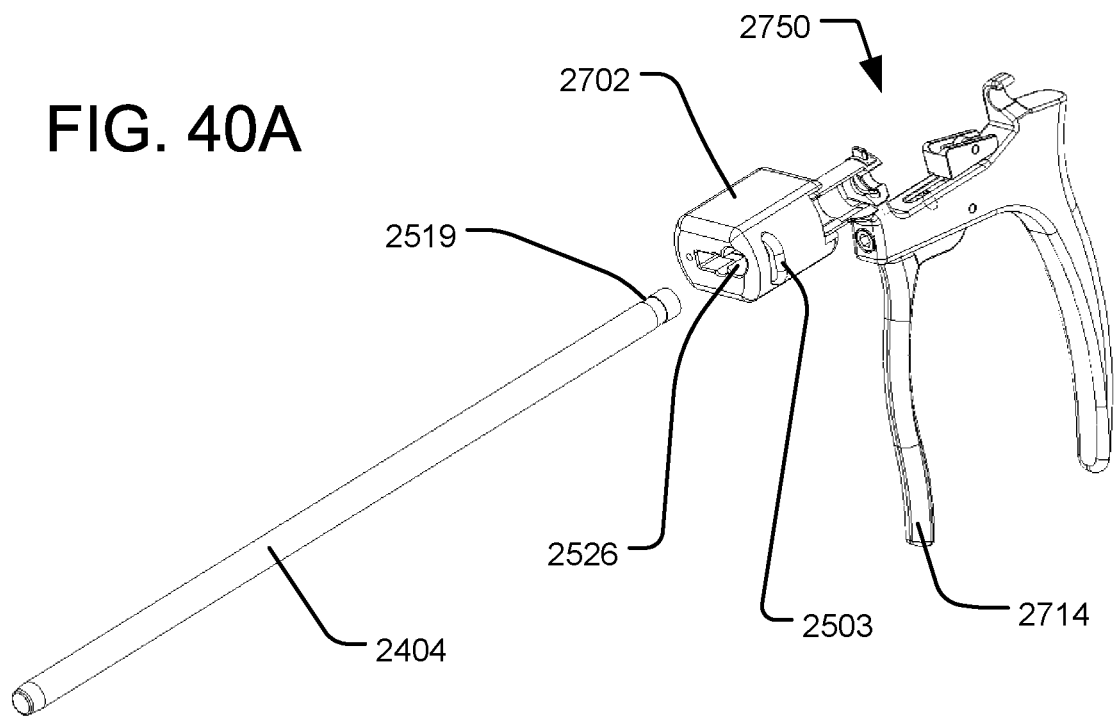
FIGS. 40A-40B are perspective views of the insertion of a bone graft supply line into a bone graft supply system of the implant delivery system of FIG. 32.
Figure 40B:
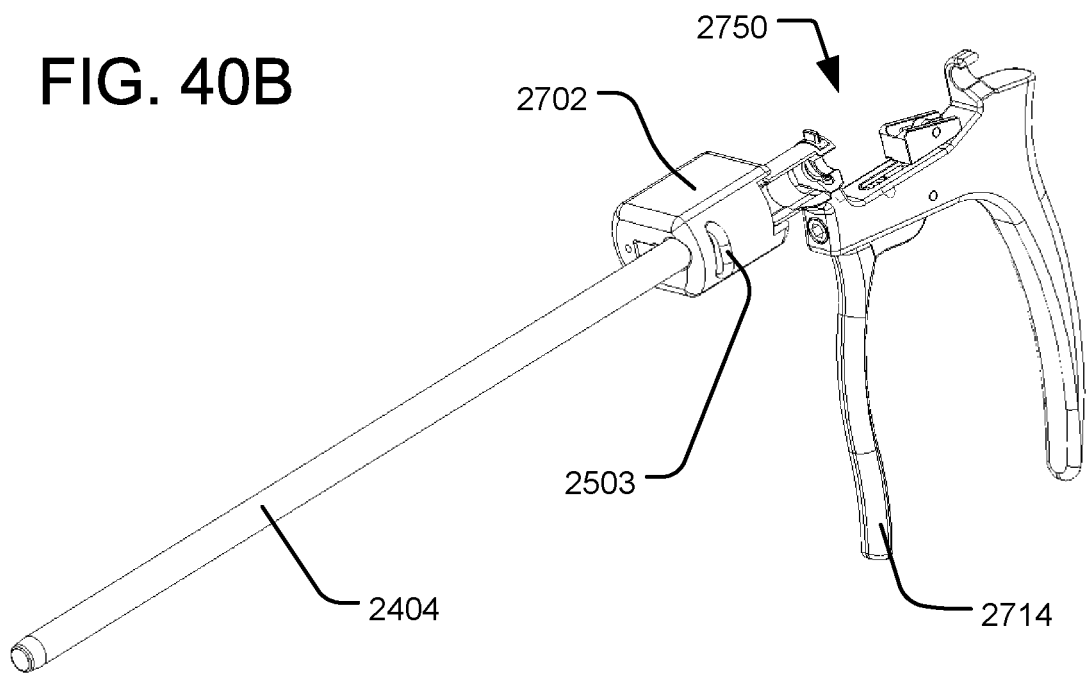
Figure 41A:
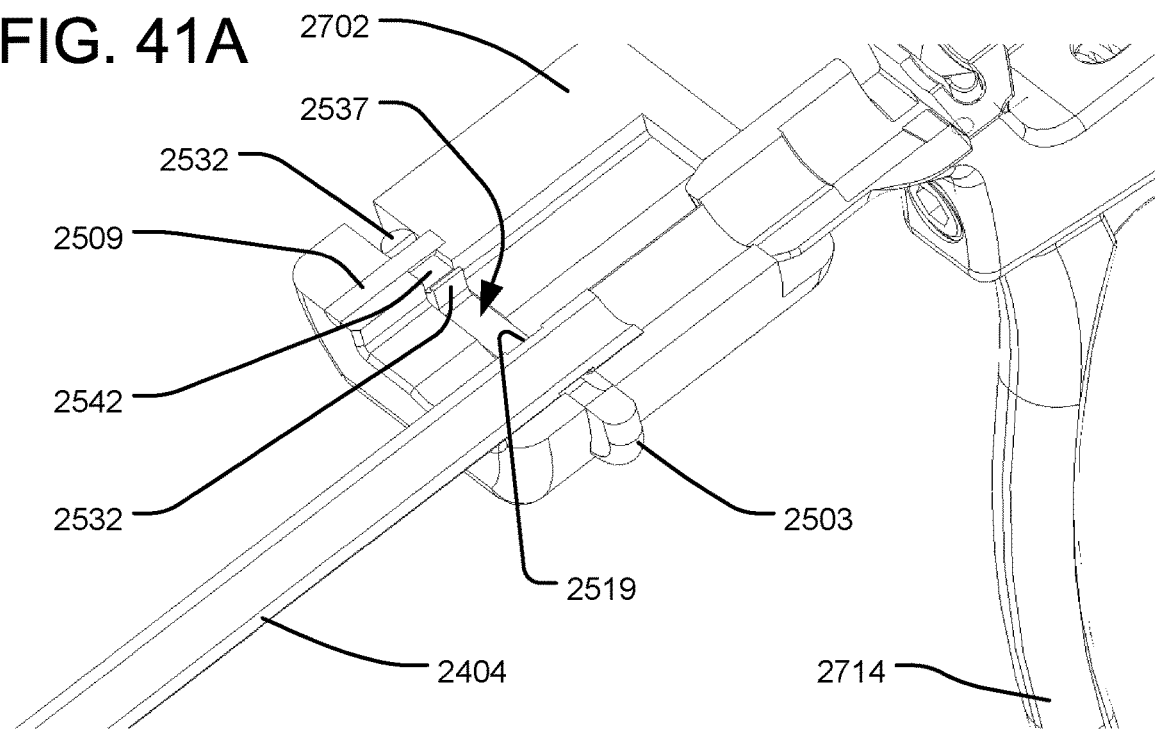
FIGS. 41A-41B are perspective, cross-sectional views of the bone graft supply line connected to the bone graft supply system of FIGS. 40A-B.
Figure 41B:
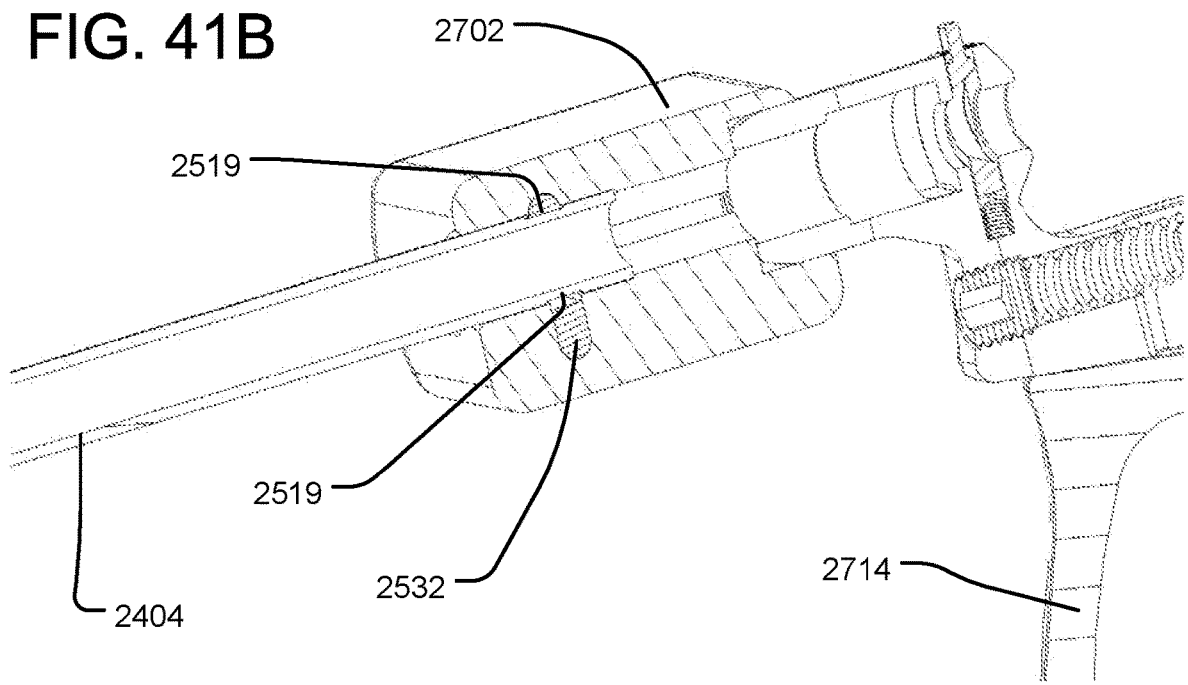

Once the implant is placed and expanded, the fluid delivery system 2400 may be removed from the insertion shaft 2500, as shown in FIGS. 39A-B. The bone graft supply system may then be attached to the insertion shaft 2500 to fill the expanded implant 10 with bone graft material. The bone graft supply system may include a bone graft gun 2750 having a connect cap 2702 and a bone graft supply line 2404. The steps of using the bone graft gun 2750 are shown in FIGS. 40A-42C. Specifically, the bone graft supply line 2404 may first be connected to the bone graft gun 2750, as shown in FIGS. 40A-B. The proximal portion of the bone graft supply line 2404 includes a recess 2519 around at least a portion of its outer periphery. That recess 2519 is shaped to engage the sliding lock mechanism 2535 of the connect cap 2702 of the bone graft gun 2750 in much the same manner that the recess 2532 on the insertion shaft 2500 engages the end 2540 of the central opening 2537 of the sliding lock mechanism 2535 in order to secure the insertion shaft 2500 to the handle 2550. Thus, both the bone graft supply line 2404 and the insertion shaft 2500 can be secured to the connect cap 2702 of the bone graft gun 2750 via the sliding lock mechanism 2535. In particular, with regard to the bone graft supply line 2404, the proximal portion of the bone graft supply line 2404 is inserted into a corresponding receptacle 2526 on the connect cap 2702 of the bone graft gun 2750 while the button 2503 of the sliding lock mechanism 2535 is depressed. The depressing of the button 2503 causes the central opening 2537 of the sliding lock mechanism 2535 to be positioned such that the proximal portion of the bone graft supply line 2404 can be received through the central opening 2537. Then, the bone graft supply line 2404 can be secured to the bone graft gun 2740 by releasing the button 2503, which results in the biasing of the sliding lock mechanism 2535 to a shifted position, in which a portion of the periphery of the central opening 2537 is received within the recess 2519 of the bone graft supply line 2404, as shown in FIG. 41B.

Figure 42A:
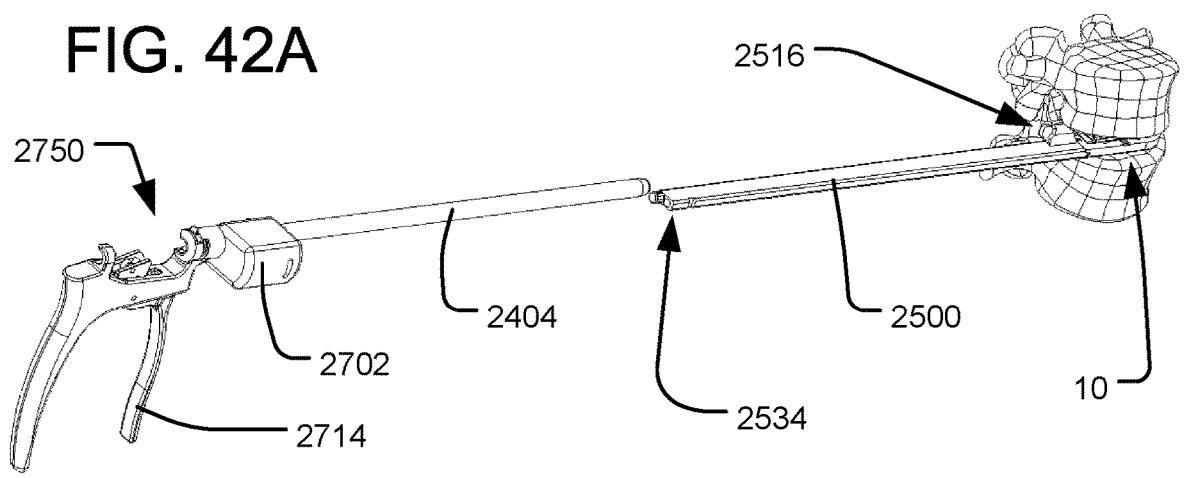
FIGS. 42A-42B are perspective views of the insertion of a bone graft supply system into the implant delivery system of FIG. 32.
Figure 42B:
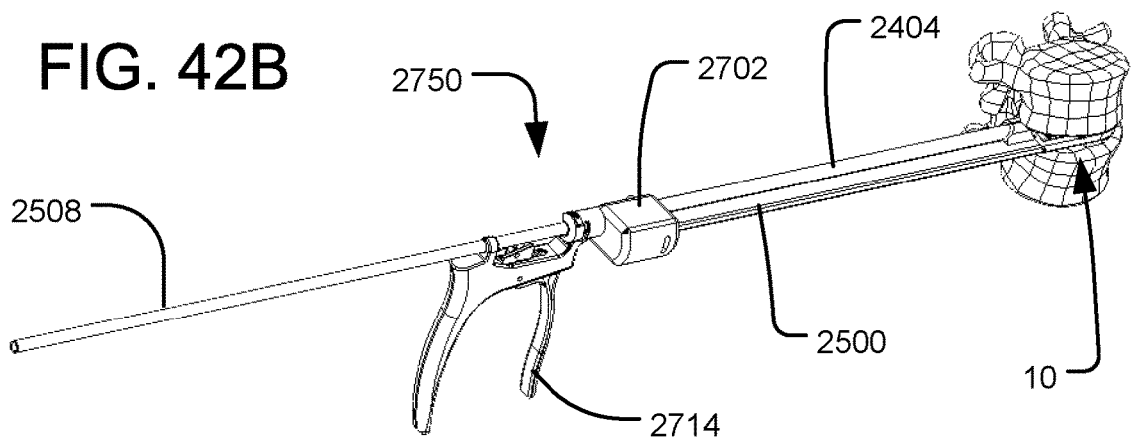
Figure 42C:
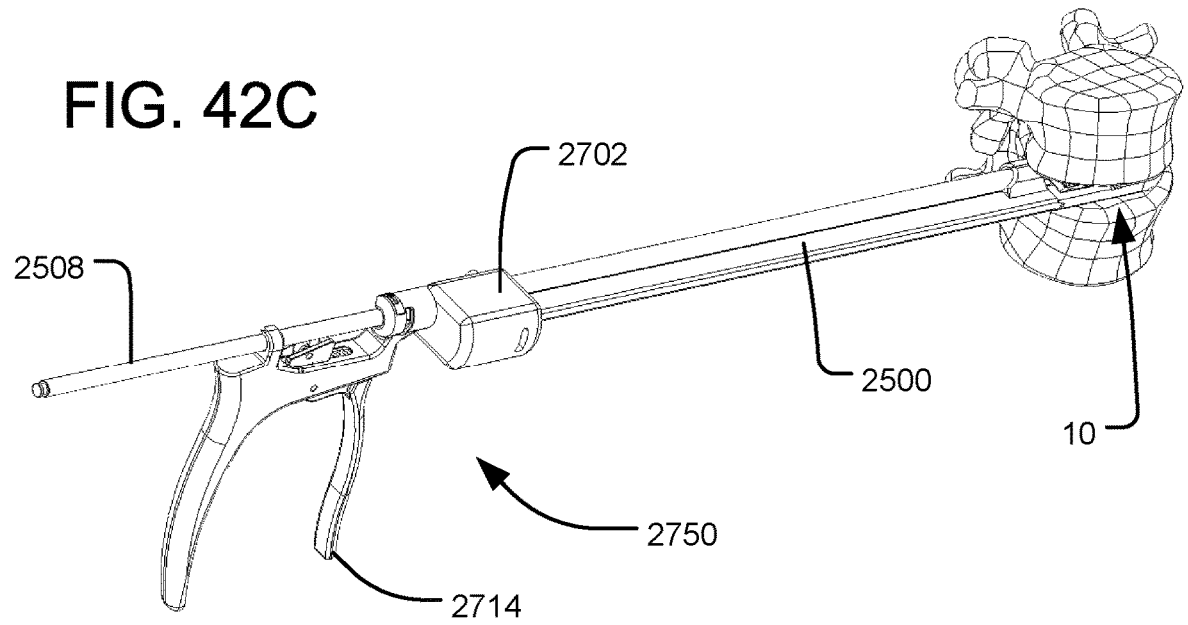
FIG. 42C is a perspective view of the bone graft supply system of FIGS. 42A-B injecting bone graft material into the implant.

The bone graft gun 2750 with attached bone graft supply line 2404 is then connected to the insertion shaft 2500, as shown in FIGS. 42A-B. Specifically, the distal end of the bone graft supply line 2404 is placed within an opening 2516 at the distal end of the insertion shaft 2500 (see FIGS. 34B and 39A), such that the bone graft supply line 2404 is positioned alongside the insertion shaft 2500, where it may be partially received in and supported by a groove or channel 2517 extending along the insertion shaft 2500 (see FIG. 34B). The connect cap 2702 of the bone graft supply gun 2750 is also connected to the locking mechanism 2534 at the proximal end of the insertion shaft 2500 via a sliding lock mechanism 2535 like that of handle 2550. The distal end of plunger 2508 is then inserted into the proximal end of the bone graft supply line 2404. Plunger 2508 is designed to work with the bone graft gun 2750 using a pistol-grip trigger 2714 and a ratcheting advancement mechanism like that shown in FIGS. 24A-B.

When all phases of the surgery are complete, the insertion shaft 2500 can be removed from the implant 10 by unthreading the rotatable threaded member 2158.

Figure 43:
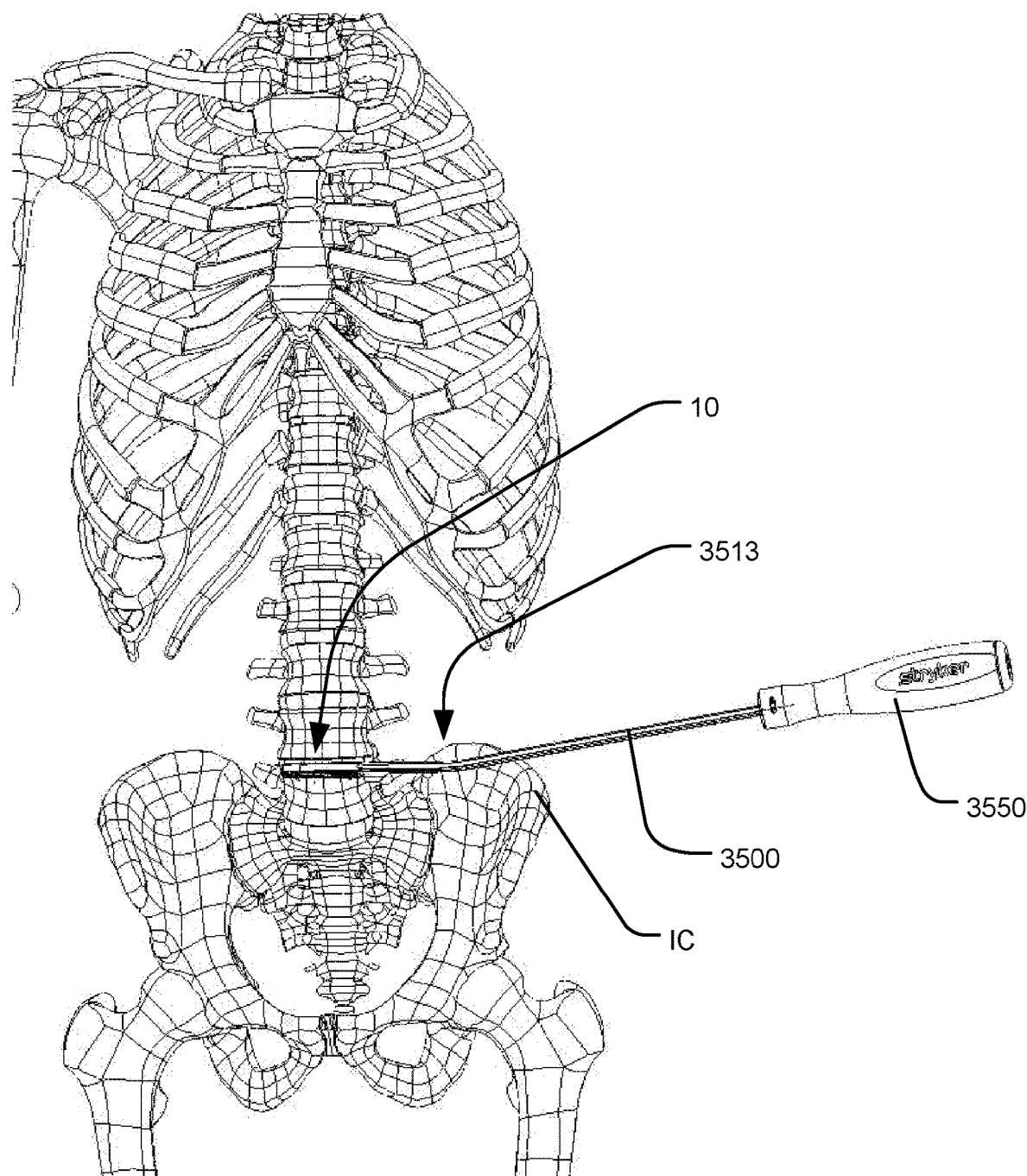
FIG. 43 is a simplified view showing a delivery tool in accordance with another embodiment of the present invention inserting an implant into an intervertebral space along a lateral approach.
Figure 44:
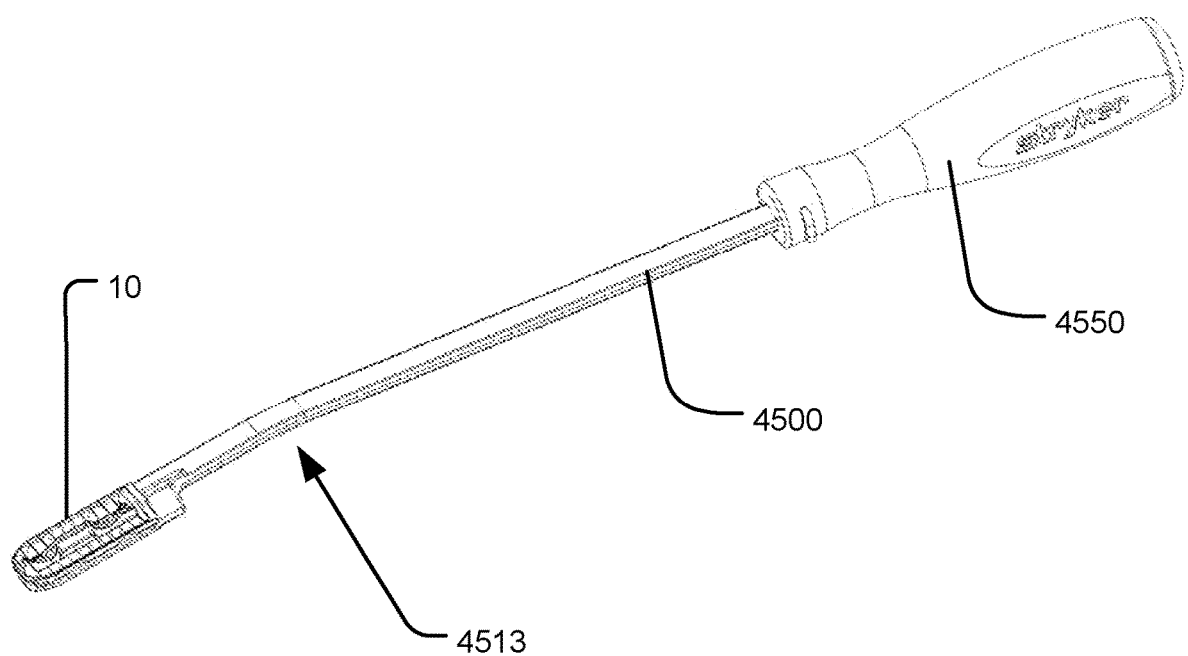
FIG. 44 is a perspective view of a delivery tool in accordance with another embodiment of the present invention.

In alternative embodiments, as illustrated in FIGS. 43-44, the insertion shaft may include bend angles within one or more planes. For example, for an L4/L5 lateral approach (e.g., in a trans-psoas or anterior-to-psoas ("ATP") approach), an insertion shaft 3500 may be provided having a single bend 3513 in a cephalad direction within the frontal or coronal plane. As shown in FIG. 43, such bend 3515 may allow the insertion shaft 3500 to avoid the iliac crest IC. A bend in the anterior direction within the horizontal or transverse plane may additionally or alternatively be provided. For example, for an ATP approach, an insertion shaft 4500 may be provided having a compound bend 4513, consisting of a cephalad bend like that shown in FIG. 43, as well as a bend in the anterior direction within the horizontal or transverse plane, as shown in FIG. 44. All of such bends are preferably located approximately 40 millimeters from the distal end of the insertion shaft 3500, and the bends preferably have an angle between 15 and 30 degrees.

One or more components of the delivery tool 100, such as handle 550, are desirably made of radiolucent material, such that they do not impair visualization of the implant 10 (e.g., by fluoroscopy) while it is being implanted and further manipulated. The components of the connect caps, including the sliding lock mechanisms, may be fabricated from a plastic to reduce blockage of imaging, while the fluid delivery cannula 2154 and the reservoir 2518 may be fabricated from a metal for strength and durability.

Particularly in the case of an insertion shaft 3500 having an angled bend, such as those shown in FIGS. 43-44, the rotatable threaded member 158 may be made of a flexible material or it may have a flexible portion corresponding to the position of the bend. The fluid delivery cannula 154 may also be fabricated from a flexible material, such as nitinol, to travel through the bent insertion shaft 3500. The bone graft supply line 404 may also be fabricated from a flexible material, or a non-flexible material having a bend that matches that of the insertion shaft 3500.

To assist the Patent Office and anyone else considering this application (or any patent issuing thereon) in interpreting the accompanying claims, Applicant notes that none of the claim language is intended to invoke the provisions of 35 U.S.C. § 112(f) unless the words "means for" or "step for" are explicitly used.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed:

1. A spinal implant system, comprising: a block for supporting an intervertebral implant while packing an interior cavity of the implant with graft material, comprising: a base; and a projection extending from the base, the projection being sized to be received through a first opening in the implant such that the projection is positioned at least partially within the interior cavity of the implant; and the intervertebral implant, wherein the implant includes a second opening on an opposite side of the implant from the first opening, and, wherein, when the implant is supported on the block with the projection received through the first opening in the implant, the second opening is oriented upwardly so as to receive a supply of graft material into the interior cavity through the second opening.

2. The spinal implant system of claim 1, wherein the projection of the block is configured to closely fit within the interior cavity of the implant such that graft material positioned within the interior cavity is prevented from flowing downwardly past an upper surface of the projection into a portion of the interior cavity occupied by the projection.

3. A delivery system for implantation of an implant into an intervertebral space, comprising:
   a block for supporting an intervertebral implant while packing an interior cavity of the implant with graft material, including a base and a projection extending from the base, the projection being sized to be received through a first opening in the implant such that the projection is positioned at least partially within the interior cavity of the implant; and the intervertebral implant, wherein the implant includes a second opening on an opposite side of the implant from the first opening, and, wherein, when the implant is supported on the block with the projection received through the first opening in the implant, the second opening is oriented upwardly so as to receive a supply of graft material into the interior cavity through the second opening;

an elongated tool having a proximal end and a distal end, the distal end being removably securable to the implant, wherein the proximal end has an attachment interface for detachable securement to a plurality of different modules, each module being adapted to effectuate a different function of the delivery system during the implantation of the implant.

4. The delivery system of claim 3, wherein a first one of the plurality of different modules is a handle.

5. The delivery system of claim 4, wherein the first module includes a plunger advanceable in a distal direction to drive graft material distally through the tool and into the implant.

6. The delivery system of claim 5, wherein the first module includes a pistol-grip handle having a trigger that is squeezable to drive the advancement of the plunger in the distal direction.

7. The delivery system of claim 3, wherein a first one of the plurality of different modules defines a flat impaction surface at a proximal end of a handle for driving the advancement of the tool.

8. The delivery system of claim 7, wherein the flat impaction surface is defined on a connect cap removably attachable to the handle.

9. The delivery system of claim 3, wherein a first one of the plurality of different modules is a bone graft supply system.

10. The delivery system of claim 3, wherein a first one of the plurality of different modules is an expander for actuating expansion of the implant.

11. The delivery system of claim 10, wherein the first module is a fluid delivery system for supplying a hydraulic fluid into the implant to expand the implant.

12. The delivery system of claim 11, further comprising a pressure gauge for displaying the pressure of the hydraulic fluid supplied to the implant.

13. The delivery system of claim 10, wherein the first module includes a plunger advanceable within a fluid reservoir for driving the hydraulic fluid into the implant via a fluid delivery cannula.

14. The delivery system of claim 13, wherein the fluid reservoir is oriented transverse to the fluid delivery cannula, such that the plunger is advanceable within the reservoir along a direction transverse to the fluid delivery cannula.

15. The delivery system of claim 13, wherein the first module includes a selector mechanism for switching between two different modes of travel by the plunger.

16. The delivery system of claim 15, wherein a first one of the two modes includes rotation of the plunger about its longitudinal axis such that the plunger travels along a threaded connection, and wherein a second one of the two modes includes sliding the plunger linearly along its longitudinal axis.

17. The delivery system of claim 3, wherein each of the different modules is securable to and detachable from the proximal end of the tool by depressing a button on the respective module.

* * * * *